(12) United States Patent
Yon et al.

(10) Patent No.: US 7,458,984 B2
(45) Date of Patent: Dec. 2, 2008

(54) SYSTEM AND METHOD FOR INDUCING HYPOTHERMIA WITH ACTIVE PATIENT TEMPERATURE CONTROL EMPLOYING CATHETER-MOUNTED TEMPERATURE SENSOR AND TEMPERATURE PROJECTION ALGORITHM

(75) Inventors: Steve A. Yon, San Diego, CA (US); Michael Magers, Encinitas, CA (US)

(73) Assignee: Innercool Therapies, Inc., San Diego, CA (US)

( * ) Notice: Subject to any disclaimer, the term of this patent is extended or adjusted under 35 U.S.C. 154(b) by 398 days.

(21) Appl. No.: 10/767,782

(22) Filed: Jan. 28, 2004

(65) Prior Publication Data
US 2004/0267339 A1 Dec. 30, 2004

Related U.S. Application Data

(60) Continuation-in-part of application No. 10/729,526, filed on Dec. 5, 2003, now Pat. No. 7,211,105, which is a continuation of application No. 10/082,964, filed on (Continued)

(60) Provisional application No. 60/449,803, filed on Feb. 24, 2003, provisional application No. 60/449,809, filed on Feb. 24, 2003, provisional application No. 60/456,137, filed on Mar. 20, 2003, provisional application No. 60/504,145, filed on Sep. 17, 2003, provisional application No. 60/247,203, filed on Nov. 7, 2000, provisional application No. 60/246,620, filed on Nov. 7, 2000, provisional application No. 60/281,771, filed on Apr. 5, 2001, provisional application No. 60/311,589, filed on Aug. 9, 2001, provisional application No. 60/312,409, filed on Aug. 15, 2001, provisional application No. 60/316,057, filed on Aug. 29, 2001, provisional application No. 60/316,922, filed on Aug. 31, 2001, provisional application No. 60/322,945, filed on Sep. 14, 2001.

(51) Int. Cl.
A61F 7/12 (2006.01)
(52) U.S. Cl. .................. 607/106; 607/104; 607/105
(58) Field of Classification Search ............... 607/96, 607/104–107
See application file for complete search history.

(56) References Cited

U.S. PATENT DOCUMENTS 4,153,048 A 5/1979 Magrini (Continued)

FOREIGN PATENT DOCUMENTS

EP 0428505 B2 3/2001

(Continued)

OTHER PUBLICATIONS

Anon; "Automatic Feedback Instrumentation for Hospital Room Utilizing Microsensors"; IBM Technical Disclosure Bulletin; vol. 29, No. 3, p. 1320 (Aug. 1986).

(Continued)

*Primary Examiner*—Roy D Gibson
(74) *Attorney, Agent, or Firm*—Mayer & Williams PC; Mark D Wieczorek Esq; Karin L. Williams Esq.

(57) ABSTRACT

Embodiments of the invention provide a system for temperature control of the human body. The system includes an indwelling catheter with a tip-mounted heat transfer element. The catheter is fluidically coupled to a console that provides a heated or cooled heat transfer working fluid to exchange heat with the heat transfer element, thereby heating or cooling blood. The heated or cooled blood then heats or cools the patient's body or a selected portion thereof. In particular, methods and devices, including software, are provided for administering cooling or rewarming and controlling the same based on a projected control temperature measured by a temperature sensor within the catheter.

44 Claims, 33 Drawing Sheets

Related U.S. Application Data

Feb. 25, 2002, now Pat. No. 6,660,028, which is a continuation of application No. 09/586,000, filed on Jun. 12, 2000, now Pat. No. 6,383,210, and a continuation-in-part of application No. 10/716,801, filed on Nov. 18, 2003, now Pat. No. 7,052,508, which is a continuation of application No. 09/414,184, filed on Oct. 7, 1999, now Pat. No. 6,325,818, and a continuation-in-part of application No. 10/714,070, filed on Nov. 14, 2003, now abandoned, which is a continuation of application No. 10/095,753, filed on Mar. 11, 2002, now Pat. No. 6,695,873, which is a division of application No. 09/757,124, filed on Jan. 8, 2001, now Pat. No. 6,540,771, which is a division of application No. 09/215,038, filed on Dec. 16, 1998, now Pat. No. 6,261,312, which is a continuation-in-part of application No. 09/103,342, filed on Jun. 23, 1998, now Pat. No. 6,096,068, which is a continuation-in-part of application No. 09/047,012, filed on Mar. 24, 1998, now Pat. No. 5,957,963, which is a continuation-in-part of application No. 09/102,287, filed on Jan. 23, 1998, now Pat. No. 6,051,019, and a continuation-in-part of application No. 10/411,001, filed on Apr. 9, 2003, now Pat. No. 7,094,253, which is a continuation of application No. 10/005,416, filed on Nov. 7, 2001, now Pat. No. 6,585,752, and a continuation-in-part of application No. 09/586,000, filed on Jun. 2, 2000, now Pat. No. 6,383,210, and application No. 09/566,531, May 8, 2000, now abandoned, which is a continuation of application No. 09/103,342, filed on Jun. 23, 1998, now Pat. No. 6,096,068, which is a continuation-in-part of application No. 09/047,012, filed on Mar. 24, 1998, now Pat. No. 5,957,963, which is a continuation-in-part of application No. 09/012,287, filed on Jan. 23, 1998, now Pat. No. 6,051,019, and a continuation-in-part of application No. 10/322,337, filed on Dec. 16, 2002, now Pat. No. 6,740,109, which is a continuation of application No. 09/292,532, filed on Apr. 15, 1999, now abandoned, which is a continuation-in-part of application No. 09/103,342, filed on Jun. 23, 1998, now Pat. No. 6,096,068, and a continuation-in-part of application No. 09/052,545, filed on Mar. 31, 1998, now Pat. No. 6,231,595, and a continuation-in-part of application No. 09/047,012, filed on Mar. 24, 1998, now Pat. No. 5,957,963, and a continuation-in-part of application No. 10/219,874, filed on Aug. 14, 2002, and a continuation-in-part of application No. 09/650,940, filed on Aug. 30, 2000, now Pat. No. 6,482,226, and a continuation-in-part of application No. 09/785,243, filed on Feb. 16, 2001, now Pat. No. 6,818,011, and a continuation-in-part of application No. 09/566,531, filed on May 8, 2000, now abandoned, and a continuation-in-part of application No. 09/757,124, filed on Jan. 8, 2001, now Pat. No. 6,540,771, and a continuation-in-part of application No. 09/714,749, filed on Nov. 16, 2000, now Pat. No. 6,468,296, and a continuation-in-part of application No. 09/621,051, filed on Jul. 21, 2000, now Pat. No. 6,582,455, and a continuation-in-part of application No. 09/800,159, filed on Mar. 6, 2001, now abandoned, and a continuation-in-part of application No. 09/292,532, filed on Apr. 15, 1999, now abandoned, and a continuation-in-part of application No. 09/379,295, filed on Aug. 23, 1999, now abandoned, and a continuation-in-part of application No. 09/885,655, filed on Jun. 20, 2001, now Pat. No. 6,676,690, and a continuation-in-part of application No. 09/246,788, filed on Mar. 28, 2001, now Pat. No. 6,491,716, and a continuation-in-part of application No. 09/797,028, filed on Feb. 27, 2001, now abandoned, and a continuation-in-part of application No. 09/607,799, filed on Jun. 30, 2000, now Pat. No. 6,464,716, and a continuation-in-part of application No. 09/519,022, filed on Mar. 3, 2000, now Pat. No. 6,379,378, and a continuation-in-part of application No. 10/082,964, filed on Feb. 25, 2002, now Pat. No. 6,660,028, and a continuation-in-part of application No. 09/539,932, filed on Mar. 31, 2000, now Pat. No. 6,491,039, and a continuation-in-part of application No. 09/658,950, filed on Sep. 11, 2000, now abandoned, and a continuation-in-part of application No. 09/373,112, filed on Aug. 11, 1999, and a continuation-in-part of application No. 10/007,545, filed on Nov. 6, 2001, now Pat. No. 6,719,779, and a continuation-in-part of application No. 10/005,416, filed on Nov. 7, 2001, now Pat. No. 6,585,752, and a continuation-in-part of application No. 10/117,733, filed on Apr. 4, 2002, now Pat. No. 6,702,841, and a continuation-in-part of application No. 10/210,819, filed on Jul. 31, 2002, now Pat. No. 6,679,907, which is a continuation of application No. 09/246,788, filed on Feb. 9, 1999, now Pat. No. 6,491,716, which is a continuation-in-part of application No. 09/103,342, filed on Jun. 23, 1998, now Pat. No. 6,096,068, and a continuation-in-part of application No. 09/052,545, filed on Mar. 31, 1998, now Pat. No. 6,231,595, and a continuation-in-part of application No. 09/215,038, filed on Dec. 16, 1998, now Pat. No. 6,261,312, and a continuation-in-part of application No. 09/215,039, filed on Dec. 16, 1998, now Pat. No. 6,251,129, and a continuation-in-part of application No. 09/232,177, filed on Jan. 15, 1999, now Pat. No. 6,245,095, and a continuation-in-part of application No. 10/161,107, filed on May 30, 2002, now Pat. No. 6,702,842, which is a continuation of application No. 09/607,799, filed on Jun. 30, 2002, now Pat. No. 6,464,716, which is a continuation-in-part of application No. 09/570,075, filed on May 12, 2000, now Pat. No. 6,471,717, and a continuation-in-part of application No. 09/215,041, filed on Dec. 16, 1998, now Pat. No. 6,254,626, and a continuation-in-part of application No. 09/103,342, filed on Jun. 23, 1998, now Pat. No. 6,096,068, and a continuation-in-part of application No. 09/052,545, filed on Mar. 31, 1998, now Pat. No. 6,231,595, and a continuation-in-part of application No. 09/047,012, filed on Mar. 24, 1998, now Pat. No. 5,957,963, and a continuation-in-part of application No. 10/161,107, filed on May 30, 2002, now Pat. No. 6,702,842, which is a continuation of application No. 09/607,799, filed on Jun. 30, 2000, now Pat. No. 6,464,716, which is a continuation-in-part of application No. 09/570,075, filed on May 12, 2000, now Pat. No. 6,471,717, and a continuation-in-part of application No. 09/215,041, filed on Dec. 16, 1998, now Pat. No. 6,254,626, and a continuation-in-part of application No. 09/103,342, filed on Jun. 23, 1998, now Pat. No. 6,096,068, and a continuation-in-part of application No. 09/052,545, filed on Mar. 31, 1998, now Pat. No. 6,231,595, and a continuation-in-part of application No. 09/047,012, filed on Mar. 24, 1998, now Pat. No. 5,957,963, and a continuation-in-part of application No. 09/012,287, filed on Jan. 23, 1998, now Pat. No. 6,051,019, and a continuation-in-part of application No. 10/158,406, filed on May 29, 2002, now Pat. No. 6,755,850, which is a continuation of application No. 09/650,940, filed on Aug. 30, 2000, now Pat. No. 6,482,226, which is a continuation of application No. 09/306,866, filed on May 7, 1999, now Pat. No. 6,235,048, which is a division of application No. 09/012,287, filed on Jan. 23, 1998, now Pat. No. 6,051,019, and a continuation-in-part of application No. 10/117,733, filed on Apr. 4, 2002, now Pat. No. 6,702,841, and a continuation-in-part of application No. 09/607,799, filed on Jun. 30, 2000, now Pat. No. 6,464,716, which is a continuation-in-part of application No. 09/215,041, filed on Dec. 16, 1998, now Pat. No. 6,254,626, and a continuation-in-part of application No. 09/379,295, filed on Aug. 23, 1999, now abandoned, which is a continuation-in-part of application No. 09/103,342, filed on Jun. 23, 1998, now Pat. No. 6,096,068, which is a continuation-in-part of application No. 09/047,012, filed on Mar. 24, 1998, now Pat. No. 5,957,963, which is a continuation-in-part of application No. 09/012,287, filed on Jan. 23, 1998, now Pat. No. 6,051,019, and a continuation-in-part of application No. 10/008,999, filed on Dec. 7, 2001, now Pat. No. 6,786,218, which is a continuation-in-part of application No. 09/373,112, filed on Aug. 11, 1999, and a continuation-in-part of application No. 09/103,342, filed on Jun. 23, 1998, now Pat. No. 6,096,068, which is a continuation-in-part of application No. 09/047,012, filed on Mar. 24, 1998, now Pat. No. 5,957,963, which is a continuation of application No. 09/103,342, filed on Jun. 23, 1998, now Pat. No. 6,096,068, and a continuation-in-part of application No. 09/908,642, filed on Jul. 18, 2001, and a continuation-in-part of application No. 09/834,068, filed on Apr. 12, 2001, now Pat. No. 6,692,488, which is a continuation of application No. 09/566,531, filed on May 8, 2000, now abandoned, which is a continuation of application No. 09/103,342, which is a continuation-in-part of application No. 09/047,012, filed on Mar. 24, 1998, now Pat. No. 5,957,963, which is a continuation-in-part of application No. 09/012,287, filed on Jan. 29, 1998, now Pat. No. 6,051,019, which is a continuation of application No. 09/052,545, filed on Mar. 31, 1998, now Pat. No. 6,231,595, and a continuation-in-part of application No. 09/785,243, filed on Feb. 16, 2001, now Pat. No. 6,818,011, which is a continuation of application No. 09/052,545, filed on Mar. 31, 1998, now Pat. No. 6,231,595, and a continuation-in-part of application No. 09/379,295, filed on Aug. 23, 1999, now abandoned, and a continuation-in-part of application No. 09/373,112, filed on Aug. 11, 1999, which is a continuation-in-part of application No. 09/292,532, filed on Apr. 15, 1999, now abandoned, and a continuation-in-part of application No. 09/103,342, filed on Jun. 23, 1998, now Pat. No. 6,096,068, and a continuation-in-part of application No. 09/052,545, filed on Mar. 31, 1998, now Pat. No. 6,231,595, and a continuation-in-part of application No. 09/047,012, filed on Mar. 24, 1998, now Pat. No. 5,957,963, and a continuation-in-part of application No. 09/012,287, filed on Jan. 23, 1998, now Pat. No. 6,051,019.

U.S. PATENT DOCUMENTS

| | | | | |
|---|---|---|---|---|
| 4,236,527 A | | 12/1980 | Newbower et al. | |
| 4,298,006 A | | 11/1981 | Parks | |
| 4,375,169 A | | 3/1983 | Torresin | |
| 4,532,414 A | | 7/1985 | Shah et al. | |
| 4,707,587 A | | 11/1987 | Greenblatt | |
| 4,739,492 A | | 4/1988 | Cochran | |
| 4,793,352 A | | 12/1988 | Eichenlaub | |
| 4,796,640 A | | 1/1989 | Webler | |
| 4,819,655 A | | 4/1989 | Webler | |
| 4,871,351 A | | 10/1989 | Feingold | |
| 4,894,164 A | | 1/1990 | Polaschegg | |
| 5,174,299 A | * | 12/1992 | Nelson | 600/505 |
| 5,241,951 A | | 9/1993 | Mason et al. | |
| 5,257,635 A | | 11/1993 | Langberg | |
| 5,257,977 A | * | 11/1993 | Eshel | 604/113 |
| 5,330,519 A | | 7/1994 | Mason et al. | |
| 5,391,142 A | | 2/1995 | Sites et al. | |
| 5,395,331 A | | 3/1995 | O'Neill et al. | |
| 5,403,281 A | | 4/1995 | O'Neill et al. | |
| 5,437,673 A | | 8/1995 | Baust et al. | |
| 5,531,776 A | | 7/1996 | Ward et al. | |
| 5,624,392 A | * | 4/1997 | Saab | 604/43 |
| 5,716,386 A | | 2/1998 | Ward et al. | |
| 5,733,319 A | | 3/1998 | Neilson et al. | |
| 5,741,248 A | | 4/1998 | Stern et al. | |
| 5,861,021 A | | 1/1999 | Thome et al. | |
| 5,891,094 A | | 4/1999 | Masterson et al. | |
| 5,906,614 A | | 5/1999 | Stern et al. | |
| 6,149,673 A | | 11/2000 | Ginsburg | |
| 6,149,676 A | | 11/2000 | Ginsburg | |
| 6,194,899 B1 | | 2/2001 | Ishihara et al. | |
| 6,231,594 B1 | | 5/2001 | Dae | |
| 6,235,019 B1 | * | 5/2001 | Lehmann et al. | 606/22 |
| 6,290,717 B1 | | 9/2001 | Philips | |
| 6,296,654 B1 | | 10/2001 | Ward | |
| 6,299,599 B1 | | 10/2001 | Pham et al. | |
| 6,303,156 B1 | | 10/2001 | Ferrigno | |
| 6,312,452 B1 | | 11/2001 | Dobak, III et al. | |
| 6,336,911 B1 | | 1/2002 | Westerbeck | |
| 6,602,243 B2 | | 8/2003 | Noda | |
| 6,620,188 B1 | * | 9/2003 | Ginsburg et al. | 607/106 |
| 6,679,906 B2 | | 1/2004 | Hammack et al. | |
| 6,695,874 B2 | * | 2/2004 | Machold et al. | 607/106 |
| 6,702,839 B1 | | 3/2004 | Dae et al. | |
| 2001/0002442 A1 | | 5/2001 | Dobak, III | |
| 2001/0014802 A1 | | 8/2001 | Tu | |
| 2001/0029394 A1 | | 10/2001 | Dobak, III et al. | |
| 2001/0045104 A1 | | 11/2001 | Bailey, Sr. et al. | |
| 2002/0007203 A1 | | 1/2002 | Gilmartin et al. | |
| 2002/0032473 A1 | | 3/2002 | Kushnir et al. | |
| 2002/0068877 A1 | | 6/2002 | Abramovitch et al. | |
| 2002/0077680 A1 | | 6/2002 | Noda | |
| 2002/0103519 A1 | | 8/2002 | Dobak, III et al. | |
| 2002/0111657 A1 | | 8/2002 | Dae et al. | |
| 2002/0193854 A1 | | 12/2002 | Dobak, III et al. | |
| 2003/0014094 A1 | | 1/2003 | Hammack et al. | |
| 2003/0060863 A1 | | 3/2003 | Dobak, III et al. | |
| 2003/0088299 A1 | | 5/2003 | Magers et al. | |
| 2003/0092975 A1 | | 5/2003 | Casscells, III et al. | |
| 2003/0114835 A1 | | 6/2003 | Noda | |
| 2003/0114903 A1 | | 6/2003 | Ellingboe | |
| 2004/0030259 A1 | | 2/2004 | Dae et al. | |
| 2004/0087606 A1 | | 5/2004 | Voorhees | |
| 2004/0116987 A1 | | 6/2004 | Magers et al. | |
| 2004/0116988 A1 | | 6/2004 | Hammack et al. | |
| 2004/0162520 A1 | | 8/2004 | Noda et al. | |
| 2004/0176672 A1 | | 9/2004 | Silver et al. | |

FOREIGN PATENT DOCUMENTS

| | | |
|---|---|---|
| EP | 0696176 B1 | 7/2002 |
| WO | WO 00/57823 | 10/2000 |
| WO | WO 01/03606 | 1/2001 |
| WO | WO 01/10323 | 2/2001 |

| WO | WO 01/87174 | 11/2001 |
| WO | WO 02/19934 | 3/2002 |
| WO | WO 02/47742 | 6/2002 |
| WO | WO 03/006085 | 1/2003 |
| WO | WO 03/015673 | 2/2003 |
| WO | WO 2004/015382 | 2/2004 |
| WO | WO 2004/075949 | 9/2004 |

OTHER PUBLICATIONS

Babbs, Charles F. et al.; "Theoretical Basis for Controlling Minimal Tumor Temperature During Interstitial Conductive Heat Therapy"; IEEE Transactions on Biomedical Engineering, Vo. 37, No. 7; pp. 662-672 (Jul. 1990).

Behmann, F.W., et al.; "Heat Generation Control during Artificial Hypothermia: I: Experimental Examination of the Influence of Anesthetic Depth" Pflügers Archiv, Bd. 266, S. 408-421 (1958) (German article with English translation).

Behmann, F.W; "Heat Generation Control during Artificial Hypothermia: II. Theoretical Examinations"; Pflügers Archiv, Bd. 266, S. 422-446 (1958) (German Article with English translation).

Behmann, F.W.; "Regulation of heat production in experimental hypothermia of homothermal animals"; Naunyn Schmiedebergs Arch Exp Pathol Pharmakol; 228 (1-2): 126-128 (1956). (German article with English translation).

Behmann, F.W.; "Heat Generation Control during Artificial Hypothermia, an article about the economic problem of trembling stages"; Pflügers Archive, vol. 263, pp. 166-187 (1956) German article with English translation).

Behmann, F.W., et al.; "Intravascular Cooling, a Method to Achieve Controllable Hypothermia"; Pflügers Archive, vol. 263, pp. 145-165 (1956) (German article with English translation).

Benzinger, T.H.; "On Physical Heat Regulation and Sense of Temperature in Man"; Proc. N.A.S.; Physiology; vol. 45; pp. 645-659 (1959).

Benzinger MD, Maria; "Tympanic thermometry in surgery and anesthesia"; JAMA; vol. 209, No. 8; pp. 1207-1211 (Aug. 25, 1969).

Bone, M.E. et al.; "Bladder Temperature as an Estimate of Body Temperature During Cardiopulmonary Bypass"; Anaesthesia; vol. 43, pp. 181-185 (1988).

Cabanac, M; "Selective Brain Cooling and Thermoregulatory Set-Point"; Journal of Basic & Clinical Physiology & Pharmacology; vol. 9, No. 1, pp. 3-13 (1998).

Carroll, Diane L., et al.; "A comparison of measurements from a temporal artery thermometer and a pulmonary artery thermistor—preliminary results"; available at http://pcs.mgh.harvard.edu/CCPD/Nursing_Research/Research_Abstracts_2003.asp#temporal.

Dallas, W. Gordon; "Gorman-Rupp Hypothermia Machine"; Health Devices (Nov. 1971-Apr. 1972).

DeFord, J. A. et al.; "Design and Evaluation of Closed-Loop Feedback Control of Minimum Temperatures in Human Intracranial Tumours Treated with Interstitial Hyperthermia"; Med. & Biol. Eng. & Comput.; vol. 29; pp. 197-206 (Mar. 1991).

Fulbrook, Paul; "Core Body Temperature Measurement: A Comparison of Axilla, Tympanic Membrane and Pulmonary Artery Blood Temperature"; Intensive and Critical Care Nursing; vol. 13; pp. 266-272 (1997).

Gentilello MD, L.M.; "Advances in the Management of Hypothermia"; Surgical Clinics of North America; vol. 75, No. 2; pp. 243-257 (Apr. 1995).

Gerbrandy et al.; "Oral, Rectal, and Esophageal Temperatures in Relation to Central Temperature Control in Man"; Clin Sci (Lond); vol. 13, No. 4: pp. 615-624. (Nov. 1954).

Haley, et al.; "A Randomized Tirilazad Mesylate in Patients with Acute Stroke (RANTTAS). The RANTTAS Investigators"; Stroke; vol. 27, No. 9; pp. 1453-1458 (1996).

Hayes, B., et al.; "Temperature Control in Extracorporeal Circulation"; Br Med J. Aug. 17, 1968;2(615):430.

Hederer, G., et al.; "Animal Experiment Observations Regarding Cardiac Surgery under Intravascular Hypothermia"; Labgebbecjs Arch. U. Dtsch. A. Chir., Bd. 283, S. 601-625 (1957) (German article with English translation).

Hills, Gordon A., et al.; "Apparatus For Controlling Temperature of Catheter Contents in Cold Environments"; Laboratory Animal Science; vol. 27, No. 6; pp. 1028-1030 (Dec. 1977).

Holzman, Steven, et al.; "The Effect of In-Line Microwave Energy on Blood: A Potential Modality for Blood Warming"; Journal of Trauma; vol. 33, No. 1; pp. 89-94 (Jul. 1992).

Jackson, Donald, et al; "Hypothermia : IV. Study of Hypothermia Induction Time with Various Pharmacological Agents (24617)"; Proc Soc Exp Biol Med.; 100(2): 332-335 (Feb. 1959).

Kinney, Thomas B, et al.; "Optimizing Myocardial Hypothermia: I. Temperature Probe Design and Clinical Inferences"; Ann Thorac Surg; vol. 51; pp. 278-283 (1991).

Lacis, A.T., et al.; "A Device for Surface Cooling and Rewarming in Operations on the "Dry" Heart in Babies and Children During Moderate, Deep and Profound Hypothermia" Aust. N.Z. J. Surg.; vol. 46, No. 1; pp. 29-31 (Feb. 1976).

Matsukawa, T. et al.; "Comparison of Distal Oesophageal Temperature with "Deep" and Tracheal Temperatures"; Can J. Anaesth; vol. 44, No. 4; pp. 433-438 (1997).

McWilliams, Roger; "Gorman-Rupp Hypothermia Machine"; Gorman-Rupp Industries Division; Health Devices; pp. 263-265 (Jul.-Aug. 1972).

Moller, P. H. et al.; "Temperature Control and Light Penetration in a Feedback Interstitial Laser Thermotherapy System"; Int. J. Hyperthermia; vol. 12, No. 1; pp. 49-63 (Jan. 1996).

Mora, C.T., et al.; "The Effect of Temperature Management During Cardiopulmonary Bypass on Neuropsychologic Outcomes in Patients Undergoing Coronary Revascularization"; The Journal of Thoracic and Cardiovascular Surgery; vol. 112, No. 2; pp. 514-522 (1996).

Olshausen, K. et al.; "An Isothermal Flow Meter with Improved Frequency Response for Measuring Tissue Blood Flow"; Pflügers Archive; vol. 367; pp. 97-102 (1976).

Shiraki, K., et al.; "Esophageal and Tympanic Temperature Responses to Core Blood Temperature Changes During Hyperthermia"; J Appl Physiol.; vol. 61, No. 1; pp. 98-102 (1986).

TE Technology, Inc.; "TE technology/Temperature Controllers" (Dec. 19, 2000) available at: http://www.tetech.com/temp/tc24-25.html.

Dallas, W. Gordon; "Gorman-Rupp Hypothermia Machine"; Health Devices (Nov. 1971-Apr. 1972), pp. 190-191.

Iyodenshi To Seitai Kogaku; "Sensor Technology to Control Artificial Organs" (in Japanese); vol. 22, No. 4; pp. 295-300 (Aug. 1984).

* cited by examiner

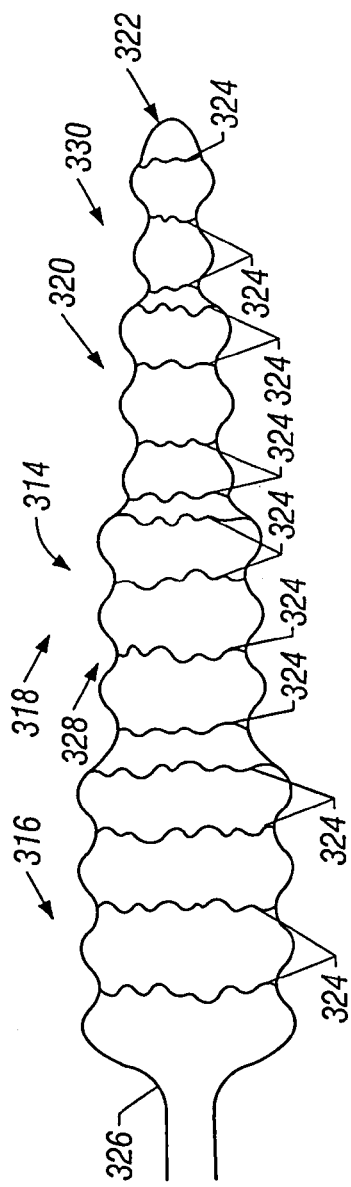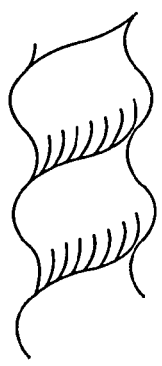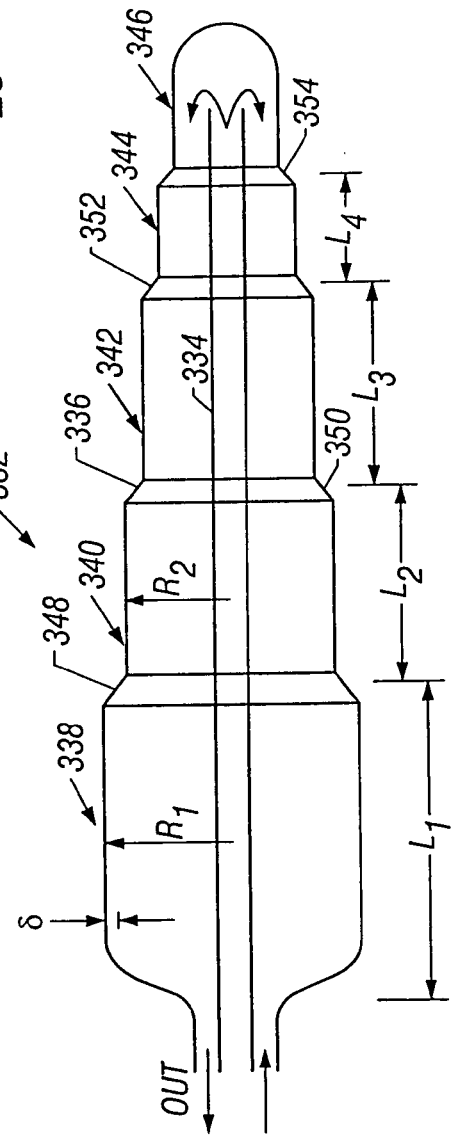
FIG. 22
FIG. 23
FIG. 24

SYSTEM AND METHOD FOR INDUCING HYPOTHERMIA WITH ACTIVE PATIENT TEMPERATURE CONTROL EMPLOYING CATHETER-MOUNTED TEMPERATURE SENSOR AND TEMPERATURE PROJECTION ALGORITHM

CONTINUING INFORMATION

This application claims the benefit of priority of U.S. Provisional Application No. 60/449,803, flied Feb. 24, 2003 and 60/449,809, filed Feb. 24, 2003 and 60/456,137 filed Mar. 20, 2003 and 60/504,145 filed Sep. 17, 2003.

This application is a continuation-in-part of:

1- U.S. application Ser. No. 10/158,406, filed May 29, 2002, U.S. Pat. No. 6,755,850 which is a continuation of U.S. application Ser. No. 09/650,940, filed Aug. 30, 2000, U.S.Pat. No. 6,482,226, which is a continuation of U.S. application Ser. No. 09/306,866, filed May 7, 1999, U.S. Pat. No. 6,235,048, which is a divisional application of U.S. application Ser. No. 09/012,287, filed Jan. 23, 1998, U.S. Pat. No. 6,051,019;

2- this application is also a continuation-in-part of U.S. application Ser. No. 09/785,243, filed Feb. 16, 2001, U.S. Pat. No. 6,818,011, which is a continuation of U.S. application Ser. No. 09/052,545, filed Mar. 31, 1998, U.S. Pat. No. 6,231,595;

3- this application is also a continuation-in-part of U.S. application Ser. No. 09/834,068, filed Apr. 12, 2001, U.S. Pat. No. 6,692,488, which is a continuation of U.S. application Ser. No. 09/566,531, filed May 8, 2000, now abandoned, which is a continuation of U.S. application Ser. No. 09/103,342, filed Jun. 23, 1998, U.S. Pat. No. 6,096,068, which is a continuation-in-part of U.S. application Ser. No. 09/047,012, filed on Mar. 24, 1998, U.S. Pat. No. 5,957,963, which is a continuation-in-part of U.S. Application Ser. No. 09/012,287, filed Jan. 23, 1998, U.S. Pat. No. 6,051,019 and a continuation of U.S. application Ser. No. 09/785,243, filed Feb. 16, 2001, U.S. Pat. No. 6,818,011 which is a continuation of U.S. application Ser. No. 09/052,545, Mar. 31, 1998, U.S. Pat. No. 6,231,595;

4- this application is also a continuation-in-part of U.S. application Ser. No. 10/714,070, filed Nov. 14, 2003, now abandoned which is a continuation of U.S. application Ser. No. 10/095,753, filed on Mar. 11, 2002, U.S. Pat. No. 6,695,873, which is a divisional application of U.S. application Ser. No. 09/757,124, filed on Jan. 8, 2001, U.S. Pat. No. 6,540,771, which is a divisional of U.S. application 09/215,038 filed on Dec. 16, 1998, U.S. Pat. No. 6,261,312, which is a continuation-in-part of U.S. application Ser No. 09/103,342 filed on Jun. 23, 1998, U.S. Pat. No. 6,096,068, which is a continuation-in-part of U.S. Application Ser. No. 09/047,012 filed on Mar. 24, 1998, U.S. Pat. No. 5,957,963, which is a continuation-in-part of U.S. application Ser No. 09/012,287 filed on Jan. 23, 1998, U.S. Pat. No. 6,051,019;

5- this application is also a continuation-in-part of U.S. application Ser. No. 10/322,337, filed Dec. 16, 2002, U.S. Pat. No. 6,740,109, which is a continuation of co-pending U.S. application Ser. No. 09/292,532, filed Apr. 15, 1999, now abandoned, which is a continuation-in-part of U.S. application Ser. No. 09/103,342, filed on Jun. 23, 1998, U.S. Pat. No. 6,096,068 and a continuation-in-part of U.S. application Ser. No. 09/052,545, filed Mar. 31, 1998, U.S. Pat. No. 6,231,595 and a continuation-in-part of U.S. application Ser. No. 09/047,012, filed on Mar. 24, 1998, U.S. Pat. No. 5,957,963;

6- this application is also a continuation-in-part of U.S. application Ser. No. 09/379,295, filed Aug. 23, 1999, now abandoned;

7- this application is also a continuation-in-part of co-pending U.S. application Ser. No. 10/716,801, filed Nov 18, 2003, now U.S. Pat. No. 7,052,508 which is a continuation of U.S. application Ser. No. 09/414,184, filed Oct. 7, 1999, U.S. Pat. No. 6,325,818;

8- this application is also a continuation-in-part of U.S. application Ser. No. 10/210,819, filed Jul. 31, 2002, U.S. Pat. No. 6,679,907, which is a continuation of U.S. application Ser. No. 09/246,788 filed Feb. 9, 1999, U.S. Pat. No. 6,491,716, which is a continuation-in-part of U.S. application Ser. No. 09/103,342, filed Jun. 23, 1998, U.S, Pat. No. 6,096,088 and a continuation-in-part of U.S. application Ser. No. 09/052,545, filed Mar. 31, 1998, U.S. Pat. No. 6,231,595 and a continuation-in-part of U.S. application Ser. No. 09/047,012, filed Mar. 24, 1998, U.S. Pat. No. 5,957,963 and a continuation-in-part of U.S. application Ser. No. 09/215,038, filed Dec. 16, 1998, U.S. Pat. No. 6,261,312 and a continuation-in-part of U.S. application Ser. No. 09/215,039, filed on Dec. 16, 1998, U.S. Pat. No. 6,251,129 and a continuation-in-part of U.S. application Ser. No. 09/232,177, filed on Jan. 15, 1999, U.S. Pat. No. 6,245,095;

9- this application is also a continuation-in-part of co-pending U.S. application Ser. No. 09/908,642, filed Jul. 18, 2001;

10- this application is also a continuation-in-part of U.S. application Ser. No. 10/161,107, filed May 30, 2002, U.S. Pat. No. 6,702,842, which is a continuation of U.S. application Ser. No. 09/607,799, filed Jun. 30, 2000, U.S. Pat. No. 6,464,716, which is a continuation-in-part of U.S. application Ser. No. 09/570,075, filed May 12, 2000, U.S. Pat. No. 6,471,717 and a continuation-in-part of U.S. application Ser. No. 09/215,041, filed Dec. 16, 1998, U.S. Pat. No. 6,254,626 and a continuation-in-part of U.S. application Ser. No. 09/103,342, filed Jun. 23, 1998, U.S. Pat. No. 6,096,068 and a continuation-in-part of U.S. application Ser. No. 09/052,545, filed Mar. 31, 1998, U.S. Pat. No. 6,231,595 and a continuation-in-part of U.S. patent application Ser. No. 09/047,012, filed Mar. 24, 1998, U.S. Pat. No. 5,957,963 and a continuation-in-part of U.S. application Ser. No. 09/012,287, filed Jan. 23, 1998, U.S. Pat. No. 6,051,019;

11- this application is also a continuation-in-part of co-pending U.S. application Ser. No. 10/729,526, filed Dec. 5, 2003, now U.S. Pat. No. 7,211,105 which is continuation of U.S. application Ser. No. 10/082,964, filed Feb. 25, 2002, U.S. Pat. No. 6,660,028 which is a continuation of U.S. application Ser. No. 09/586,000, filed Jun. 2, 2000, U.S. Pat. No. 6,383,210;

12- this application is also a continuation-in-part of U.S. application Ser. No. 10/008,999, filed Dec. 7, 2001, U.S. Pat. No. 6,786,218, which is a continuation-in-part of co-pending U.S. application Ser. No. 09/373,112 filed Aug. 11, 1999 and a continuation-in-part of U.S. application Ser. No. 09/103,342 filed Jun. 23, 1998, U.S. Pat. No. 6,096,068, which is a continuation-in-part of U.S. application Ser. No. 09/047,012 filed Mar. 24, 1998, U.S. Pat. No. 5,957.963;

13- this application is also a continuation-in-part of co-pending U.S. application Ser. No. 09/373,112, filed Aug. 11, 1999, which is a Continuation-in-part of 09/292,532, filed Apr. 15, 1999 now abandoned, and a Continuation-in-part of U.S. application Ser. No. 09/103,342 filed Jun. 23, 1998, U.S. Pat. No. 6,096,068 and a Continuation-in-part of U.S. application Ser. No 09/052,545 filed Mar. 31, 1998, U.S. Pat. No. 6,231,595 and a Continuation-in-part of U.S. application Ser. No. 09/047,012 filed Mar 24, 1998, U.S. Pat. No. 5,957,963 and a Continuation-in-part of U.S. application Ser. No. 09/012,287 filed Jan. 23, 1998, U.S. Pat. No. 6,051,019;

14- this application is also a continuation-in-part of U.S. application Ser. No. 10/007,545, filed Nov. 6, 2001, U.S. Pat. No. 6,719,779, which claims the benefit of priority to U.S. Provisional application No. 60/247,203, filed Nov. 7, 2000;

15- this application is also a continuation-in-part of co-pending U.S. application Ser. No. 10/411,001, filed Apr. 9, 2003, now U.S. Pat. No. 7,094,253 which is a continuation of U.S. application Ser. No. 10/005,416 filed Nov. 7, 2001, U.S. Pat. No. 6,585,752, which claims the benefit of priority to U.S. Provisional Application No. 60/246,620, filed Nov. 7, 2000 and is a continuation-in-part U.S. application Ser. No. 09/586,000, filed Jun. 2, 2000, U.S. Pat. No. 6,383,210 and U.S. application Ser. No. 09/566,531, filed May 8, 2000, now abandoned, which is a continuation of U.S. application Ser. No. 09/103,342, filed Jun. 23, 1998, U.S. Pat. No. 6,096,068, which is a continuation-in-part of U.S. application Ser. No. 09/047,012, filed Mar. 24, 1998, U.S. Pat. No. 5,957,963, which is a continuation-in-part of U.S. application Ser. No. 09/012,287, filed Jan. 23, 1998, U.S. Pat. No. 6,051,019;

16- this application is also a continuation-in-part of U.S. application Ser. No. 10/117,733, filed Apr. 4, 2002, U.S. Pat. No. 6,702,841, which claims priority to U.S. Provisional Patent Application No. 60/281,771, filed Apr. 5, 2001, and is a continuation-in-part of U.S. application Ser. No. 09/607,799, filed Jun. 30, 2000, U.S. Pat. No. 6,464,716, which is a continuation-in-part of U.S. application Ser. No. 09/215,041, filed Dec. 16, 1998, U.S. Pat. No. 6,254,626 and a continuation-in-part of U.S. application Ser. No. 09/379,295, filed Aug. 23, 1999, now abandoned, which is a continuation-in-part of U.S. application Ser. No. 09/103,342, filed Jun. 23, 1998, U.S. Pat. No. 6,096,068, which is a continuation-in-part of U.S. application Ser. No. 09/047,012, filed Mar. 24, 1998, U.S. Pat. No. 5,957,963, which is a continuation-in-part of U.S. application Ser. No. 09/012,287, filed Jan. 23, 1998, U.S. Pat. No. 6,051,019;

17- this application is also a continuation-in-part of co-pending U.S. application Ser. No. 10/219,874, filed Aug. 14, 2002, which claims the benefit of priority of U.S. Provisional Application No. 60/311,589, filed Aug. 9, 2001 and the benefit of priority U.S. Provisional Application No. 60/312,409, filed Aug. 15, 2001 and the benefit of priority U.S. Provisional Application No. 60/316,057, filed Aug. 29, 2001 and the benefit of priority U.S. Provisional Application No. 60/316,922, filed Aug. 31, 2001 and the benefit of priority U.S. Provisional Application No. 60/322,945; filed Sep. 14, 2001 and is a continuation-in-part of U.S. application Ser. No. 09/650,940, filed Aug. 30, 2000, U.S. Pat. No. 6,482,226 and a continuation-in-part of U.S. application Ser. No. 09/785,243, filed Feb. 16, 2001, U.S. Pat. No. 6,818,011 and a continuation-in-part of U.S. application Ser. No. 09/566,531, filed on May 8, 2000, now abandoned and a continuation-in-part of U.S. application Ser. No. 09/757,124, filed Jan. 8, 2001, U.S. Pat. No. 6,540,771 and a continuation-in-part of U.S. application Ser. No. 09/714,749, filed on Nov. 16, 2000, U.S. Pat. No. 6,468,296 and a continuation-in-part of U.S. application Ser. No. 09/621,051, filed on Jul. 21, 2000, U.S. Pat. No. 6,582,455 and a continuation-in-part of U.S. application Ser. No. 09/800,159, filed on Mar. 6, 2001, now abandoned, and a continuation-in-part of U.S. application Ser. No. 09/292,532 filed on Apr. 15, 1999, now abandoned, and a continuation-in-part of U.S. application Ser. No. 09/379,295, filed on Aug. 23, 1999, now abandoned, and a continuation-in-part of U.S. application Ser. No. 09/885,655, filed on Jun. 20, 2001, U.S. Pat. No. 6,676,680 and a continuation-in-part of U.S. application Ser. No. 09/246,788, filed Mar. 28, 2001, U.S. Pat. No. 6,491,716 and a continuation-in-part of U.S. application Ser. No. 09/797,028, filed on Feb. 27, 2001, now abandoned, and a continuation-in-part of U.S. application Ser. No. 09/607,799, filed on Jun. 30, 2000, U.S. Pat. No. 6,464,716 and a continuation-in-part of U.S. application Ser. No. 09/519,022, filed on Mar. 3, 2000, U.S. Pat. No. 6,379,378 and a continuation-in-part of U.S. application Ser. No. 10/082,964, filed on Feb. 25, 2002, U.S. Pat. No. 6,660,028 and a continuation-in-part of U.S. application Ser. No. 09/539,932, filed on Mar. 31, 2000, U.S. Pat. No. 6,491,039 and a continuation-in-part of U.S. application Ser. No. 09/658,950, filed on Sep. 11, 2000, now abandoned, and a continuation-in-part of co-pending U.S. application Ser. No 09/373,112, filed on Aug. 11, 1999 and a continuation-in-part of U.S. application Ser. No. 10/007,545, filed on Nov. 6, 2001, U.S. Pat. No. 6,719,779 and a continuation-in-part of U.S. application Ser. No. 10/005,416, filed on Nov. 7, 2001, U.S. Pat. No. 6,585.752 and a continuation-in-part of U.S. application Ser. No. 10/117,733, filed Apr. 4, 2002, U.S. Pat. No. 6,702,841; all of the above are incorporated by reference herein in their entirety.

FIELD OF THE INVENTION

The present invention relates generally to the lowering, raising, and control of the temperature of the human body. More particularly, the invention relates to a method and intravascular apparatus for controlling the temperature of the human body.

BACKGROUND

Background Information—Organs in the human body, such as the brain, kidney and heart, are maintained at a constant temperature of approximately 37° C. Hypothermia can be clinically defined as a core body temperature of 35° C. or less. Hypothermia is sometimes characterized further according to its severity. A body core temperature in the range of 33° C. to 35° C. is described as mild hypothermia. A body temperature of 28° C. to 32° C. is described as moderate hypothermia. A body core temperature in the range of 24° C. to 28° C. is described as severe hypothermia.

Hypothermia is uniquely effective in reducing ischemia. For example, it is effective in reducing brain injury caused by a variety of neurological insults and may eventually play an important role in emergency brain resuscitation. Experimental evidence has demonstrated that cerebral cooling improves outcome after global ischemia, focal ischemia, or traumatic brain injury. For this reason, hypothermia may be induced in order to reduce the effect of certain bodily injuries to the brain as well as ischemic injuries to other organs.

BRIEF DESCRIPTION OF THE DRAWINGS

The novel features of this invention, as well as the invention itself, will be best understood from the attached drawings, taken along with the following description, in which similar reference characters refer to similar parts, and in which:

FIG. 22 illustrates a turbulence-inducing heat transfer element according to a second alternative embodiment of the invention employing a surface area enhancing taper and turbulence-inducing surface features;

FIG. 23 illustrates a spiral type of turbulence-inducing surface feature which may be employed in the heat transfer element of the embodiment of FIG. 22;

FIG. 24 illustrates a heat transfer element according to an alternative embodiment of the invention employing a surface area enhancing taper;

DETAILED DESCRIPTION

Overview

In the following description, the term "pressure communication" is used to describe a situation between two points in a flow or in a standing or flowing fluid. If pressure is applied at one point, the second point will eventually feel effects of the pressure if the two points are in pressure communication. Any number of valves or elements may be disposed between the two points, and the two points may still be in pressure communication if the above test is met. For example, for a standing fluid in a pipe, any number of pipe fittings may be disposed between two pipes and, so long as an open path is maintained, points in the respective pipes may still be in pressure communication.

A device may be employed to intravascularly lower the temperature of a body in order to cause therapeutic hypothermia. A cooling element may be placed in a high-flow vein such as the vena cavae to absorb heat from the blood flowing into the heart. This transfer of heat causes a cooling of the blood flowing through the heart and thus throughout the vasculature. Such a method and device may therapeutically be used to induce, and reverse, an artificial state of hypothermia.

A heat transfer element that systemically cools blood should be capable of providing the necessary heat transfer rate to produce the desired cooling effect throughout the vasculature. This may be up to or greater than 300 watts, and is at least partially dependent on the mass of the patient and the rate of blood flow. Surface features may be employed on the heat transfer element or as part of the heat transfer element to enhance the heat transfer rate. The surface features and other components of the heat transfer element are described in more detail below.

One problem with hypothermia as a therapy is that the patient's thermoregulatory defenses initiate, attempting to defeat the hypothermia. Methods and devices may be used to lessen the thermoregulatory response. For example, a heating blanket may cover the patient. In this way, the patient may be made more comfortable. Thermoregulatory drugs may also be employed to lower the trigger point at which the patient's thermoregulatory system begins to initiate defenses. Such drugs are described in more detail below. A method employing thermoregulatory drugs, heating blankets, and heat transfer elements is also disclosed below.

Anatomical Placement

Figure 1:
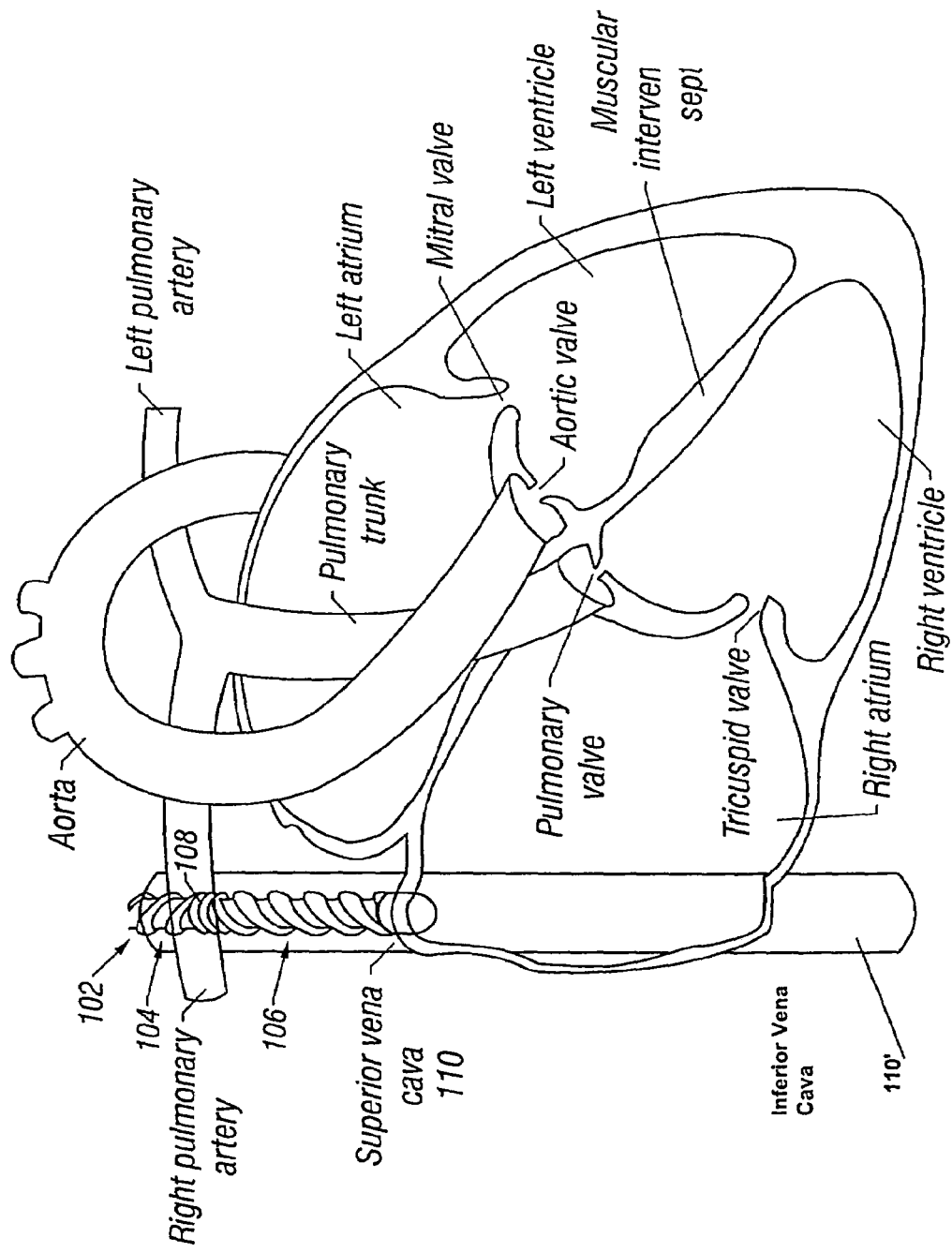
FIG. 1 is a schematic representation of the heat transfer element being used in an embodiment within the superior vena cava.

The internal jugular vein is the vein that directly drains the brain. The external jugular joins the internal jugular at the base of the neck. The internal jugular veins join the subclavian veins to form the brachiocephalic veins that in turn drain into the superior vena cava. The superior vena cava drains into the right atrium of the heart as may be seen by referring ahead to FIG. 1. The superior vena cava supplies blood to the heart from the upper part of the body.

A cooling element 102 may be placed into the superior vena cava 110, inferior vena cava 110', or otherwise into a vein which feeds into the superior vena cava, inferior vena cava, or otherwise into the heart to cool the body. A physician percutaneously places the catheter into the subclavian or internal or external jugular veins to access the superior vena cava. A physician percutaneously places the catheter into the femoral vein to access the inferior vena cava. The blood, cooled by the heat transfer element, may be processed by the heart and provided to the body in oxygenated form to be used as a conductive medium to cool the body. The lungs have a fairly low heat capacity, and thus the lungs do not cause appreciable rewarming of the flowing blood.

Heat Transfer

When a heat transfer element is inserted into an artery or vein, the primary mechanism of heat transfer between the surface of the heat transfer element and the blood is forced convection. Convection relies upon the movement of fluid to transfer heat. Forced convection results when an external force causes motion within the fluid. In the case of arterial or venous flow, the beating heart causes the motion of the blood around the heat transfer element. The magnitude of the heat transfer rate is proportional to the surface area of the heat transfer element, the temperature differential, and the heat transfer coefficient of the heat transfer element.

The receiving artery or vein into which the heat transfer element is placed has a limited diameter and length. Thus, the surface area of the heat transfer element must be limited to avoid significant obstruction of the artery or vein and to allow the heat transfer element to easily pass through the vascular system. For placement within the superior vena cava via the external jugular, the cross sectional diameter of the heat transfer element may be limited to about 5-6 mm, and its length may be limited to approximately 10-15 cm. For placement within the inferior vena cava, the cross sectional diameter of the heat transfer element may be limited to about 6-7 mm, and its length may be limited to approximately 25-35 cm.

Decreasing the surface temperature of the heat transfer element can increase the temperature differential. However, the minimum allowable surface temperature is limited by the characteristics of blood. Blood freezes at approximately 0° C. When the blood approaches freezing, ice emboli may form in the blood, which may lodge downstream, causing serious ischemic injury. Furthermore, reducing the temperature of the blood also increases its viscosity, which results in a small decrease in the value of the convection heat transfer coefficient. In addition, increased viscosity of the blood may result in an increase in the pressure drop within the vessel, thus compromising the flow of blood to the brain. Given the above constraints, it may be advantageous to limit the minimum allowable surface temperature of the cooling element to approximately 5° C. This results in a maximum temperature differential between the blood stream and the cooling element of approximately 32° C. For other physiological reasons, there are limits on the maximum allowable surface temperature of the warming element.

The mechanisms by which the value of the convection heat transfer coefficient may be increased are complex. However, it is well known that the convection heat transfer coefficient increases with the level of "mixing" or "turbulent" kinetic energy in the fluid flow. Thus it may be advantageous to have blood flow with a high degree of mixing in contact with the heat transfer element.

The blood flow has a considerably more stable flux in the superior or inferior vena cava than in an artery. However, the blood flow in the superior vena cava still has a high degree of inherent mixing or turbulence. Reynolds numbers in the superior vena cava may range, for example, from 2,000 to 5,000. Thus, blood cooling in the vena cava may benefit from enhancing the level of mixing with the heat transfer element but this benefit may be substantially less than that caused by the inherent mixing.

A thin boundary layer has been shown to form during the cardiac cycle. Boundary layers develop adjacent to the heat transfer element as well as next to the walls of the artery or vein. Each of these boundary layers has approximately the same thickness as the boundary layer that would have developed at the wall of the artery in the absence of the heat transfer element. The free stream flow region is developed in an annular ring around the heat transfer element. The heat transfer element used in such a vessel should reduce the formation of such viscous boundary layers.

Heat Transfer Element Characteristics

The intravascular heat transfer element should be flexible in order to be placed within the vena cavae or other veins or arteries. The flexibility of the heat transfer element is an important characteristic because the same is typically inserted into a vein such as the external jugular and accesses the superior vena cava by initially passing though a series of one or more branches. Further, the heat transfer element is ideally constructed from a highly thermally conductive material such as metal or a thin polymer or a doped polymer in order to facilitate heat transfer. The use of a highly thermally conductive material increases the heat transfer rate for a given temperature differential between the working fluid within the heat transfer element and the blood. This facilitates the use of a higher temperature coolant, or lower temperature warming fluid, within the heat transfer element, allowing safer working fluids, such as water or saline, to be used. Highly thermally conductive materials, such as metals, tend to be rigid. Therefore, the design of the heat transfer element should facilitate flexibility in an inherently inflexible material.

It is estimated that the cooling element should absorb at least about 300 Watts of heat when placed in the superior vena cava to lower the temperature of the body to between about 30° C. and 34° C. These temperatures are thought to be appropriate to obtain the benefits of hypothermia described above. The power removed determines how quickly the target temperature can be reached. For example, in a stroke therapy in which it is desired to lower brain temperature, the same may be lowered about 4° C. per hour in a 70 kg human upon removal of 300 Watts.

One embodiment of the invention uses a modular design. This design creates helical blood flow and produces a level of mixing in the blood flow by periodically forcing abrupt changes in the direction of the helical blood flow. The abrupt changes in flow direction are achieved through the use of a series of two or more heat transfer segments, each including one or more helical ridges. The use of periodic abrupt changes in the helical direction of the blood flow in order to induce strong free stream turbulence may be illustrated with reference to a common clothes washing machine. The rotor of a washing machine spins initially in one direction causing laminar flow. When the rotor abruptly reverses direction, significant turbulent kinetic energy is created within the entire washbasin as the changing currents cause random turbulent motion within the clothes-water slurry. These surface features also tend to increase the surface area of the heat transfer element, further enhancing heat transfer.

A heat transfer element with a smooth exterior surface may be able to provide the desired amount of heat transfer. However, as noted above, it is well known that the convection heat transfer coefficient increases with the level of turbulent kinetic energy in the fluid flow. Thus, if flow past a smooth heat transfer element will not transfer sufficient heat, it is advantageous to have turbulent or otherwise mixed blood flow in contact with the heat transfer element.

As noted above, the helical designs create helical blood flow and produce a high level of mixing in the free stream. For a swirling flow in a tube in which the azimuthal velocity of the fluid vanishes toward the stationary outer boundary, any non-vanishing azimuthal velocity in the interior of the flow will result in an instability in which the inner fluid is spontaneously exchanged with fluid near the wall, analogous to Taylor cells in the purely azimuthal flow between a rotating inner cylinder and stationary outer cylinder. This instability results from the lack of any force in opposition to the centripetal acceleration of the fluid particles moving along helical paths, the pressure in the tube being a function only of longitudinal position.

In one embodiment, the device of the present invention imparts an azimuthal velocity to the interior of a developed pipe flow, with the net result being a continuous exchange of fluid between the core and perimeter of the flow as it moves longitudinally down the pipe. This fluid exchange enhances the transport of heat, effectively increasing the convective heat transfer coefficient over that which would have obtained in undisturbed pipe flow. This bulk exchange of fluid is not necessarily turbulent, although turbulence is possible if the induced azimuthal velocity is sufficiently high.

Figure 2:
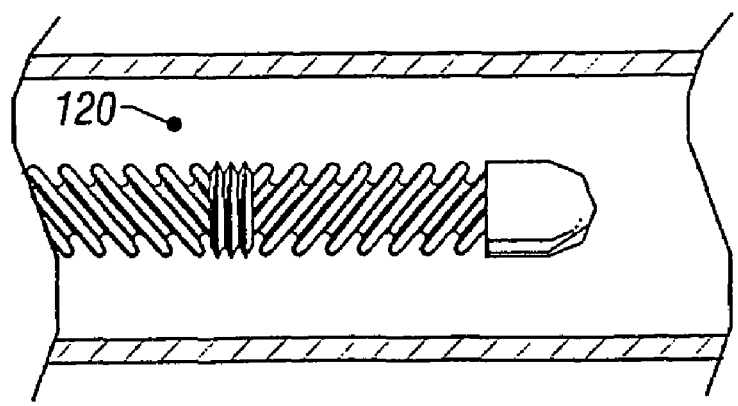
FIG. 2 is an elevational view of a mixing inducing heat transfer element within a blood vessel.

FIG. 2 is a perspective view of a mixing-inducing heat transfer element within an artery or vein. In this embodiment, turbulence or mixing is further enhanced by periodically forcing abrupt changes in the direction of the helical blood flow. Turbulent or mixed flow would be found at point 120, in the free stream area. The abrupt changes in flow direction are achieved through the use of a series of two or more heat transfer segments, each comprised of one or more helical ridges. Ideally, the segments will be close enough together to prevent re-laminarization of the flow in between segments.

Figure 3:
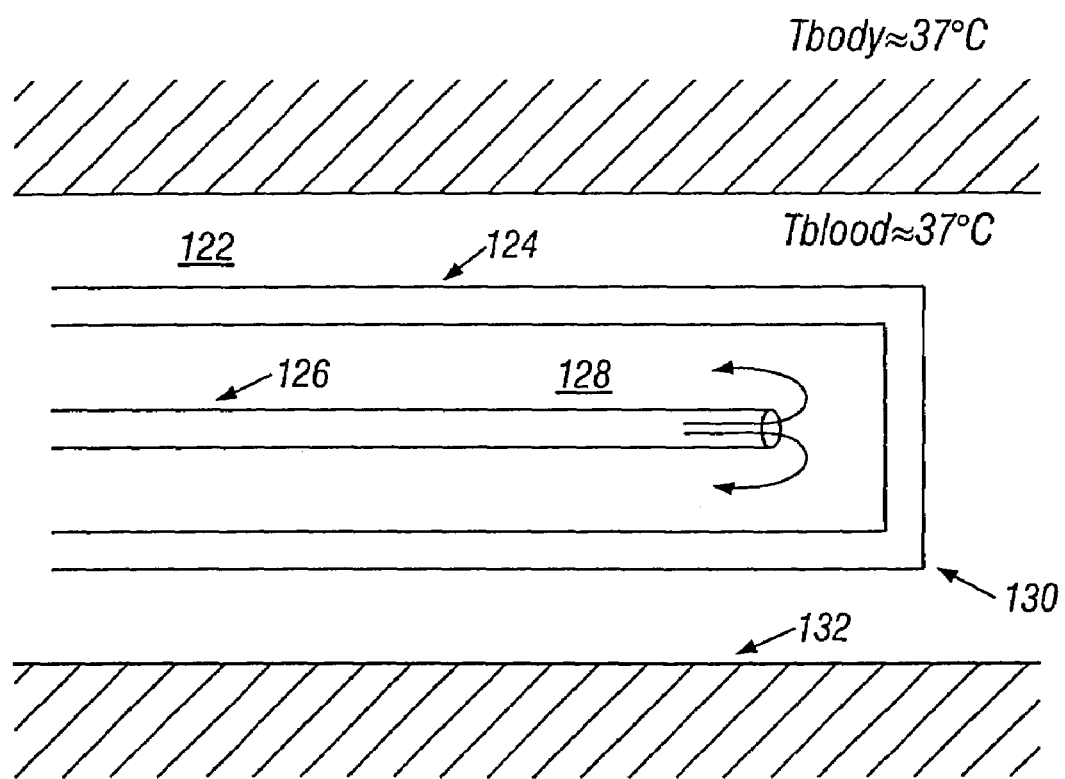
FIG. 3 is a schematic diagram of a heat transfer element according to an embodiment of the invention.

A device according to an embodiment of the invention for accomplishing such cooling or heating is shown schematically in FIG. 3, which shows a vessel wall 132 in which a blood flow 122 is passing. A catheter 130 is disposed within the blood flow 122 to affect the blood temperature. Catheter 130 has an inlet lumen 126 for providing a working fluid 128 and an outlet lumen 124 for draining the working fluid 128. The functions of the respective lumens may of course be opposite to that stated.

Heat transfer in this system is governed by the following mechanisms:

(1) convective heat transfer from the blood 122 to the outlet lumen 124;

(2) conduction through the wall of the outlet lumen 124;

(3) convective heat transfer from the outlet lumen 124 to the working fluid 128;

(4) conduction through the working fluid 128;

(5) convective heat transfer from working fluid 128 in the outlet lumen 124 to the inlet lumen 126; and (6) conduction through the wall of the inlet lumen 126.

Once the materials for the lumens and the working fluid are chosen, the conductive heat transfers are solely dependent on the temperature gradients. Convective heat transfers, by contrast, also rely on the movement of fluid to transfer heat. Forced convection results when the heat transfer surface is in contact with a fluid whose motion is induced (or forced) by a pressure gradient, area variation, or other such force. In the case of blood flow, the beating heart provides an oscillatory pressure gradient to force the motion of the blood in contact with the heat transfer surface. One of the aspects of the device uses mixing or turbulence to enhance this forced convective heat transfer.

The rate of convective heat transfer Q is proportional to the product of S, the area of the heat transfer element in direct contact with the fluid, $\Delta T = T_b - T_s$, the temperature differential between the surface temperature $T_s$ of the heat transfer element and the free stream blood temperature $T_b$, and $\overline{h}_c$, the average convection heat transfer coefficient over the heat transfer area. $\overline{h}_c$ is sometimes called the "surface coefficient of heat transfer" or the "convection heat transfer coefficient".

The magnitude of the heat transfer rate Q to or from the fluid flow can be increased through manipulation of the above three parameters. Practical constraints limit the value of these parameters and how much they can be manipulated. For example, the internal diameter of the common carotid artery ranges from 6 to 8 mm. Thus, the heat transfer element residing therein may not be much larger than 4 mm in diameter to avoid occluding the vessel. The length of the heat transfer element should also be limited. For placement within the internal and common carotid artery, the length of the heat transfer element is limited to about 10 cm. This estimate is based on the length of the common carotid artery, which ranges from 8 to 12 cm. Embodiments intended for use in the venous system would be analyzed similarly. For these venous systems, catheter sizes may be, e.g., 9 French, 10.7 French, 14 French, etc.

Consequently, the value of the surface area S is limited by the physical constraints imposed by the size of the vessel into which the device is placed. Surface features, such as fins, can be used to increase the surface area of the heat transfer element, however, these features alone generally cannot usually provide enough surface area enhancement to meet the required heat transfer rate.

An embodiment of the device described below provides a tapered heat transfer element which employs a large surface area but which may advantageously fit into small arteries and veins. As the device is inflatable, the same may be inserted in relatively small arteries and veins in a deflated state, allowing a minimally invasive entry. When the device is in position, the same may be inflated, allowing a large surface area and thus an enhanced heat transfer rate.

One may also attempt to vary the magnitude of the heat transfer rate by varying $\Delta T$. The value of $\Delta T = T_b - T_s$ can be varied by varying the surface temperature $T_s$ of the heat transfer element. The allowable surface temperature of the heat transfer element is limited by the characteristics of blood. The blood temperature is fixed at about 37° C., and blood freezes at approximately 0° C. When the blood approaches freezing, ice emboli may form in the blood which may lodge downstream, causing serious ischemic injury. Furthermore, reducing the temperature of the blood also increases its viscosity which results in a small decrease in the value of $\overline{h}_c$. Increased viscosity of the blood may further result in an increase in the pressure drop within the vessel, thus compromising the flow of blood. Given the above constraints, it may be advantageous to limit the surface temperature of the heat transfer element to approximately 1° C.-5° C., thus resulting in a maximum temperature differential between the blood stream and the heat transfer element of approximately 32° C.-36° C.

One may also attempt to vary the magnitude of the heat transfer rate by varying $\overline{h}_c$. Fewer constraints are imposed on the value of the convection heat transfer coefficient $\overline{h}_c$. The mechanisms by which the value of $\overline{h}_c$ may be increased are complex. However, one way to increase $\overline{h}_c$ for a fixed mean value of the velocity is to increase the level of turbulent kinetic energy in the fluid flow.

The heat transfer rate $Q_{no\text{-}flow}$ in the absence of fluid flow is proportional to $\Delta T$, the temperature differential between the surface temperature $T_s$ of the heat transfer element and the free stream blood temperature $T_b$ times k, the diffusion constant, and is inversely proportion to $\delta$, the thickness of the boundary layer.

The magnitude of the enhancement in heat transfer by fluid flow can be estimated by taking the ratio of the heat transfer rate with fluid flow to the heat transfer rate in the absence of fluid flow $N=Q_{flow}/Q_{no\text{-}flow}=\overline{h}_c/(k/\delta)$. This ratio is called the Nusselt number ("Nu"). For convective heat transfer between blood and the surface of the heat transfer element, Nusselt numbers of 30-80 have been found to be appropriate for selective cooling applications of various organs in the human body. Nusselt numbers are generally dependent on several other numbers: the Reynolds number, the Womersley number, and the Prandtl number.

Stirring-type mechanisms, which abruptly change the direction of velocity vectors, may be utilized to induce turbulent kinetic energy and increase the heat transfer rate. The level of turbulence so created is characterized by the turbulence intensity I. Turbulence intensity I is defined as the root mean square of the fluctuating velocity divided by the mean velocity. Such mechanisms can create high levels of turbulence intensity in the free stream, thereby increasing the heat transfer rate. For arterial applications, this turbulence intensity should ideally be sustained for a significant portion of the cardiac cycle, and should ideally be created throughout the free stream and not just in the boundary layer.

One type of turbulence-inducing heat transfer element which may be advantageously employed to provide heating or cooling is described in U.S. Pat. No. 6,096,068 to Dobak and Lasheras for a "Selective Organ Cooling Catheter and Method of Using the Same," incorporated by reference above. In that application, the heat transfer element is made of a high thermal conductivity material, such as metal. The metal heat transfer element provides a high degree of heat transfer due to its high thermal conductivity. In that application, bellows provided a high degree of articulation that compensated for the intrinsic stiffness of the metal. The device size was minimized, e.g., less than 4 mm, to prevent blockage of the blood flowing in the vessel.

Figure 4:
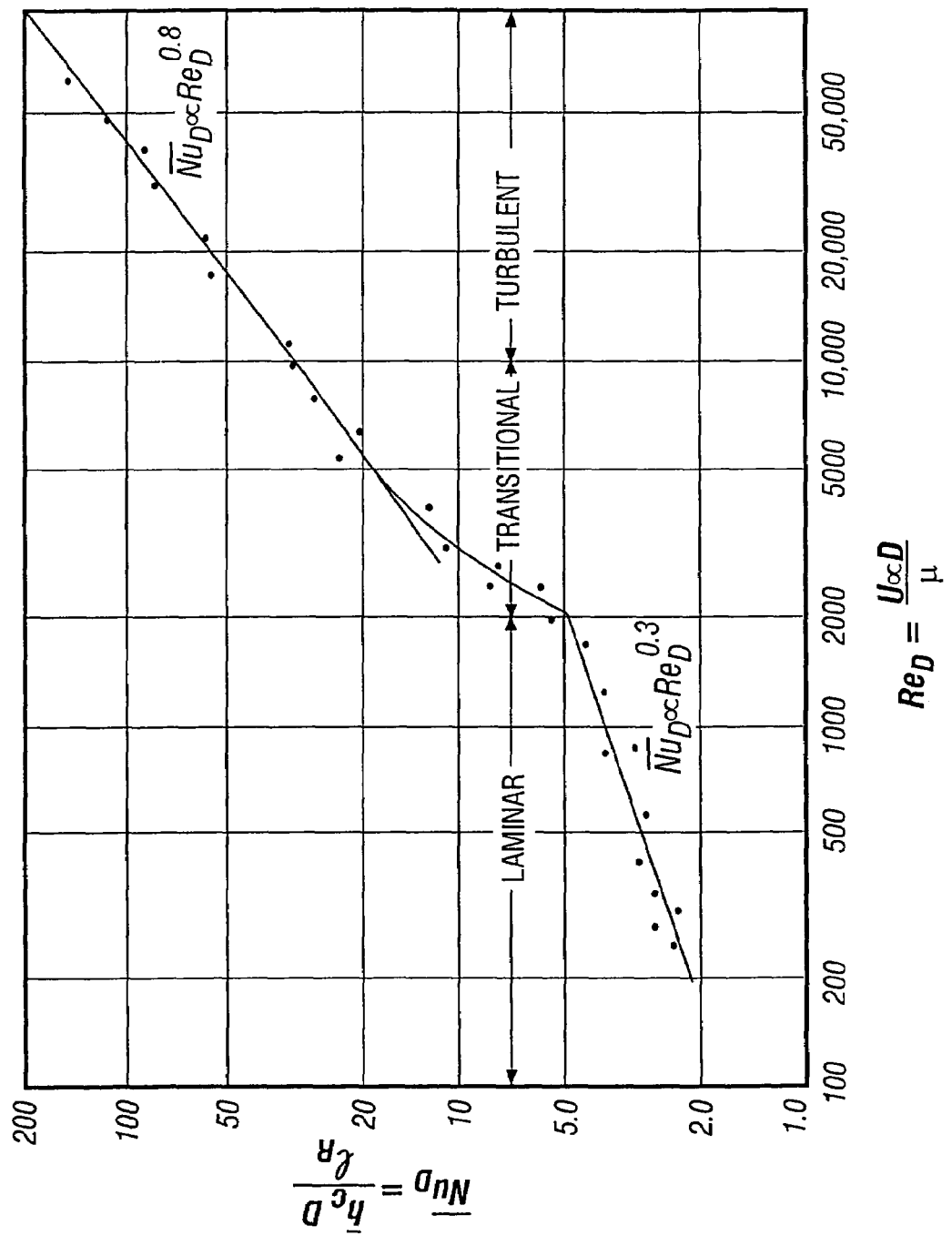
FIG. 4 is a graph showing the relationship between the Nusselt number (Nu) and the Reynolds number (Re) for air flowing through a long heated pipe at uniform wall temperature.

FIG. 4 illustrates the dependency of the Nusselt number on the Reynolds number for a fluid flowing through a long duct, i.e., air flowing though a long heated pipe at a uniform wall temperature. Although FIG. 4 illustrates this relationship for a different fluid through a different structure, the inventors of the present invention believe a similar relationship exists for blood flow through a blood vessel. FIG. 4 illustrates that flow is laminar when the Reynolds number is below some number, in this case about 2100. In the range of Reynolds numbers between another set of numbers, in this case 2100 and 10,000, a transition from laminar to turbulent flow takes place. The flow in this regime is called transitional. The mixing caused by the heat transfer element of the present invention produces a flow that is at least transitional. At another Reynolds number, in the case above, about 10,000, the flow becomes fully turbulent.

The type of flow that occurs is important because in laminar flow through a duct, there is no mixing of warmer and colder fluid particles by eddy motion. Thus, the only heat transfer that takes place is through conduction. Since most fluids have small thermal conductivities, the heat transfer coefficients in laminar flow are relatively small. In transitional and turbulent flow, mixing occurs through eddies that carry warmer fluid into cooler regions and vice versa. Since the mixing motion, even if it is only on a small scale compared to fully turbulent flow, accelerates the transfer of heat considerably, a marked increase in the heat transfer coefficient occurs above a certain Reynolds number, which in the graph of FIG. 4 is about 2100. It can be seen from FIG. 4 that it is at approximately this point where the Nusselt number increases more dramatically. A different set of numbers may be measured for blood flow through an artery or vein. However, the inventors believe that a Nusselt number at least in the transitional region may be important for enhanced heat transfer.

Device

Figure 5:
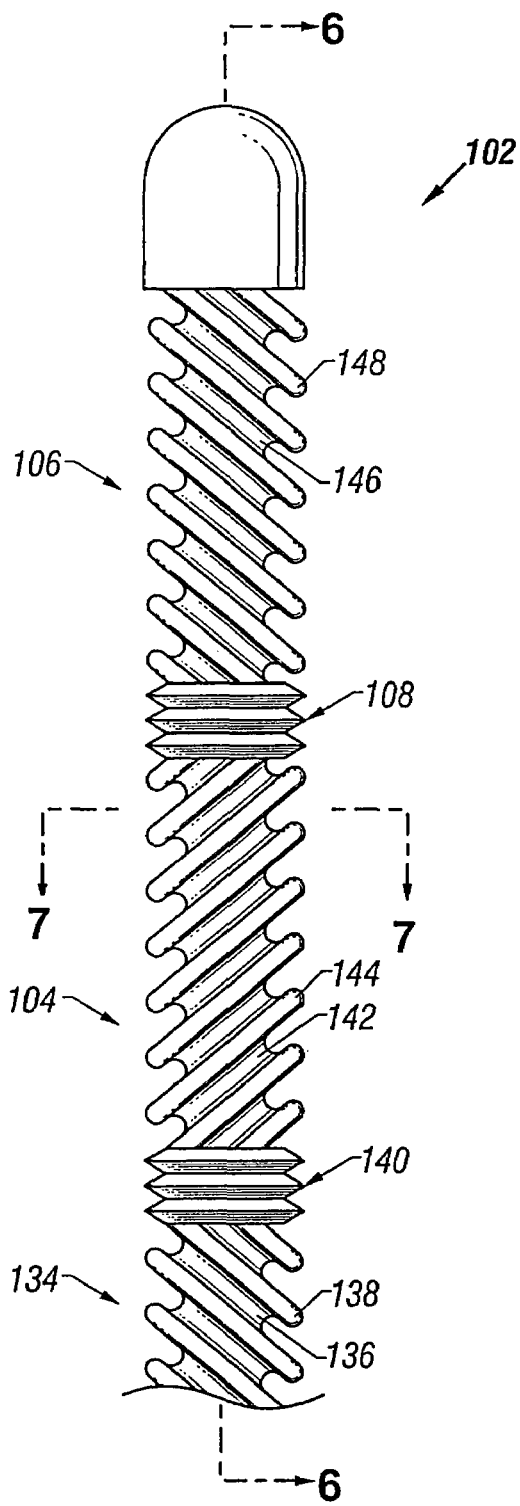
FIG. 5 is an elevation view of one embodiment of a heat transfer element according to the invention.

FIG. 5 is an elevation view of one embodiment of a cooling element 102 according to the present invention. The heat transfer element 102 includes a series of elongated, articulated segments or modules 134,104,106. Three such segments are shown in this embodiment, but two or more such segments could be used without departing from the spirit of the invention. As seen in FIG. 5, a first elongated heat transfer segment 134 is located at the proximal end of the heat transfer element 102. A mixing-inducing exterior surface of the segment 134 includes four parallel helical ridges 138 with four parallel helical grooves 136 therebetween. One, two, three, or more parallel helical ridges 138 could also be used without departing from the spirit of the present invention. In this embodiment, the helical ridges 138 and the helical grooves 136 of the heat transfer segment 134 have a left hand twist, referred to herein as a counter-clockwise spiral or helical rotation, as they proceed toward the distal end of the heat transfer segment 134.

The first heat transfer segment 134 is coupled to a second elongated heat transfer segment 104 by a first bellows section 140, which provides flexibility and compressibility. The second heat transfer segment 104 includes one or more helical ridges 144 with one or more helical grooves 142 therebetween. The ridges 144 and grooves 142 have a right hand, or clockwise, twist as they proceed toward the distal end of the heat transfer segment 104. The second heat transfer segment 104 is coupled to a third elongated heat transfer segment 106 by a second bellows section 108. The third heat transfer segment 106 includes one or more helical ridges 148 with one or more helical grooves 146 therebetween. The helical ridge 148 and the helical groove 146 have a left hand, or counter-clockwise, twist as they proceed toward the distal end of the heat transfer segment 106. Thus, successive heat transfer segments 134, 104, 106 of the heat transfer element 102 alternate between having clockwise and counterclockwise helical twists. The actual left or right hand twist of any particular segment is immaterial, as long as adjacent segments have opposite helical twist.

In addition, the rounded contours of the ridges 138, 144, 148 allow the heat transfer element 102 to maintain a relatively atraumatic profile, thereby minimizing the possibility of damage to the blood vessel wall. A heat transfer element according to the present invention may include two, three, or more heat transfer segments.

The bellows sections 140, 108 are formed from seamless and nonporous materials, such as metal, and therefore are impermeable to gas, which can be particularly important, depending on the type of working fluid that is cycled through the heat transfer element 102. The structure of the bellows sections 140, 108 allows them to bend, extend and compress, which increases the flexibility of the heat transfer element 102 so that it is more readily able to navigate through blood vessels. The bellows sections 140, 108 also provide for axial compression of the heat transfer element 102, which can limit the trauma when the distal end of the heat transfer element 102 abuts a blood vessel wall. The bellows sections 140, 108 are also able to tolerate cryogenic temperatures without a loss of performance. In alternative embodiments, the bellows may be replaced by flexible polymer tubes, which are bonded between adjacent heat transfer segments.

The exterior surfaces of the heat transfer element 102 can be made from metal, and may include very high thermal conductivity materials such as nickel, thereby facilitating heat transfer. Alternatively, other metals such as stainless steel, titanium, aluminum, silver, copper and the like, can be used, with or without an appropriate coating or treatment to enhance biocompatibility or inhibit clot formation. Suitable biocompatible coatings include, e.g., gold, platinum or polymer paralyene. The heat transfer element 102 may be manufactured by plating a thin layer of metal on a mandrel that has the appropriate pattern. In this way, the heat transfer element 102 may be manufactured inexpensively in large quantities, which is an important feature in a disposable medical device.

Because the heat transfer element 102 may dwell within the blood vessel for extended periods of time, such as 24-48 hours or even longer, it may be desirable to treat the surfaces of the heat transfer element 102 to avoid clot formation. In particular, one may wish to treat the bellows sections 140, 108 because stagnation of the blood flow may occur in the convolutions, thus allowing clots to form and cling to the surface to form a thrombus. One means by which to prevent thrombus formation is to bind an antithrombogenic agent to the surface of the heat transfer element 102. For example, heparin is known to inhibit clot formation and is also known to be useful as a biocoating. Alternatively, the surfaces of the heat transfer element 102 may be bombarded with ions such as nitrogen. Bombardment with nitrogen can harden and smooth the surface and thus prevent adherence of clotting factors. Another coating that provides beneficial properties may be a lubricious coating. Lubricious coatings, on both the heat transfer element and its associated catheter, allow for easier placement in the, e.g., vena cava.

Figure 6:
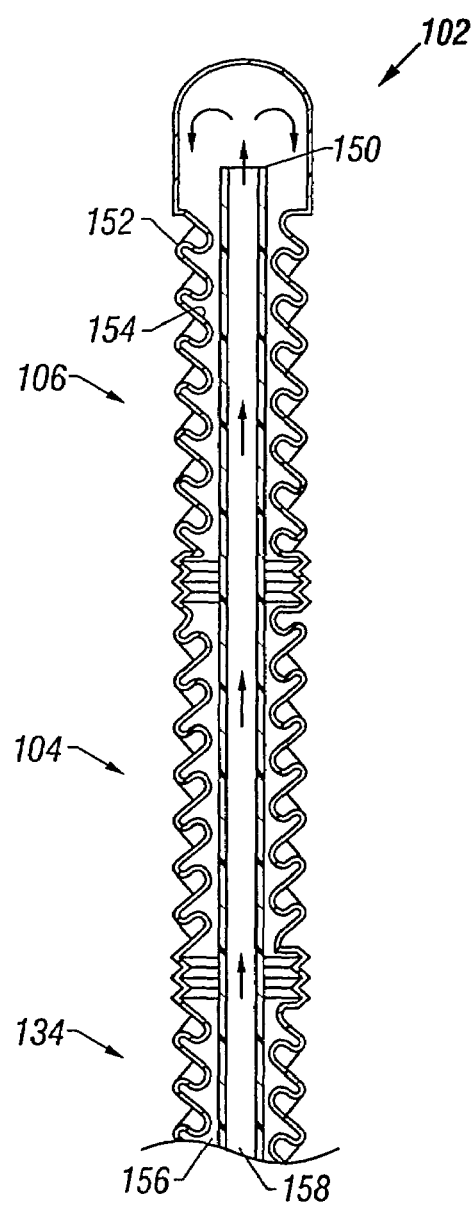
FIG. 6 is a longitudinal section view of the heat transfer element of FIG. 5.

FIG. 6 is a longitudinal sectional view of the heat transfer element 102 of an embodiment of the invention, taken along line 6-6 in FIG. 5. Some interior contours are omitted for purposes of clarity. An inner tube 150 creates an inner lumen 158 and an outer lumen 156 within the heat transfer element 102. Once the heat transfer element 102 is in place in the blood vessel, a working fluid such as saline or other aqueous solution may be circulated through the heat transfer element 102. Fluid flows from a source into the inner lumen 158. At the distal end of the heat transfer element 102, the working fluid exits the inner lumen 158 and enters the outer lumen 156. As the working fluid flows through the outer lumen 156, heat is transferred between the working fluid and the exterior surface 152 of the heat transfer element 102. Because the heat transfer element 102 is constructed from a high conductivity material, the temperature of its exterior surface 152 may reach very close to the temperature of the working fluid. The tube 150 may be formed as an insulating divider to thermally separate the inner lumen 158 from the outer lumen 156. For example, insulation may be achieved by creating longitudinal air channels in the wall of the insulating tube 150. Alternatively, the tube 150 may be constructed of a non-thermally conductive material like polytetrafluoroethylene or another polymer.

It is important to note that the same mechanisms that govern the heat transfer rate between the exterior surface 152 of the heat transfer element 102 and the blood also govern the heat transfer rate between the working fluid and the interior surface 154 of the heat transfer element 102. The heat transfer characteristics of the interior surface 154 are particularly important when using water, saline or other fluid that remains a liquid as the working fluid. Other coolants such as Freon undergo nucleate boiling and create mixing through a different mechanism. Saline is a safe working fluid, because it is non-toxic, and leakage of saline does not result in a gas embolism, which could occur with the use of boiling refrigerants. Since mixing in the working fluid is enhanced by the shape of the interior surface 154 of the heat transfer element 102, the working fluid can be delivered to the cooling element 102 at a warmer temperature and still achieve the necessary cooling rate. Similarly, since mixing in the working fluid is enhanced by the shape of the interior surface of the heat transfer element, the working fluid can be delivered to the warming element 102 at a cooler temperature and still achieve the necessary warming rate.

This has a number of beneficial implications in the need for insulation along the catheter shaft length. Due to the decreased need for insulation, the catheter shaft diameter can be made smaller. The enhanced heat transfer characteristics of the interior surface of the heat transfer element 102 also allow the working fluid to be delivered to the heat transfer element 102 at lower flow rates and lower pressures. High pressures may make the heat transfer element stiff and cause it to push against the wall of the blood vessel, thereby shielding part of the exterior surface 152 of the heat transfer element 102 from the blood. Because of the increased heat transfer characteristics achieved by the alternating helical ridges 138, 144, 148, the pressure of the working fluid may be as low as 5 atmospheres, 3 atmospheres, 2 atmospheres or even less than 1 atmosphere.

Figure 7:
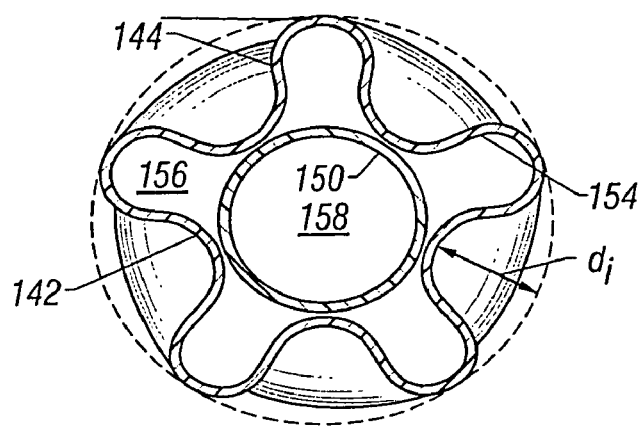
FIG. 7 is a transverse section view of the heat transfer element of FIG. 5.

FIG. 7 is a transverse sectional view of the heat transfer element 102 of the invention, taken at a location denoted by the line 7-7 in FIG. 5. FIG. 7 illustrates a five-lobed embodiment, whereas FIG. 5 illustrates a four-lobed embodiment. As mentioned earlier, any number of lobes might be used. In FIG. 7, the construction of the heat transfer element 102 is clearly shown. The inner lumen 158 is defined by the insulating tube 150. The outer lumen 156 is defined by the exterior surface of the insulating tube 150 and the interior surface 154 of the heat transfer element 102. In addition, the helical ridges 144 and helical grooves 142 may be seen in FIG. 7. Although FIG. 7 shows five ridges and five grooves, the number of ridges and grooves may vary. Thus, heat transfer elements with 1, 2, 3, 4, 5, 6, 7, 8 or more ridges are specifically contemplated.

Figure 8:
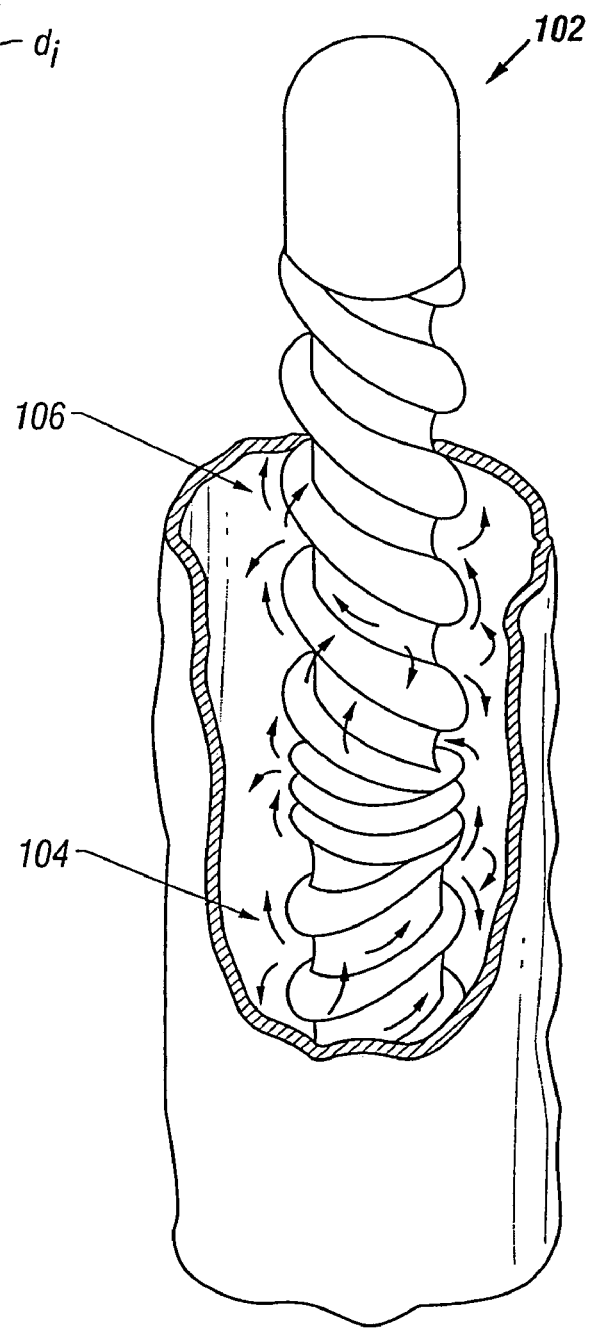
FIG. 8 is a perspective view of the heat transfer element of FIG. 5 in use within a blood vessel.

FIG. 8 is a perspective view of a heat transfer element 102 in use within a blood vessel, showing only one helical lobe per segment for purposes of clarity. Beginning from the proximal end of the heat transfer element (not shown in FIG. 8), as the blood moves forward, the first helical heat transfer segment 104 induces a counter-clockwise rotational inertia to the blood. As the blood reaches the second segment 104, the rotational direction of the inertia is reversed, causing mixing within the blood. Further, as the blood reaches the third segment 106, the rotational direction of the fluid is again reversed. The sudden changes in flow direction actively reorient and randomize the velocity vectors, thus ensuring mixing throughout the bloodstream. During such mixing, the velocity vectors of the blood become more random and, in some cases, become perpendicular to the axis of the vessel. Thus, a large portion of the volume of warm blood in the vessel is actively brought in contact with the heat transfer element 102 where it can be cooled by direct contact rather than being cooled largely by conduction through adjacent laminar layers of blood.

Referring back to FIG. 5, the heat transfer element 102 has been designed to address all of the design criteria discussed above. The heat transfer element 102 is flexible and is made of a highly conductive material. The flexibility is provided by a segmental distribution of bellows sections 140, 108 that provide an articulating mechanism. Bellows have a known convoluted design that provide flexibility. The ridges allow the heat transfer element 102 to maintain a relatively atraumatic profile, thereby minimizing the possibility of damage to the vessel wall. The heat transfer element 102 has been designed to promote mixing both internally and externally. The modular or segmental design allows the direction of the grooves to be reversed between segments. The alternating helical rotations create an alternating flow that results in mixing the blood in a manner analogous to the mixing action created by the rotor of a washing machine that switches directions back and forth. This action is intended to promote mixing to enhance the heat transfer rate. The alternating helical design also causes beneficial mixing, or turbulent kinetic energy, of the working fluid flowing internally.

Figure 9:
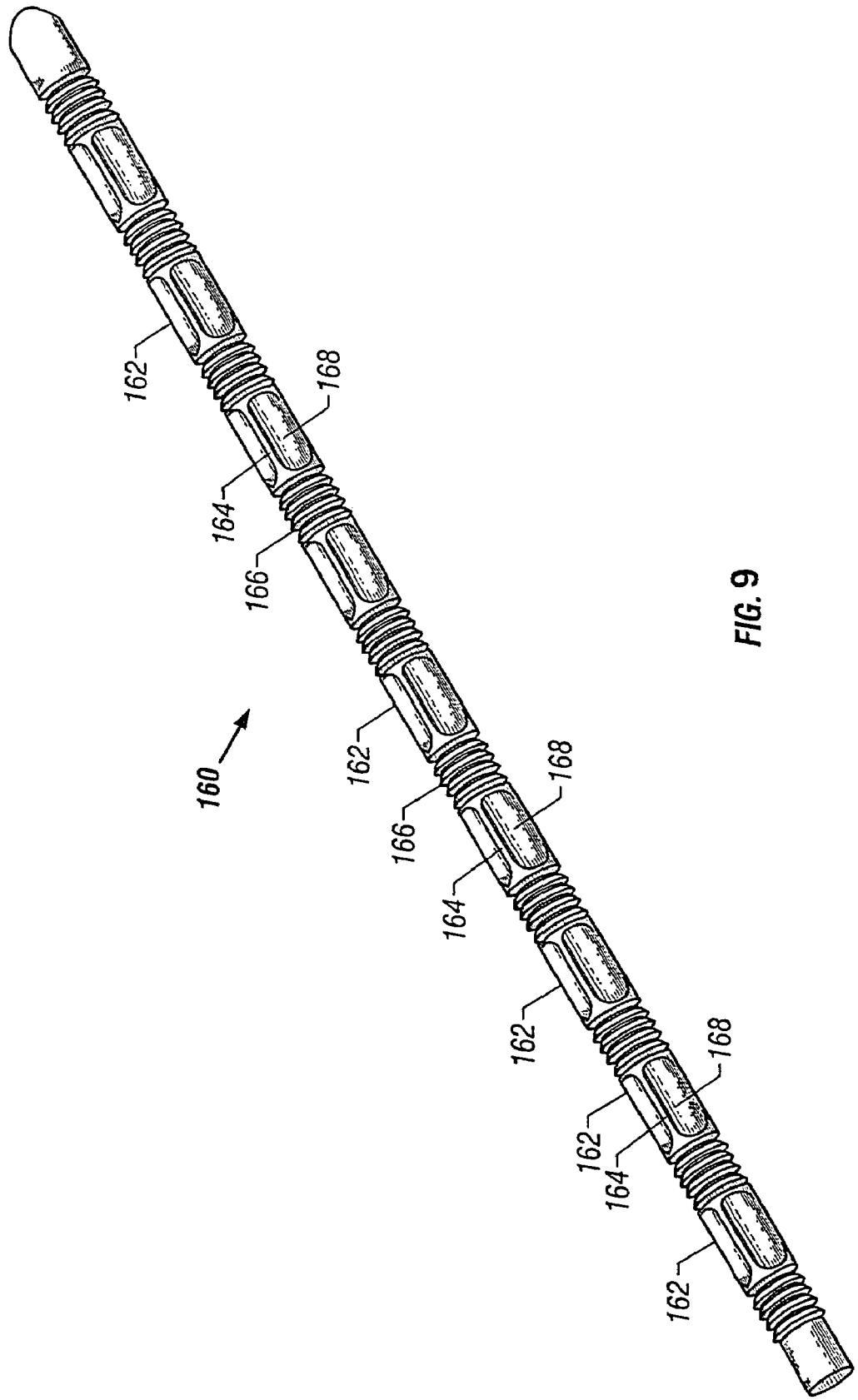
FIG. 9 is a perspective view of another embodiment of a heat transfer element according to the invention, with aligned longitudinal ridges on adjacent segments.

FIG. 9 is a perspective view of a third embodiment of a heat transfer element 160 according to the present invention. The heat transfer element 160 is comprised of a series of elongated, articulated segments or modules 162. A first elongated heat transfer segment 162 is located at the proximal end of the heat transfer element 160. The segment 162 may be a smooth right circular cylinder (not shown), or it can incorporate a turbulence-inducing or mixing-inducing exterior surface. The turbulence-inducing or mixing-inducing exterior surface shown on the segment 162 in FIG. 16 comprises a plurality of parallel longitudinal ridges 164 with parallel longitudinal grooves 168 therebetween. One, two, three, or more parallel longitudinal ridges 164 could be used without departing from the spirit of the present invention. In the embodiment where they are used, the longitudinal ridges 164 and the longitudinal grooves 168 of the heat transfer segment 162 are aligned parallel with the axis of the first heat transfer segment 162.

The first heat transfer segment 162 is coupled to a second elongated heat transfer segment 162 by a first flexible section such as a bellows section 166, which provides flexibility and compressibility. Alternatively, the flexible section may be a simple flexible tube, very similar to a smooth heat transfer segment, but flexible. The second heat transfer segment 162 also comprises a plurality of parallel longitudinal ridges 164 with parallel longitudinal grooves 168 therebetween. The longitudinal ridges 164 and the longitudinal grooves 168 of the second heat transfer segment 162 are aligned parallel with the axis of the second heat transfer segment 162. The second heat transfer segment 162 is coupled to a third elongated heat transfer segment 162 by a second flexible section such as a bellows section 166 or a flexible tube. The third heat transfer segment 162 also comprises a plurality of parallel longitudinal ridges 164 with parallel longitudinal grooves 168 therebetween. The longitudinal ridges 164 and the longitudinal grooves 168 of the third heat transfer segment 162 are aligned parallel with the axis of the third heat transfer segment 162. Further, in this embodiment, adjacent heat transfer segments 162 of the heat transfer element 160 have their longitudinal ridges 164 aligned with each other, and their longitudinal grooves 168 aligned with each other. Offsetting of the longitudinal ridges and the longitudinal grooves from each other on adjacent segments promotes turbulence or mixing in blood flowing past the exterior of the heat transfer element 170. In other embodiments, they may be offset.

In addition, the rounded contours of the ridges 164 also allow the heat transfer element 160 to maintain a relatively atraumatic profile, thereby minimizing the possibility of damage to the blood vessel wall. A heat transfer element 160 according to the present invention may be comprised of two., three, or more heat transfer segments 162.

Figure 10:
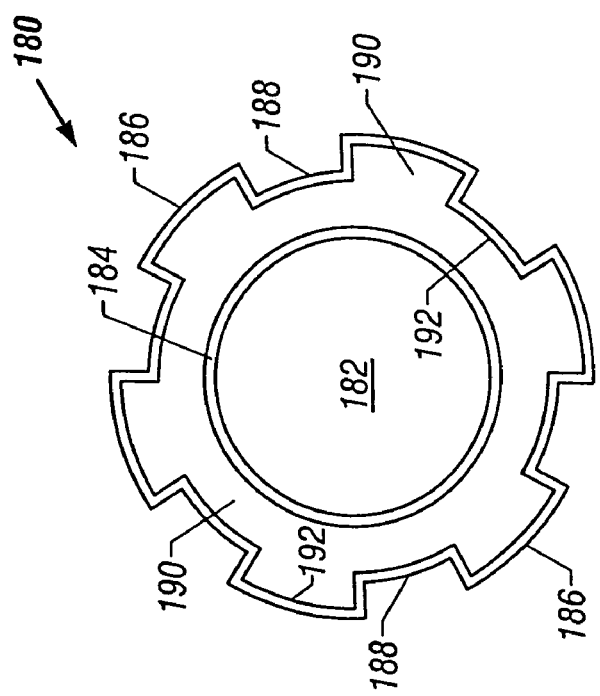
FIG. 10 is a transverse section view of the heat transfer element of FIG. 9.

FIG. 10 is a transverse section view of a heat transfer segment 180, illustrative of segment 162 of heat transfer element 160 shown in FIG. 9. The coaxial construction of the heat transfer segment 180 is clearly shown. The inner coaxial lumen 182 is defined by the insulating coaxial tube 184. The outer lumen 190 is defined by the exterior surface of the insulating coaxial tube 184 and the interior surface 192 of the heat transfer segment 180. In addition, parallel longitudinal ridges 186 and parallel longitudinal grooves 188 may be seen in FIG. 10. The longitudinal ridges 186 and the longitudinal grooves 188 may have a relatively rectangular cross-section, as shown in FIG. 10, or they may be more triangular in cross-section, as shown in FIG. 9. The longitudinal ridges 186 and the longitudinal grooves 188 may be formed only on the exterior surface of the segment 180, with a cylindrical interior surface 192. Alternatively, corresponding longitudinal ridges and grooves may be formed on the interior surface 192 as shown, to promote turbulence or mixing in the working fluid. Although FIG. 10 shows six ridges and six grooves, the number of ridges and grooves may vary. Where a smooth exterior surface is desired, the outer tube of the heat transfer segment 180 could have smooth outer and inner surfaces, like the inner tube 184. Alternatively, the outer tube of the heat transfer segment 180 could have a smooth outer surface and a ridged inner surface like the interior surface 192 shown in FIG. 10.

Figure 11:
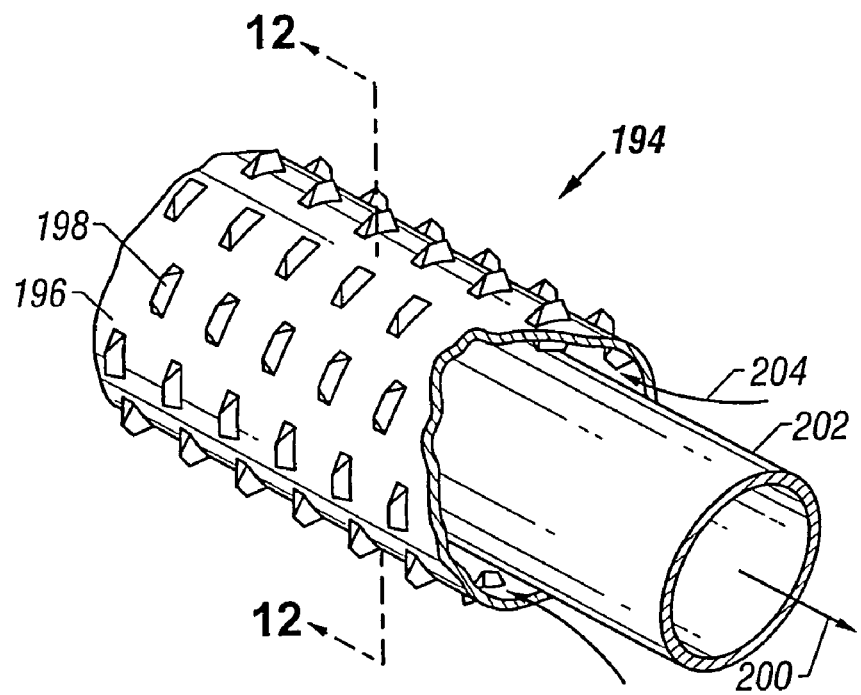
FIG. 11 is a cut-away perspective view of an alternative embodiment of a heat transfer element according to the invention.

FIG. 11 is a cut-away perspective view of an alternative embodiment of a heat transfer element 194. An external surface 196 of the heat transfer element 194 is covered with a series of axially staggered protrusions 198. The staggered nature of the outer protrusions 198 is readily seen with reference to FIG. 12 which is a transverse cross-sectional view taken at a location denoted by the line 12-12 in FIG. 11. As the blood flows along the external surface 196, it collides with one of the staggered protrusions 198 and a turbulent wake flow is created behind the protrusion. As the blood divides and swirls alongside of the first staggered protrusion 198, its turbulent wake encounters another staggered protrusion 198 within its path preventing the re-lamination of the flow and creating yet more mixing. In this way, the velocity vectors are randomized and mixing is created not only in the boundary layer but also throughout a large portion of the free stream. As is the case with the preferred embodiment, this geometry also induces a mixing effect on the internal working fluid flow.

Figure 12:
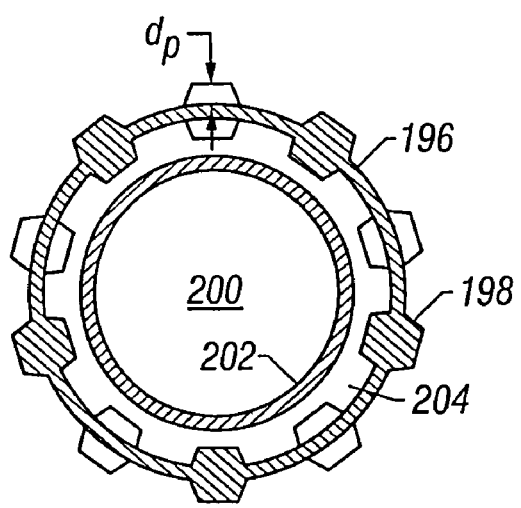
FIG. 12 is a transverse section view of the heat transfer element of FIG. 11.

A working fluid is circulated up through an inner lumen 200 defined by an insulating tube 202 to a distal tip of the heat transfer element 194. The working fluid then traverses an outer lumen 204 in order to transfer heat to the exterior surface 196 of the heat transfer element 194. The inside surface of the heat transfer element 194 is similar to the exterior surface 196 in order to induce turbulent or "mixed" flow of the working fluid. The inner protrusions can be aligned with the outer protrusions 198 as shown in FIG. 12 or they can be offset from the outer protrusions 198 as shown in FIG. 11.

Figure 13:
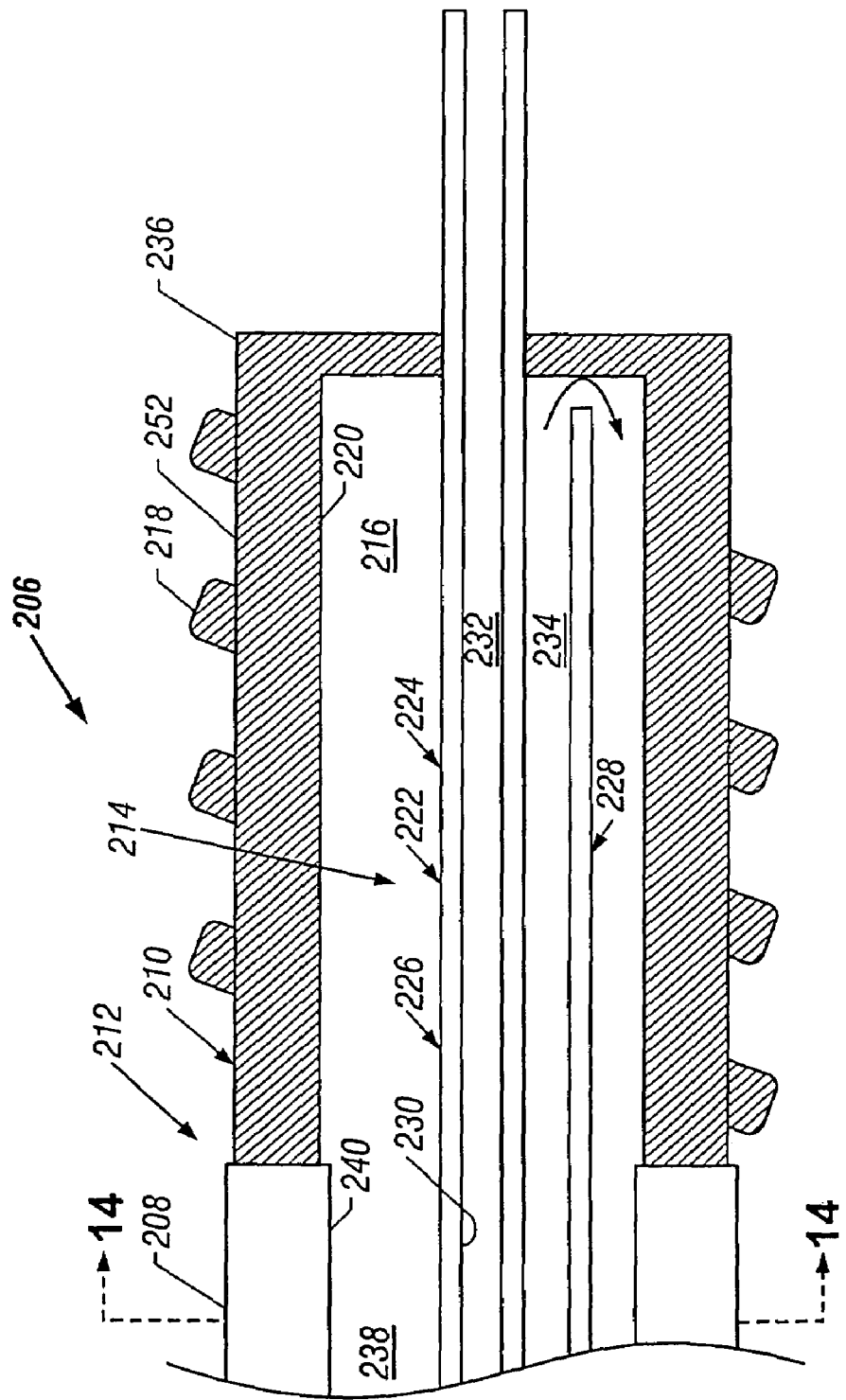
FIG. 13 is a front sectional view of a further embodiment of a catheter employing a heat transfer element according to the principles of the invention further employing a side-by-side lumen arrangement constructed in accordance with an embodiment of the invention.
Figure 14:
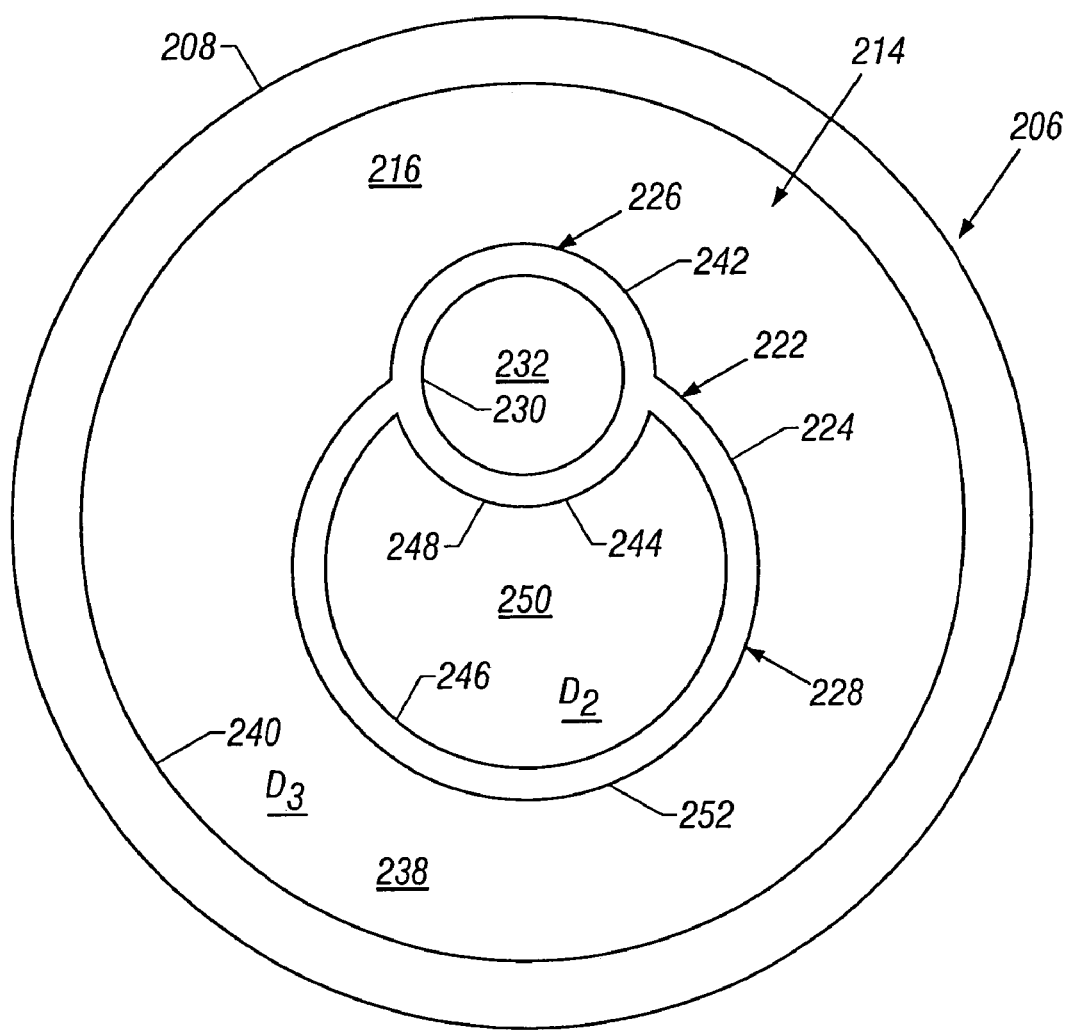
FIG. 14 is a cross-sectional view of the catheter of FIG. 13 taken along line 14-14 of FIG. 13.

With reference to FIGS. 13 and 14, a catheter 206 constructed in accordance with an alternative embodiment of the invention will now be described. The catheter 206 includes an elongated catheter body 208 with a heat transfer element 210 located at a distal portion 212 of the catheter body 208. The catheter 206 includes a multiple lumen arrangement 214 to deliver fluid to and from an interior 216 of the heat transfer element 210 and allow the catheter 206 to be placed into a blood vessel over a guidewire. The heat transfer element 210 includes turbulence-inducing invaginations 218 located on an exterior surface 252. Similar invaginations may be located on an interior surface 220 of the heat transfer element 210, but are not shown for clarity. Further, it should be noted that the heat transfer element 210 is shown with only four invaginations 218. Other embodiments may employ multiple elements connected by flexible joints or bellows as disclosed above. A single heat transfer element is shown in FIG. 13 merely for clarity. In an alternative embodiment of the invention, any of the other heat-transfer elements described herein may replace heat transfer element 212. Alternatively, the multi-lumen arrangement may be used to deliver fluid to and from the interior of an operative element(s) other than a heat-transfer-element such as, but without limitation, a catheter balloon, e.g., a dilatation balloon.

The catheter 206 includes an integrated elongated multiple lumen member such as a bi-lumen member 222 having a first lumen member 226 and a second lumen member 228. The bi-lumen member 222 has a substantially figure-eight cross-sectional shape (FIG. 14) and an outer surface 224 with the same general shape. The first lumen member 226 includes an interior surface 230 defining a first lumen or guide wire lumen 232 having a substantially circular cross-sectional shape. The interior surface 230 may be coated with a lubricious material to facilitate the sliding of the catheter 206 over a guidewire. The first lumen member 226 further includes a first exterior surface 242 and a second exterior surface 244. The first lumen 232 is adapted to receive a guide wire for placing the catheter 206 into a blood vessel over the guidewire in a well-known manner.

In FIGS. 13 and 14, the guide wire lumen 232 is not coaxial with the catheter body 208. In an alternative embodiment of the invention, the guide wire lumen 232 may be coaxial with the catheter body 208.

The second lumen member 228 includes a first interior surface 246 and a second interior surface 248, which is the same as the second exterior surface 244 of the first lumen member 226, that together define a second lumen or supply lumen 250 having a substantially luniform cross-sectional shape. The second lumen member 228 further includes an exterior surface 252. The second lumen 250 has a cross-sectional area $A_2$. The second lumen 250 is adapted to supply working fluid to the interior of the heat transfer element 210 to provide temperature control of a flow or volume of blood in the manner described above.

The second lumen member 228 terminates short of a distal end 236 of the catheter 206, leaving sufficient space for the working fluid to exit the supply lumen 250 so it can contact the interior surface 220 of the heat transfer element 210 for heat transfer purposes.

Figure 15:
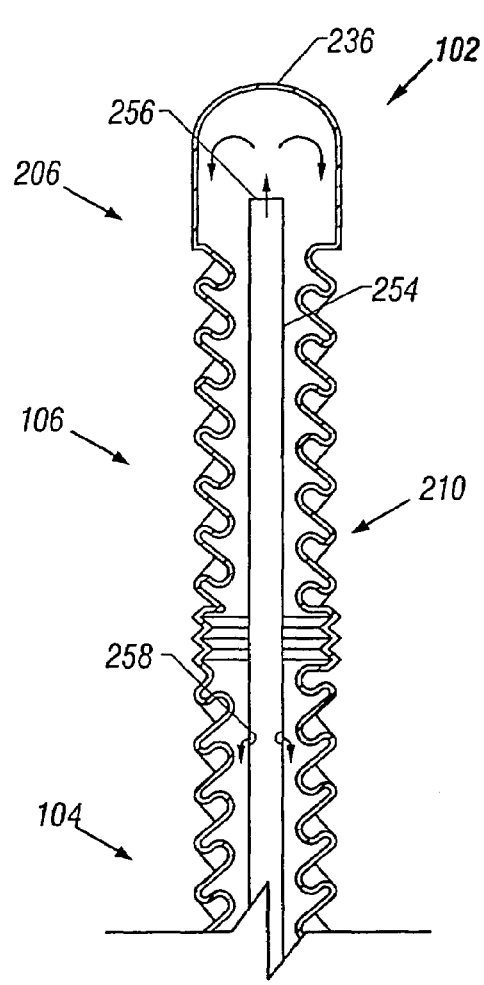
FIG. 15 is a front sectional view of a catheter employing a heat transfer element and lumen arrangement constructed in accordance with a further embodiment of the invention.

Although the second lumen member 228 is shown as a single supply lumen terminating adjacent the distal end 236 of catheter 206 to deliver working fluid at the distal end of the catheter 206, with reference to FIG. 15, in an alternative embodiment of the invention, a single supply lumen member 254 may include one or more outlet openings 256 adjacent the distal end 236 of the catheter 206 and one or more outlet openings 258 adjacent a mid-point along the interior length of the heat transfer element 210. This arrangement improves the heat transfer characteristics of the heat-transfer element 210 because fresh working fluid at the same temperature is delivered separately to each segment 104, 106 of the interior of the heat-transfer element 210 instead of in series.

Although two heat transfer segments 104, 106 are shown, it will be readily apparent that a number of heat transfer segments other than two, e.g., one, three, four, etc., may be used.

It will be readily apparent to those skilled in the art that in another embodiment of the invention, in addition to the one or more openings 256 in the distal portion of the heat transfer element 210, one or more openings at one or more locations may be located anywhere along the interior length of the heat transfer element 210 proximal to the distal portion.

Figure 16:
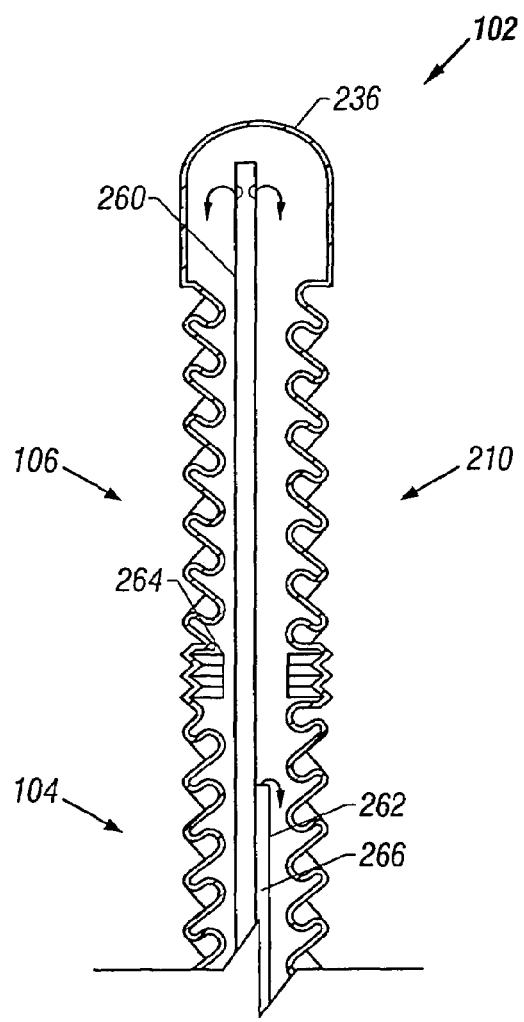
FIG. 16 is a front sectional view of a catheter employing a heat transfer element and lumen arrangement constructed in accordance with a still further embodiment of the invention.

With reference to FIG. 16, in an alternative embodiment of the invention, first and second supply lumen members 260, 262 define respective first and second supply lumens 264, 266 for supplying working fluid to the interior of the heat transfer element 210. The first supply lumen 260 terminates just short of the distal end 236 of the catheter 206 to deliver working fluid at the distal portion of the heat transfer element 210. The second supply lumen 262 terminates short of the distal portion of the catheter 206, for example, at approximately a mid-length point along the interior of the heat transfer element 210 for delivering working fluid to the second heat transfer segment 104. In an alternative embodiment of the invention, the second lumen member 262 may terminate anywhere along the interior length of the heat transfer element 210 proximal to the distal portion of the heat transfer element 210. Further, a number of supply lumens 262 greater than two may terminate along the interior length of the heat transfer element 210 for delivering a working fluid at a variety of points along the interior length of the heat transfer element 210.

With reference back to FIGS. 13 and 14, the bitumen member 222 is preferably extruded from a material such as polyurethane or Pebax. In an embodiment of the invention, the bitumen member is extruded simultaneously with the catheter body 208. In an alternative embodiment of the invention, the first lumen member 226 and second lumen member 228 are formed separately and welded or fixed together.

A third lumen or return lumen 238 provides a convenient return path for working fluid. The third lumen 238 is substantially defined by the interior surface 220 of the heat transfer element 210, an interior surface 240 of the catheter body 208, and the exterior surface 224 of the bitumen member 222. The inventors have determined that the working fluid pressure drop through the lumens is minimized when the third lumen 238 has a hydraulic diameter $D_3$ that is equal to 0.75 of the hydraulic diameter $D_2$ of the second lumen 250. However, the pressure drop that occurs when the ratio of the hydraulic diameter $D_3$ to the hydraulic diameter $D_2$ is substantially equal to 0.75, i.e., 0.75±0.10, works well. For flow through a cylinder, the hydraulic diameter D of a lumen is equal to four times the cross-sectional area of the lumen divided by the wetted perimeter. The wetted perimeter is the total perimeter of the region defined by the intersection of the fluid path through the lumen and a plane perpendicular to the longitudinal axis of the lumen. The wetted perimeter for the return lumen 238 would include an inner wetted perimeter (due to the outer surface 224 of the bi-lumen member 222) and an outer wetted perimeter (due to the interior surface 240 of the catheter body 208). The wetted perimeter for the supply lumen 250 would include only an outer wetted perimeter (due to the first and second interior surfaces 246, 248 of the bitumen member 222). Thus, the wetted perimeter for a lumen depends on the number of boundary surfaces that define the lumen.

The third lumen 238 is adapted to return working fluid delivered to the interior of the heat transfer element 210 back to an external reservoir or the fluid supply for recirculation in a well-known manner.

In an alternative embodiment, the third lumen 238 is the supply lumen and the second lumen 250 is the return lumen. Accordingly, it will be readily understood by the reader that adjectives such as "first," "second," etc. are used to facilitate the reader's understanding of the invention and are not intended to limit the scope of the invention, especially as defined in the claims.

In a further embodiment of the invention, the member 222 may include a number of lumens other than two such as, for example, 1, 3, 4, 5, etc. Additional lumens may be used as additional supply and/or return lumens, for other instruments, e.g., imaging devices, or for other purposes, e.g., inflating a catheter balloon or delivering a drug.

Heating or cooling efficiency of the heat transfer element 210 is optimized by maximizing the flow rate of working fluid through the lumens 250, 238 and minimizing the transfer of heat between the working fluid and the supply lumen member. Working fluid flow rate is maximized and pressure drop minimized in the present invention by having the ratio of the hydraulic diameter $D_3$ of the return lumen 238 to the hydraulic diameter $D_2$ of the supply lumen 250 equal to 0.75. However, a ratio substantially equal to 0.75, i.e., 0.75±10-20%, is acceptable. Heat transfer losses are minimized in the supply lumen 250 by minimizing the surface area contact made between the bitumen member 222 and the working fluid as it travels through the supply lumen member. The surface area of the supply lumen member that the supplied working fluid contacts is much less than that in co-axial or concentric lumens used in the past because the supplied working fluid only contacts the interior of one lumen member compared to contacting the exterior of one lumen member and the interior of another lumen member. Thus, heat transfer losses are minimized in the embodiments of the supply lumen in the multiple lumen member 222 of the present invention.

Figure 17:
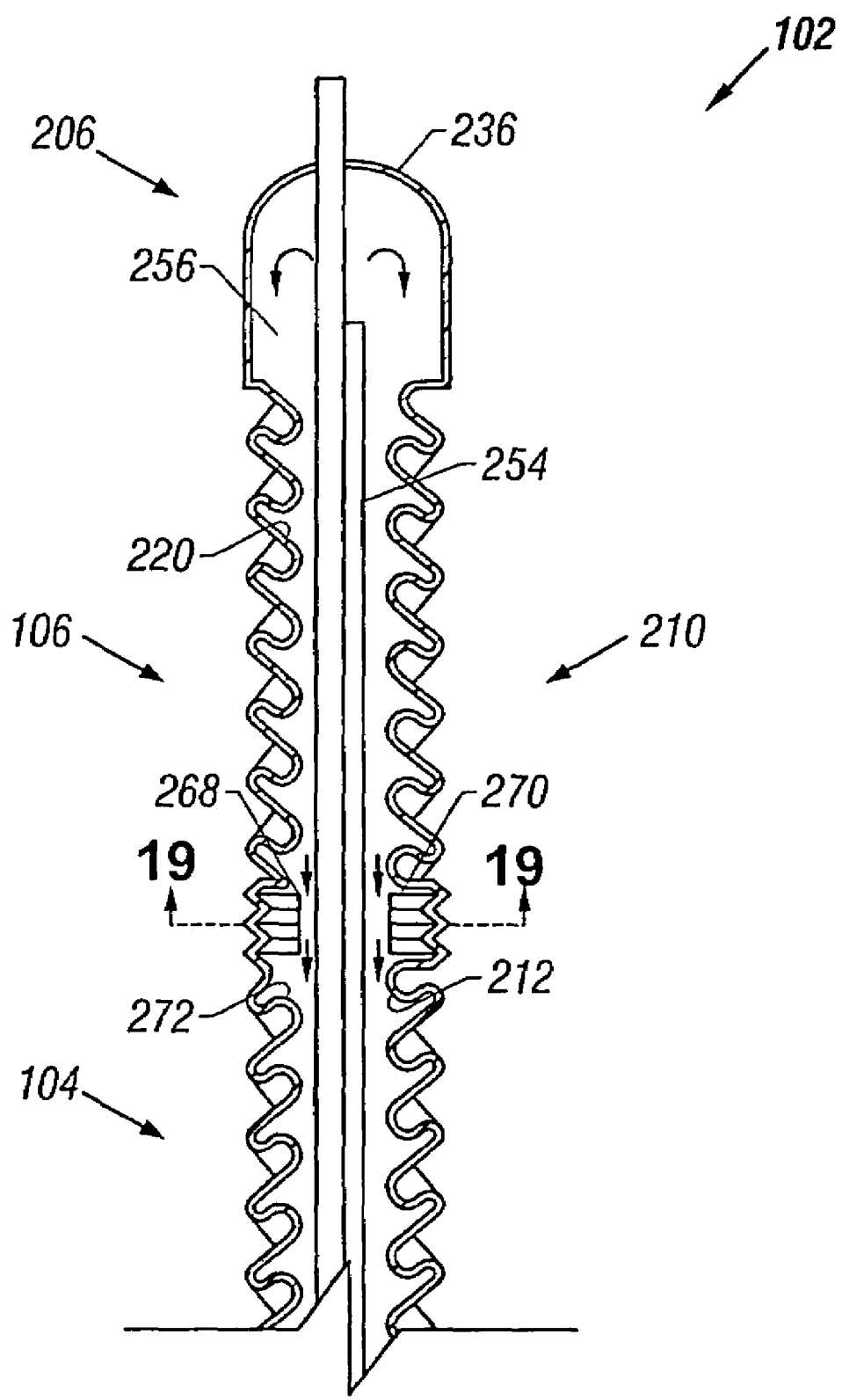
FIG. 17 is a front sectional view of another embodiment of a catheter employing a heat transfer element according to the principles of the invention further employing a side-by-side lumen arrangement constructed in accordance with another embodiment of the invention.
Figure 18:
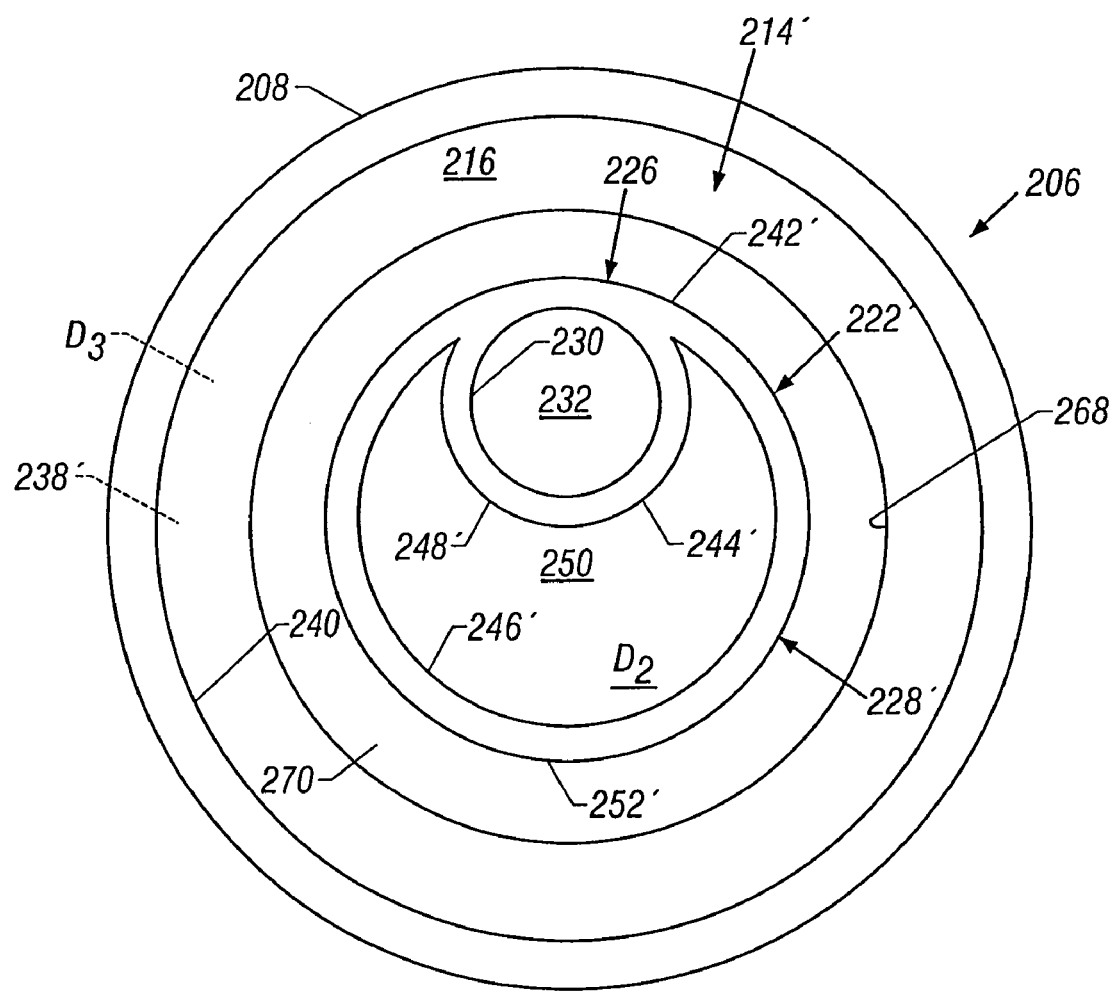
FIG. 18 is a cross-sectional view of the heat transfer element illustrated in FIG. 17.

It will be readily apparent to those skilled in the art that the supply lumen 250 and the return lumen 238 may have cross-sectional shapes other than those shown and described herein and still maintain the desired hydraulic diameter ratio of substantially 0.75. With reference to FIGS. 17 and 18, an example of a catheter 206 including a supply lumen and a return lumen constructed in accordance with an alternative preferred embodiment of the invention, where the hydraulic diameter ratio of the return lumen to the supply lumen is substantially equal to 0.75 is illustrated. It should be noted, the same elements as those described above with respect to FIGS. 13 and 14 are identified with the same reference numerals and similar elements are identified with the same reference numerals, but with a (') suffix.

The catheter 206 illustrated in FIGS. 17 and 18 includes a multiple lumen arrangement 214' for delivering working fluid to and from an interior 216 of the heat transfer element 210 and allowing the catheter to be placed into a blood vessel over a guide wire. The multiple lumen arrangement 214' includes a bitumen member 222' with a slightly different construction from the bitumen member 222 discussed above with respect to FIGS. 13 and 14. Instead of an outer surface 224 that is generally figure eight shaped, the bi-lumen member 222' has an outer surface 224' that is circular. Consequently, the third lumen 238' has an annular cross-sectional shape.

As discussed above, maintaining the hydraulic diameter ratio of the return lumen 250' to the supply lumen 238' substantially equal to 0.75 maximizes the working fluid flow rate through the multiple lumen arrangement 214'.

In addition, the annular return lumen 238' enhances the convective heat transfer coefficient within the heat transfer element 210, especially adjacent an intermediate segment or bellows segment 268. Working fluid flowing through the annular return lumen 238', between the outer surface 224' of the bitumen member 222' and the inner surface 220 of the heat transfer element, encounters a restriction 270 caused by the impingement of the bellows section 268 into the flow path. Although the impingement of the bellows section 268 is shown as causing the restriction 270 in the flow path of the return lumen 238', in an alternative embodiment of the invention, the bitumen member 222' may create the restriction 270 by being thicker in this longitudinal region of the bitumen member 222'. The distance between the bitumen member 222' and the bellows section 268 is such that the characteristic flow resulting from a flow of working fluid is at least of a transitional nature.

For a specific working fluid flux or flow rate (cc/sec), the mean fluid velocity through the bellows section restriction 270 will be greater than the mean fluid velocity obtained through the annular return lumen 238' in the heat transfer segment 104, 106 of the heat transfer element 210. Sufficiently high velocity through the bellows section restriction 270 will result in wall jets 272 directed into the interior portion 220 of the heat transfer segment 104. The wall jets 272 enhance the heat transfer coefficient within the helical heat transfer segment 104 because they enhance the mixing of the working fluid along the interior of the helical heat transfer segment 104. Increasing the velocity of the jets 272 by increasing the working fluid flow rate or decreasing the size of the restriction 270 will result in a transition closer to the jet exit and greater mean turbulence intensity throughout the helical heat transfer segment 104. Thus, the outer surface 224' of the bitumen member 222', adjacent the bellows 268, and the inner surface of the bellows 268 form means for further enhancing the transfer of heat between the heat transfer element 210 and the working fluid, in addition to that caused by the interior portion 220 of the helical heat transfer segment 104.

In an alternative embodiment of the invention, as described above, the heat transfer element may include a number of heat transfer segments other than two, i.e., 1, 3, 4, etc., with a corresponding number of intermediate segments, i.e., the number of heat transfer segments minus one.

The embodiment of the multiple lumen arrangement 222 discussed with respect to FIGS. 13 and 14 would not enhance the convective heat transfer coefficient as much as the embodiment of the multiple lumen arrangement 222' discussed with respect to FIGS. 17 and 18 because working fluid would preferentially flow through the larger areas of the return lumen 238, adjacent the junction of the first lumen member 226 and second lumen member 228. Thus, high-speed working fluid would have more contact with the outer surface 224 of the bi-lumen member 222 and less contact with the interior portion of 220 heat transfer element 210. In contrast, the annular return lumen 238' of the multiple lumen arrangement 222' causes working fluid flow to be axisymmetric so that significant working fluid flow contacts all areas of the helical segment equally.

On the other hand, the heat transfer element according to an embodiment of the present invention may also be made of a flexible material, such as latex rubber. The latex rubber provides a high degree of flexibility which was previously achieved by articulation. The latex rubber further allows the heat transfer element to be made collapsible so that when deflated the same may be easily inserted into a vessel. Insertion and location may be conveniently made by way of a guide catheter or guide wire. Following insertion and location in the desired vessel, the heat transfer element may be inflated for use by a working fluid such as saline, water, perfluorocarbons, or other suitable fluids.

A heat transfer element made of a flexible material generally has significantly less thermal conductivity than a heat transfer element made of metal. The device compensates for this by enhancing the surface area available for heat transfer. This may be accomplished in two ways: by increasing the cross-sectional size and by increasing the length. Regarding the former, the device may be structured to be large when inflated, because when deflated the same may still be inserted into an artery or vein. In fact, the device may be as large as the vessel wall, so long as a path for blood flow is allowed, because the flexibility of the device tends to prevent damage to the wall even upon contact. Such paths are described below. Regarding the latter, the device may be configured to be long. One way to configure a long device is to taper the same so that the device may fit into distal vessels having reduced radii in a manner described below. The device further compensates for the reduced thermal conductivity by reducing the thickness of the heat transfer element wall. In alternative embodiments, versions of the device use a heat transfer element design that produces a high level of mixing or turbulence in the free stream of the blood and in the working fluid. One embodiment of the invention forces a helical motion on the working fluid and imposes a helical barrier in the blood, causing mixing. In an alternative embodiment, the helical barrier is tapered. In a second alternative embodiment, a tapered inflatable heat transfer element has a shape or surface features to cause mixing or turbulence. As one example, the surface features may be a spiral shape. In another example, the surface features may be staggered protrusions. In all of these embodiments, the design forces a high level of mixing in the free stream of the blood by causing the blood to navigate a tortuous path while passing through the vessel. This tortuous path causes the blood to undergo violent accelerations resulting in turbulence.

In a third alternative embodiment of the invention, a taper of an inflatable heat transfer element provides enough additional surface area per se to cause sufficient heat transfer. In all of the embodiments, the inflation is performed by the working fluid, such as water or saline.

Figure 19:
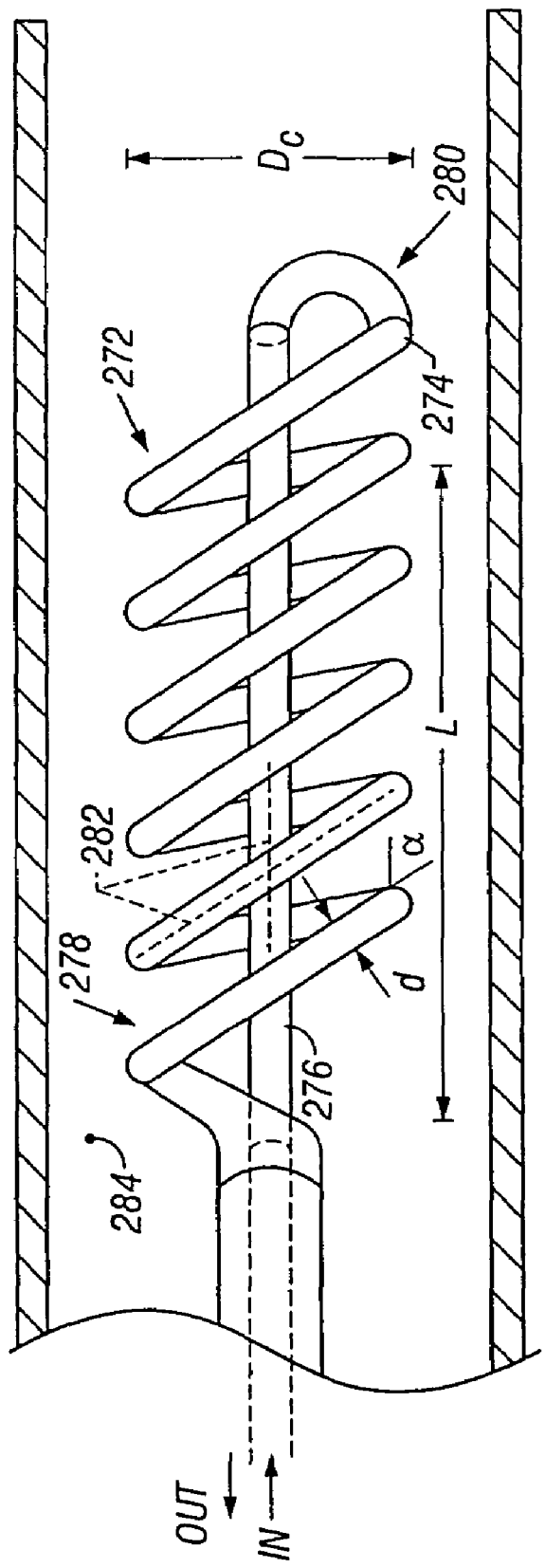
FIG. 19 is a side schematic view of an inflatable heat transfer element according to an embodiment of the invention, as the same is disposed within a blood vessel.

Referring to FIG. 19, a side view is shown of a first embodiment of a heat transfer element 272 according to an embodiment of the invention. The heat transfer element 272 is formed by an inlet lumen 276 and an outlet lumen 274. In this embodiment, the outlet lumen 274 is formed in a helix shape surrounding the inlet lumen 276 that is formed in a pipe shape. The names of the lumens are of course not limiting. It will be clear to one skilled in the art that the inlet lumen 276 may serve as an outlet and the outlet lumen 274 may serve as an inlet. It will also be clear that the heat transfer element is capable of both heating (by delivering heat to) and cooling (by removing heat from) a desired area.

The heat transfer element 272 is rigid but flexible so as to be insertable in an appropriate vessel by use of a guide catheter. Alternatively, the heat transfer element may employ a device for threading a guide wire therethrough to assist placement within an artery. The heat transfer element 272 has an inflated length of L, a helical diameter of $D_c$, a tubal diameter of d, and a helical angle of α. For example, $D_c$ may be about 3.3 mm and d may be about 0.9 mm to 1 mm. Of course, the tubal diameter d need not be constant. For example, the diameter of the inlet lumen 276 may differ from that of the outlet lumen 272.

The shape of the outlet lumen 274 in FIG. 19 is helical. This helical shape presents a cylindrical obstacle, in cross-section, to the flow of blood. Such obstacles tend to create turbulence in the free stream of blood. In particular, the form of turbulence is the creation of von Karman vortices in the wake of the flow of blood, downstream of the cylindrical obstacles.

Typical inflatable materials are not highly thermally conductive. They are much less conductive than the metallic heat transfer element disclosed in the Pat. incorporated by reference above. The difference in conductivity is compensated for in at least two ways in the present device. The material is made thinner and the heat transfer element is afforded a larger surface area. Regarding the former, the thickness may be less than about ½ mil for adequate cooling.

Thin inflatable materials, particularly those with large surface areas, may require a structure, such as a wire, within their interiors to maintain their approximate uninflated positions so that upon inflation, the proper form is achieved. Thus, a wire structure 282 is shown in FIG. 19 that may be advantageously disposed within the inflatable material to perform such a function.

Another consideration is the angle α of the helix. Angle a should be determined to optimize the helical motion of the blood around the lumens 274 and 276, enhancing heat transfer. Of course, angle α should also be determined to optimize the helical motion of the working fluid within the lumens 274 and 276. The helical motion of the working fluid within the lumens 274 and 276 increases the turbulence in the working fluid by creating secondary motions. In particular, helical motion of a fluid in a pipe induces two counter-rotating secondary flows.

An enhancement of $\overline{h_c}$ would be obtained in this system, and this enhancement may be described by a Nusselt number Nu of up to about or even more.

Figure 20:
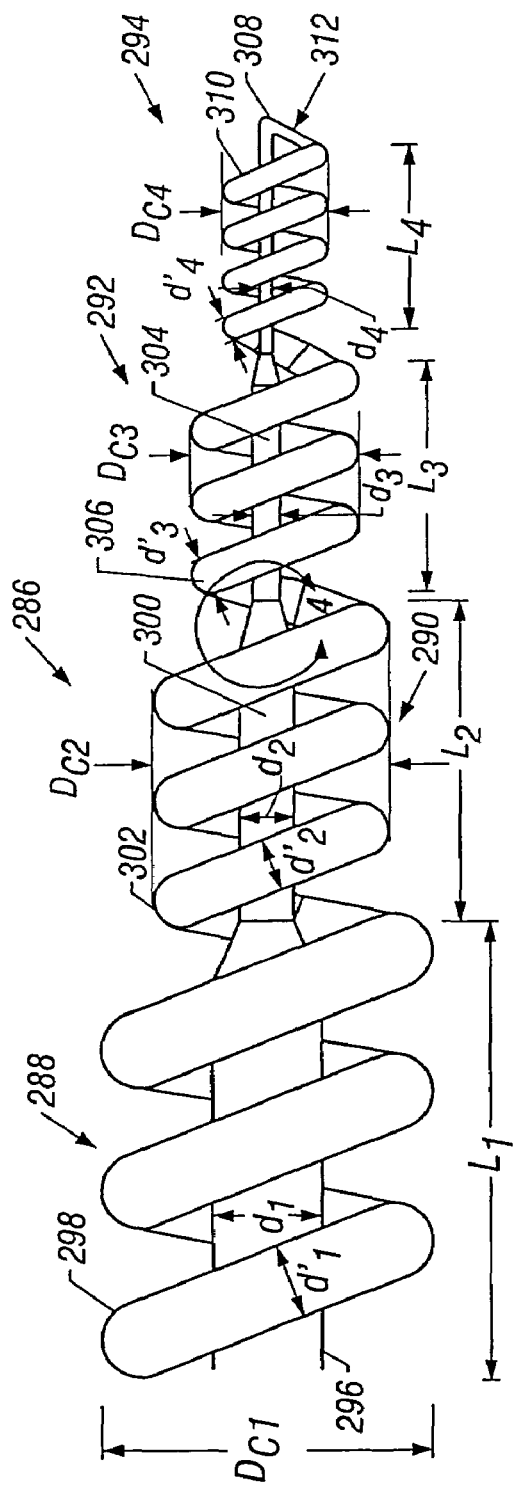
FIG. 20 illustrates an inflatable turbulence-inducing heat transfer element according to an alternative embodiment of the invention employing a surface area enhancing taper and a turbulence-inducing shape.

The above discussion describes one embodiment of a heat transfer element. An alternative embodiment of the device, shown in a side view in FIG. 20, illustrates a heat transfer element 286 with a surface area enhancement. Increasing the surface area of the inflatable material enhances heat transfer. The heat transfer element 272 includes a series of coils or helices of different coil diameters and tubal diameters. It is not strictly necessary that the tubal diameters differ, but it is likely that commercially realizable systems will have differing tubal diameters. The heat transfer element 272 may taper either continuously or segmentally.

This alternative embodiment enhances surface area in two ways. First, the use of smaller diameter lumens enhances the overall surface-to-volume ratio. Second, the use of progressively smaller (i.e., tapered) lumens allows a distal end 312 to be inserted further into an artery than would be possible with the embodiment of FIG. 19.

In the embodiment of FIG. 20, a first coil segment 288 is shown having length $L_1$ and diameter $D_{C1}$. The first coil segment 288 is formed of an inlet lumen 296 having diameter $d_1$ and an outlet lumen 298 having diameter $d_1'$. In the first coil segment, as well as the others, the outlet lumen need not immediately drain the inlet lumen. In FIG. 20, the inlet lumen for each segment feeds the inlet lumen of the succeeding segment except for an inlet lumen adjacent a distal end 312 of the heat transfer element 286 that directly feeds its corresponding outlet lumen.

A separate embodiment may also be constructed in which the inlet lumens each provide working fluid to their corresponding outlet lumens. In this embodiment, either a separate lumen needs to be provided to drain each outlet lumen or each outlet lumen drains into the adjacent outlet lumen. This embodiment has the advantage that an opposite helicity may be accorded each successive segment. The opposite helicities in turn enhance the turbulence of the working fluid flowing past them.

A second coil segment 290 is shown having length $L_2$ and diameter $D_{C2}$. The second coil segment 290 is formed of an inlet lumen 300 having diameter $d_2$ and an outlet lumen 302 having diameter $d_2'$. A third coil segment 292 is shown having length $L_3$ and diameter $D_{C3}$. The third coil segment 292 is formed of an inlet lumen 304 having diameter $d_3$ and an outlet lumen 306 having diameter $d_3'$. Likewise, a fourth coil segment 294 is shown having length $L_4$ and diameter $D_{C4}$. The fourth coil segment 294 is formed of an inlet lumen 308 having diameter $d_4$ and an outlet lumen 310 having diameter $d_4'$. The diameters of the lumens, especially that of the lumen located at or near distal end 312, should be large enough to not restrict the flow of the working fluid within them. Of course, any number of lumens may be provided depending on the requirements of the user.

Figure 21:
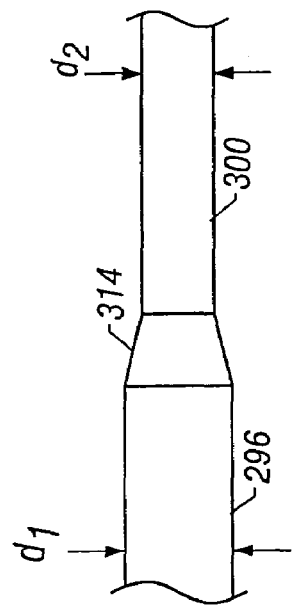
FIG. 21 illustrates a tapered joint which may be employed in the embodiment of FIG. 16.

FIG. 21 shows the connection between two adjacent inlet lumens 296 and 300. A joint 314 is shown coupling the two lumens. The construction of the joint may be by way of variations in stress, hardening, etc.

An advantage to this alternative embodiment arises from the smaller diameters of the distal segments. The heat transfer element of FIG. 20 may be placed in smaller workspaces than the heat transfer element of FIG. 19. For example, a treatment for brain trauma may include placement of a cooling device in the internal carotid artery of a patient. As noted above, the common carotid artery feeds the internal carotid artery. In some patients, the heat transfer element of FIG. 19 may not fit in the internal carotid artery. Similarly, the first coil segment of the heat transfer element in FIG. 20 may not easily fit in the internal carotid artery, although the second, third, and fourth segments may fit. Thus, in the embodiment of FIG. 20, the first coil segment may remain in the common carotid artery while the segments of smaller diameter (the second, third, and fourth) may be placed in the internal carotid artery. In fact, in this embodiment, $D_{C1}$ may be large, such as 5-6 mm. The overall length of the heat transfer element 286 may be, e.g., about 20 to 25 cm. Of course, such considerations play less of a role when the device is placed in a large vein such as the inferior vena cava.

An additional advantage was mentioned above. The surface area of the alternative embodiment of FIG. 20 may be substantially larger than that of the embodiment of FIG. 19, resulting in significantly enhanced heat transfer. For example, the enhancement in surface area may be substantial, such as up to or even more than three times compared to the surface area of the device of the application incorporated by reference above. An additional advantage of both embodiments is that the helical rounded shape allows atraumatic insertion into cylindrical cavities such as, e.g., arteries.

The embodiment of FIG. 20 may result in an Nu from 1 up to about 50.

FIG. 22 shows a second alternative embodiment of the device employing surface features rather than overall shape to induce turbulence. In particular, FIG. 22 shows a heat transfer element 314 having an inlet lumen (not shown) and an outlet inflatable lumen 328 having four segments 316, 318, 320, and 330. Segment 346 is adjacent a proximal end 326 and segment 330 is adjacent a distal end 322. The segments are arranged having reducing radii in the direction of the proximal end to the distal end. In a manner similar to that of the embodiment of FIG. 28, the feature of reducing radii allows insertion of the heat transfer element into small work places such as small arteries.

Heat transfer element 314 has a number of surface features 324 disposed thereon. The surface features 324 may be constructed with, e.g., various hardening treatments applied to the heat transfer element 314, or alternatively by injection molding. The hardening treatments may result in a wavy or corrugated surface to the exterior of heat transfer element 314. The hardening treatments may further result in a wavy or corrugated surface to the interior of heat transfer element 314. FIG. 23 shows a variation of this embodiment, in which a fabrication process is used which results in a spiral or helical shape to the surface features.

The embodiment of FIG. 22 may result in an Nu of about 1 to 50.

Of course, other surface features may also be used which result in turbulence in fluids flowing past them. These include spirals, helices, protrusions, various polygonal bodies, pyramids, tetrahedrons, wedges, etc.

In some situations, an enhanced surface area alone, without the creation of additional turbulence, may result in sufficient heat transfer to cool the blood. Referring to FIG. 24, a heat transfer element 332 is shown having an inlet lumen 334 and an outlet lumen 336. The inlet lumen 334 provides a working fluid to the heat transfer element 332 and outlet lumen 336 drains the working fluid from the same. The functions may, of course, be reversed. The heat transfer element 332 is further divided into five segments, although more or less may be provided as dictated by requirements of the user. The five segments in FIG. 24 are denoted segments 338, 340, 342, 344, and 346. In FIG. 24, the segment 338 has a first and largest radius $R_1$, followed by corresponding radii for segments 340, 342, 344, and 346. Segment 346 has a second and smallest radius. The length of the segment 338 is $L_1$, followed by corresponding lengths for segments 340, 342, 344, and 346.

A purely tapered (nonsegmented) form may replace the tapered segmental form, but the former may be more difficult to manufacture. In either case, the tapered form allows the heat transfer element 332 to be disposed in small arteries, i.e., arteries with radii smaller than $R_1$. A sufficient surface area is thus afforded even in very small arteries to provide the required heat transfer.

The surface area and thus the size of the device should be substantial to provide the necessary heat transfer. Example dimensions for a three-segmented tapered form may be as follows: $L_1$=10 cm, $R_1$=2.5 mm; $L_2$=10 cm, $R_2$=1.65 mm, $L_3$=5 cm, $R_3$=1 mm. Such a heat transfer element would have an overall length of 25 cm and a surface area of $3 \times 10\text{-}4 \text{ m}^2$.

The embodiment of FIG. 24 results in an enhancement of the heat transfer rate of up to about 300% due to the increased surface area S alone.

A variation of the embodiment of FIG. 24 includes placing at least one mixing-inducing surface feature within the interior of the outlet lumen 336. This surface feature may induce mixing in the working fluid, thereby increasing the convective heat transfer rate in the manner described above.

Another variation of the embodiment of FIG. 24 involves reducing the joint diameter between segments (not shown). For example, the inflatable material may be formed such that joints 348, 350, 352, and 354 have a diameter only slightly greater than that of the inlet lumen 334. In other words, the heat transfer element 332 has a tapered "sausage" shape.

In all of the embodiments, the inflatable material may be formed from seamless and nonporous materials that are therefore impermeable to gas. Impermeability can be particularly important depending on the type of working fluid that is cycled through the heat transfer element. For example, the inflatable material may be latex or other such rubber materials, or alternatively of any other material with similar properties under inflation. The flexible material allows the heat transfer element to bend, extend and compress so that it is more readily able to navigate through tiny blood vessels. The material also provides for axial compression of the heat transfer element that can limit the trauma when the distal end of the heat transfer element 272 abuts a blood vessel wall. The material should be chosen to tolerate temperatures in the range of $-1°$ C. to $37°$ C., or even higher in the case of blood heating, without a loss of performance.

In these embodiments as well, it may be desirable to treat the surface of the heat transfer element to avoid clot formation because the heat transfer element may dwell within the blood vessel for extended periods of time, such as 24-48 hours or even longer. One means by which to prevent thrombus formation is to bind an antithrombogenic agent to the surface of the heat transfer element. For example, heparin is known to inhibit clot formation and is also known to be useful as a biocoating.

Referring back to FIG. 19, an embodiment of the method of the invention will be described. A description with reference to the other embodiments is analogous. A guide catheter or wire may be disposed up to or near the area to be cooled or heated. The heat transfer element may be fed over the guide wire to the area. The movement of the heat transfer element is made significantly more convenient by the flexibility of the heat transfer element as has been described above.

Once the heat transfer element 272 is in place, a working fluid such as saline or other aqueous solution may be circulated through the heat transfer element 272 to inflate the same. Fluid flows from a supply catheter into the inlet lumen 276. At the distal end 280 of the heat transfer element 272, the working fluid exits the inlet lumen 276 and enters the outlet lumen 274.

In the case of the embodiment of FIG. 22, the working fluid exits the inlet lumen and enters an outlet inflatable lumen 328 having segments 316, 318, 320, and 330. As the working fluid flows through the outlet lumen 328, heat is transferred from the exterior surface of the heat transfer element 314 to the working fluid. The temperature of the external surface may reach very close to the temperature of the working fluid because the heat transfer element 314 is constructed from very thin material.

The working fluids that may be employed in the device include water, saline or other fluids that remain liquid at the temperatures used. Other coolants, such as freon, undergo nucleated boiling and may create turbulence through a different mechanism. Saline is a safe coolant because it is non-toxic and leakage of saline does not result in a gas embolism that may occur with the use of boiling refrigerants.

By enhancing turbulence in the coolant, the coolant can be delivered to the heat transfer element at a warmer temperature and still achieve the necessary heat transfer rate. In particular, the enhanced heat transfer characteristics of the internal structure allow the working fluid to be delivered to the heat transfer element at lower flow rates and lower pressures. This is advantageous because high pressures may stiffen the heat transfer element and cause the same to push against the wall of the vessel, thereby shielding part of the heat transfer unit from the blood. Such pressures are unlikely to damage the walls of the vessel because of the increased flexibility of the inflated device. The increased heat transfer characteristics allow the pressure of the working fluid to be delivered at pressures as low as 5 atmospheres, 3 atmospheres, 2 atmospheres or even less than 1 atmosphere. In a preferred embodiment, the heat transfer element creates a turbulence intensity greater than 0.05 in order to create the desired level of turbulence in the entire blood stream during the whole cardiac cycle. The turbulence intensity may be greater than 0.055, 0.06, 0.07 or up to 0.10 or 0.20 or even greater.

Figure 25:
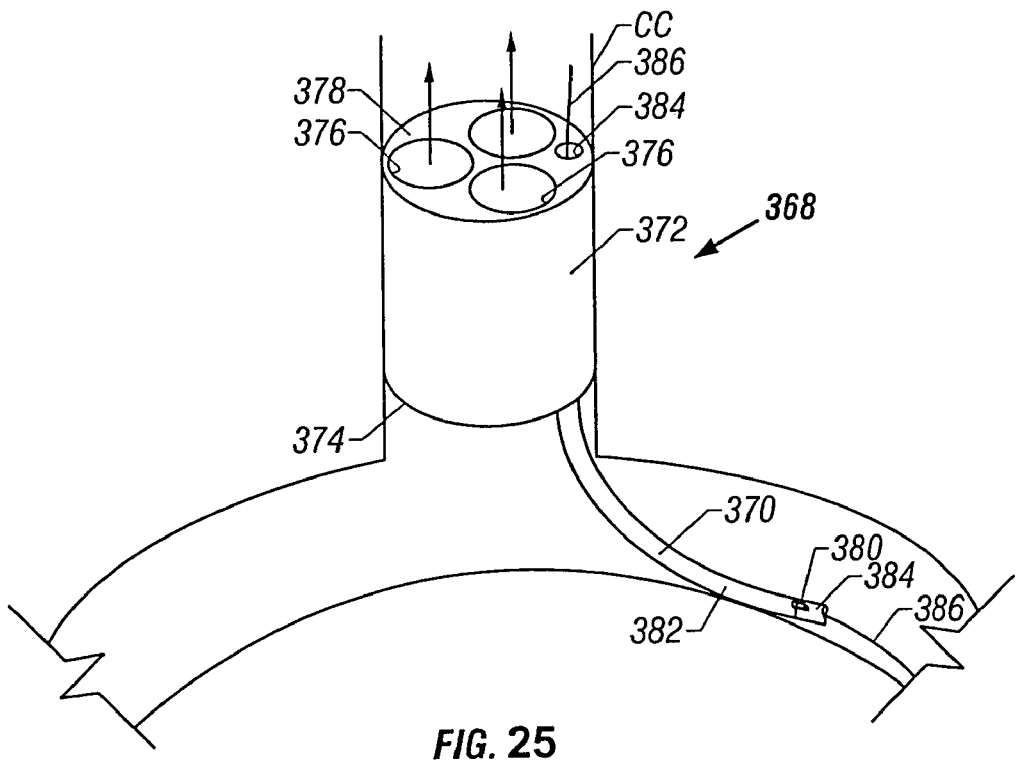
FIG. 25 is a perspective view of a further embodiment of the device of the present invention in place in a blood vessel of a patient.

As shown in FIG. 25, in another embodiment of the invention. the cooling apparatus 368 of the present invention includes a flexible multilumen catheter 370, an inflatable balloon 372, and a plurality of blood flow passageways 16 through the balloon 372. The balloon 372 is shown in an inflated state, in a selected position in a common carotid artery CC.

The balloon 372 is attached near a distal end of the flexible catheter 370. The catheter 370 can have at least a cooling fluid supply lumen 380 and a cooling fluid return lumen 382, with the cooling fluid supply lumen 380 preferably being located substantially within the cooling fluid return lumen 382. The catheter 370 can also have a guidewire lumen 384, for the passage of a guidewire 386, as is known in the art.

The balloon 372 can be formed from a flexible material, such as a polymer. The balloon 372 can be constructed to assume a substantially cylindrical shape when inflated, with a proximal aspect 374 and a distal aspect 378. The balloon 372 can have a plurality of tubular shaped blood flow passageways 376 formed therethrough, from the proximal aspect 374 to the distal aspect 378. The tubular walls of the passageways 376 constitute a heat transfer surface, for transferring heat from the blood to the cooling fluid. The flexible material of the tubular passageways 376 can be, at least in part, a metallized material, such as a film coated with a thin metal layer, either internally, externally, or both, to aid in heat transfer through the passageway walls. Alternatively, the tubular passageways 376 can be constructed of a metal-loaded polymer film. Further, the remainder of the balloon 372 can be coated with a thin metallized layer, either internally, externally, or both, or a metal-loaded polymer film. The proximal aspect 374 and the distal aspect 378 of the balloon can also constitute a heat transfer surface, for transferring heat from the blood to the cooling fluid. The guidewire lumen 384 of the catheter 370 can also pass through the balloon 372, from the proximal aspect 374 to the distal aspect 378.

Figure 26:
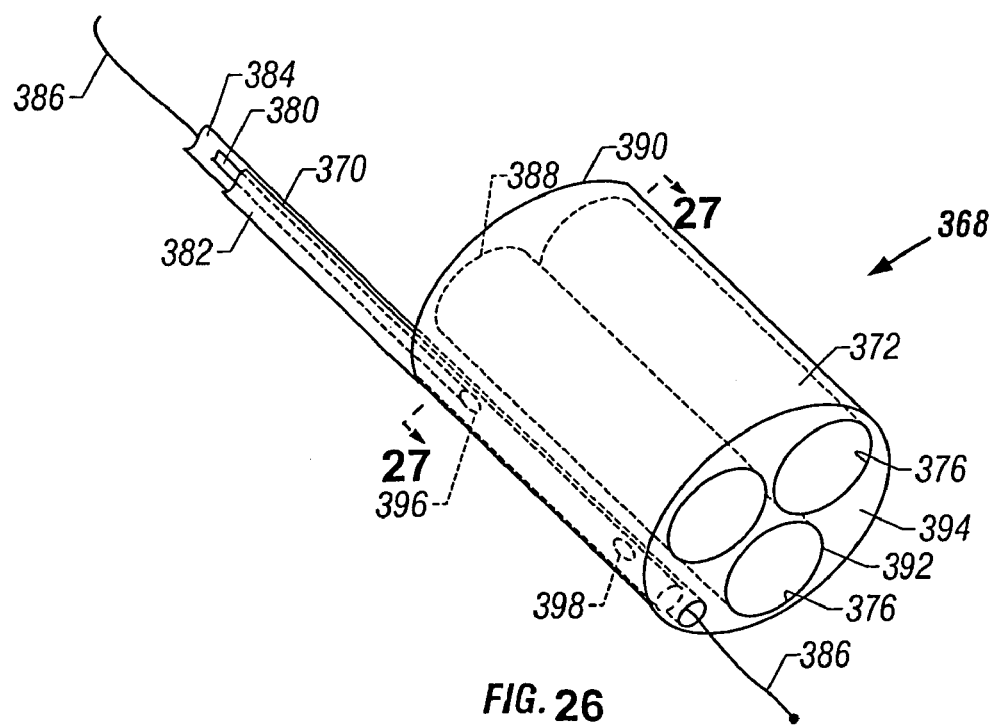
FIG. 26 is another perspective view of the device shown in FIG. 25, with additional details of construction.

As shown in FIG. 26, each tubular passageway 376 has a proximal port 388 in a proximal face 390 on the proximal aspect 374 of the balloon 372, and a distal port 392 in a distal face 394 on the distal aspect 378 of the balloon 372. A cooling fluid supply port 396 near the distal end of the cooling fluid supply lumen 380 supplies chilled saline solution from a chiller (not shown) to the interior of the balloon 372, surrounding the blood flow passageways 376. A cooling fluid return port 398 in the cooling fluid return lumen 382 returns the saline solution from the interior of the balloon 372 to the chiller. Relative placement of the cooling fluid ports 396, 398 can be chosen to establish flow counter to the direction of blood flow, if desired.

Figure 27:
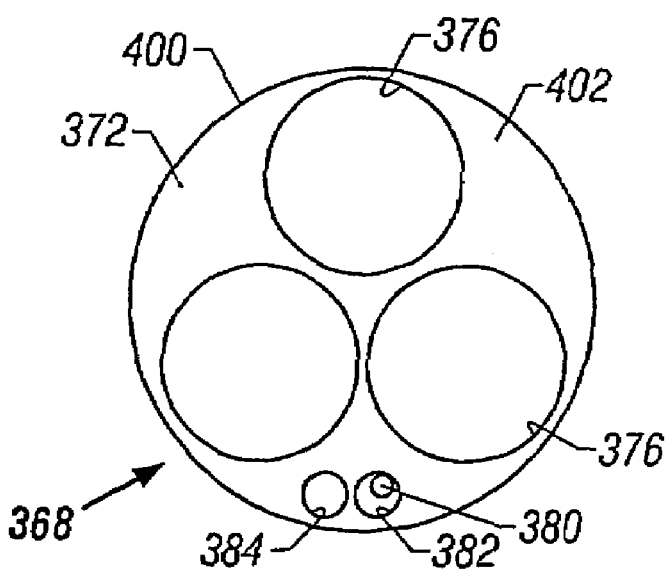
FIG. 27 is a transverse section view of the device shown in FIG. 26, along the section line 27-27.

FIG. 27 shows the proximal aspect 402 of the balloon 372 and gives a view through the blood flow passageways 376, illustrating the general arrangement of the blood flow passageways 376, cooling fluid supply lumen 380, cooling fluid return lumen 382, and guidewire lumen 384, within the outer wall 400 of the balloon 372.

Figure 28:
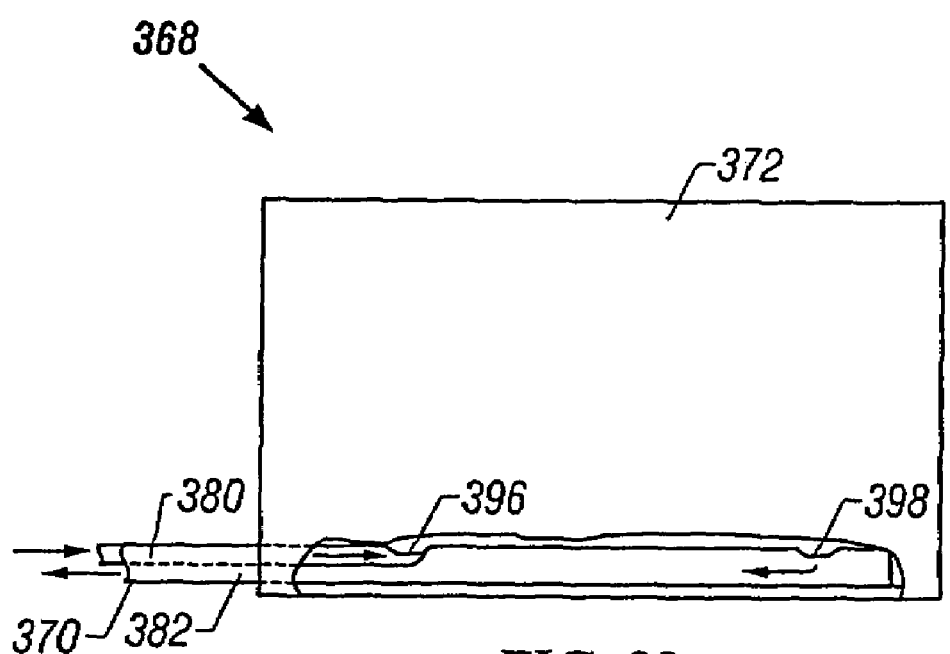
FIG. 28 is a partial longitudinal section view of the device shown in FIG. 25, showing the flow path of the cooling fluid.

FIG. 28 is a side elevation view of the apparatus 368, with a partial longitudinal section through the balloon wall 400, showing one possible arrangement of the cooling fluid supply port 396 and the cooling fluid return port 398 within the balloon 372.

In practice, the balloon 372, in a deflated state, is passed through the vascular system of a patient on the distal end of the catheter 370, over the guidewire 386. Placement of the guidewire 386 and the balloon 372 can be monitored fluoroscopically, as is known in the art, by use of radiopaque markers (not shown) on the guidewire 386 and the balloon 372. When the balloon 372 has been positioned at a desired location in the feeding artery of a selected organ, such as in the common carotid artery feeding the brain, fluid such as saline solution is supplied through the cooling fluid supply lumen 380. This fluid passes through the cooling fluid supply port 396 into the interior of the balloon 372, surrounding the tubular passageways 376, to inflate the balloon 372. Although the balloon 372 can be formed to assume a substantially cylindrical shape upon unconstrained inflation, the balloon 372 will essentially conform to the shape of the artery within which it is inflated. As the balloon 372 inflates, the blood flow passageways 376 open, substantially assuming the tubular shape shown.

When the balloon 372 has been properly inflated, blood continues to flow through the feeding artery CC by flowing through the blood flow passageways 376, as indicated, for example, by the arrows in FIG. 25. The size and number of the blood flow passageways 376 are designed to provide a desired amount of heat transfer surface, while maintaining a suitable amount of blood flow through the feeding artery CC. Return flow to the chiller can be established, to allow flow of cooling fluid through the cooling fluid return port 398 and the cooling fluid return lumen 382 to the chiller. This establishes a continuous flow of cooling fluid through the interior of the balloon 372, around the blood flow passageways 376. The return flow is regulated to maintain the balloon 372 in its inflated state, while circulation of cooling fluid takes place. The saline solution is cooled in the chiller to maintain a desired cooling fluid temperature in the interior of the balloon 372, to impart a desired temperature drop to the blood flowing through the tubular passageways 376. This cooled blood flows through the feeding artery to impart the desired amount of cooling to the selected organ. Then, cooling fluid can be evacuated or released from the balloon 372, through the catheter 370, to deflate the balloon 372, and the apparatus 368 can be withdrawn from the vascular system of the patient.

Temperature Sensing

A guidewire may also be employed to assist in installing the device. The tip of the guidewire may contain or be part of a temperature monitor. The temperature monitor may be employed to measure the temperature upstream or downstream of the heat transfer element and catheter, depending on the direction of blood flow relative to the temperature monitor. The temperature monitor may be, e.g., a thermocouple or thermistor.

An embodiment of the invention may employ a thermocouple which is mounted on the end of the guidewire. For the temperatures considered in blood heating or cooling, most of the major thermocouple types may be used, including Types T, E, J, K, G, C, D, R, S, B.

In an alternative embodiment, a thermistor may be used which is attached to the end of the guidewire. Thermistors are thermally-sensitive resistors (or "RTD"s, resistance temperature devices) whose resistance changes with a change in body temperature. The use of thermistors may be particularly advantageous for use in temperature-monitoring of blood flow past cooling devices because of their sensitivity. For temperature monitoring of body fluids, thermistors that are mostly commonly used include those with a large negative temperature coefficient of resistance ("NTC"). These should ideally have a working temperature range inclusive of 25° C. to 4° C. Potential thermistors that may be employed include those with active elements of polymers or ceramics. Ceramic thermistors may be most preferable as these may have the most reproducible temperature measurements. Most thermistors of appropriate sizes are encapsulated in protective materials such as glass. The size of the thermistor, for convenient mounting to the guidewire and for convenient insertion in a patient's vasculature, may be about or less than 15 mils. Larger thermistors may be used where desired. Of course, various other temperature-monitoring devices may also be used as dictated by the size, geometry, and temperature resolution desired.

A signal from the temperature-monitoring device may be fed back to the source of working fluid to control the temperature of the working fluid emerging therefrom. In particular, a catheter may be connected to a source of working fluid. A proximal end of a supply lumen defined by a supply tube is connected at an output port to the source of working fluid. The return lumen defined by a return tube is similarly connected at an input port to the source of working fluid. The source of working fluid can control the temperature of the working fluid emerging from the output port. A signal from a circuit may be inputted to the source of working fluid at an input. The signal from the circuit may be from the thermocouple, or may alternatively be from any other type of temperature-monitoring device, such as, as noted above, at the tip of the guidewire.

The signal may advantageously be employed to alter the temperature, if necessary, of the working fluid from the source. For example, if the temperature-monitoring device senses that the temperature of the blood flowing in the vessel of the patient's vasculature is below optimal, a signal may be sent to the source of working fluid to increase the temperature of the working fluid emerging therefrom. The opposite may be performed if the temperature-monitoring device senses that the temperature of the blood flowing in the feeding vessel of the patient's vasculature is above optimal.

Console

Figure 29:
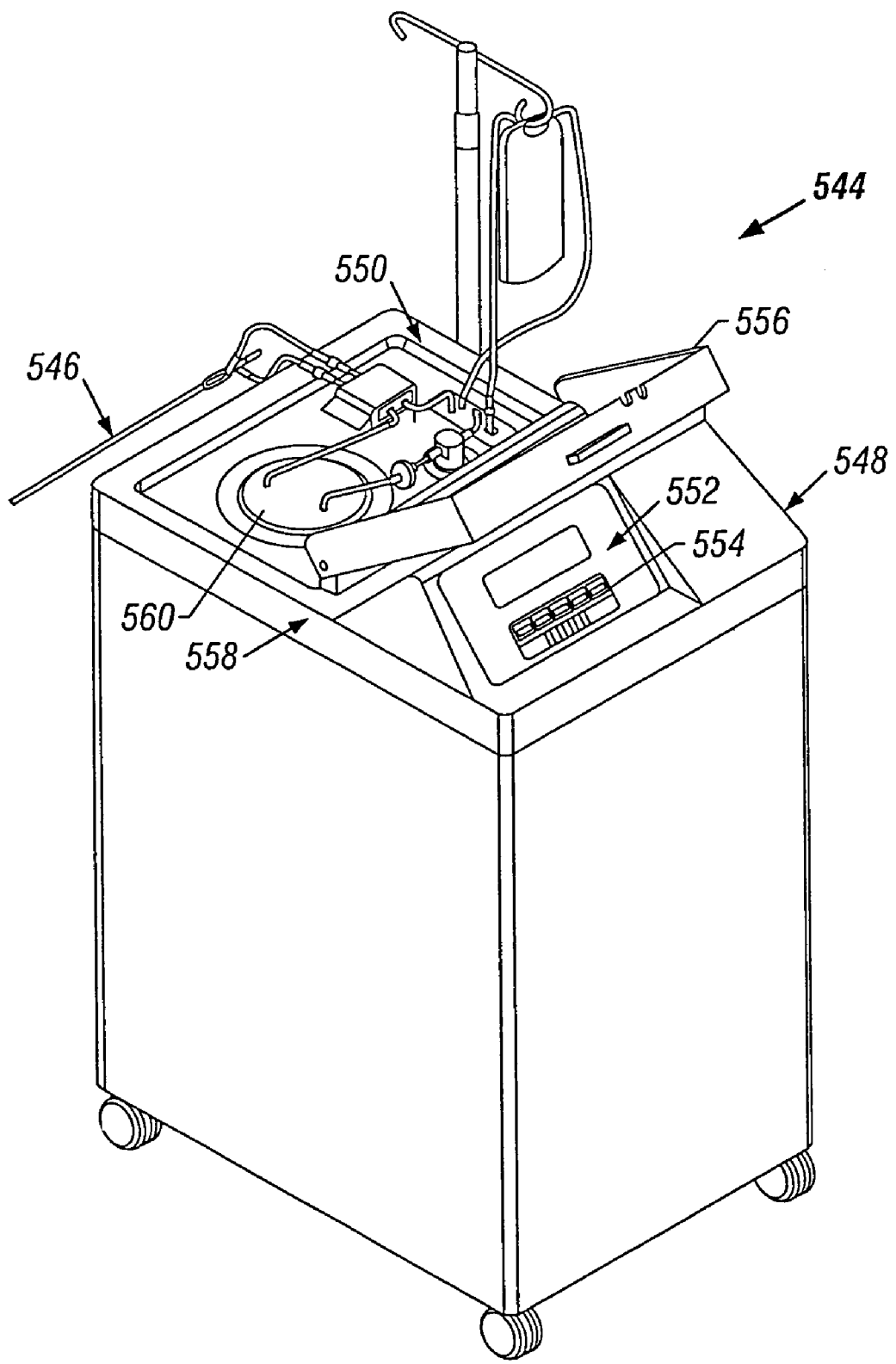
FIG. 29 is a perspective view of a console system including a circulation set constructed in accordance with an embodiment of the invention.

With reference to FIG. 29, an embodiment of a console system 544 includes a heat transfer catheter 546, a control system 548, and a circulation set 550 housed by the control unit system 548. The control system 548 may be equipped with an output display 552 and input keys 554 to facilitate user interaction with the control system 548. A hood 556 may be pivotally connected to a control unit housing 558 for covering much of the circulation set 550.

Circulation Set

Figure 30:
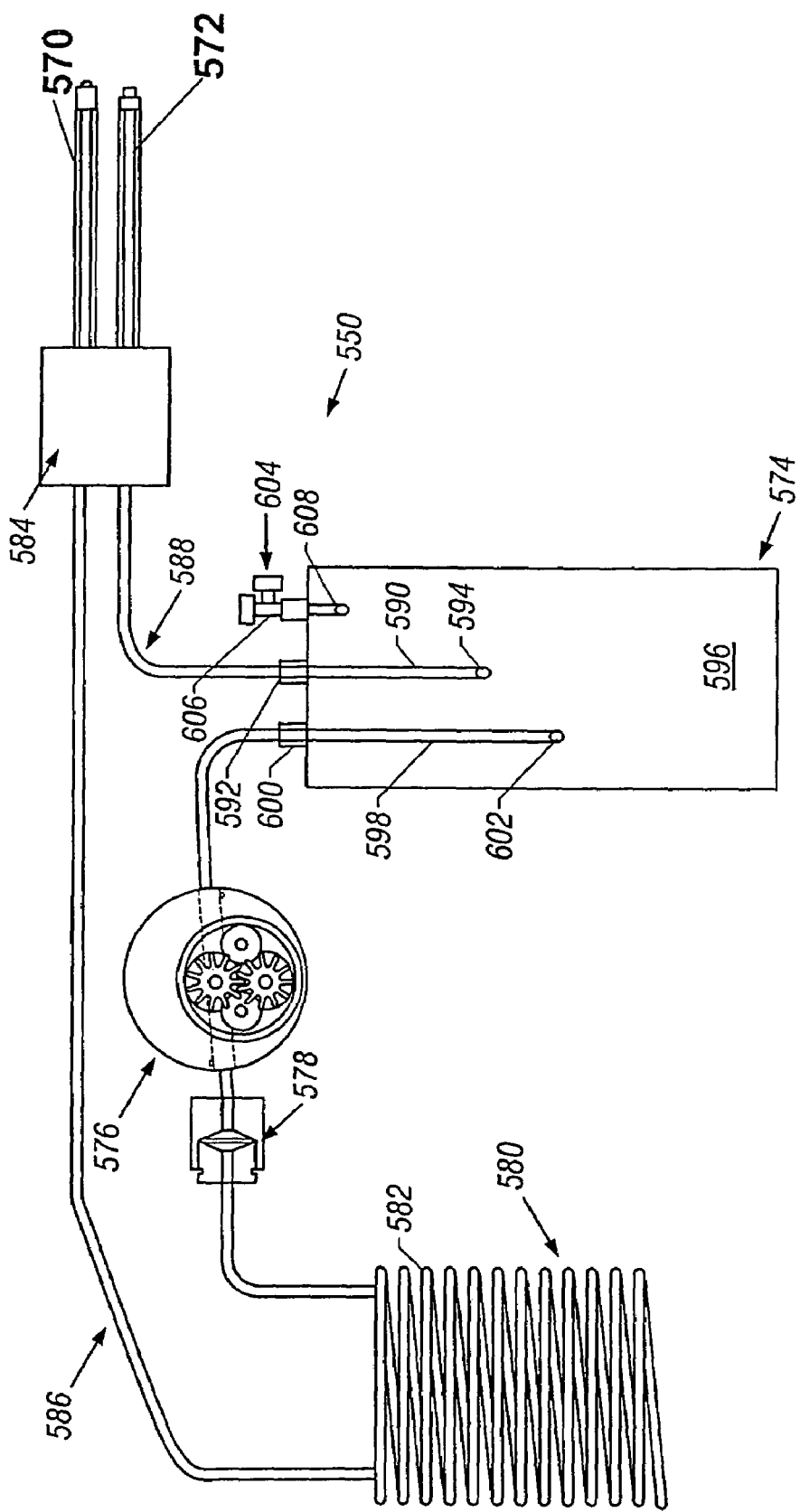
FIG. 30 is a schematic diagram of a circulation set according to an embodiment of the invention.

With reference to FIGS. 29 and 30, an embodiment of the circulation set 550 will now be described. The circulation set 550 include one or more of the following: a fluid reservoir 574, a pump 576, a filter 578, a heat exchanger 580, a temperature and pressure sensor assembly 584, a supply line 586, and a return line 588. A supply lumen port 570 and a return lumen port 572 are coupled to respective supply lines 586 and return lines 588 of the circulation set 550. The supply line 586 and return line 588 are preferably comprised of one or more pieces of tubing, connectors, etc. for joining the aforementioned components of the circulation set 550 to the supply lumen port 570 and return lumen port 572. The circulation set 550 may supply, filter, circulate, and/or be used to monitor the temperature and pressure of the heat transfer fluid for the catheter 546

Temperature Monitoring

Closed loop control of thermal therapy such as that provided by the system requires feedback of a temperature signal which represents the state of the patient, human or animal, to which the therapy is applied. This signal, combined with the target temperature of the therapy, serves as an input to a PID type control algorithm which regulates the energy added to or removed from the patient.

In such a system, the servo gain may be set to deliver maximum system power with approximately a 0.2 C servo error. With a PID controller, having zero coefficients for the integral and derivative terms, the controller may provide a proportional linear drive signal from 0% power, with a servo error=0° C., to 100% power with a servo error of 0.2 C. or more.

Choosing the correct physiologic site for acquisition of this feedback signal is important to the success of the therapy. Since the thermal modifications induced by the system are applied directly to the core of the patient, the control signal should ideally represent the thermal state (temperature) of the core compartment. With current clinically accepted temperature monitoring practice, core temperature is available through esophageal or naso-esophageal, tympanic, bladder, or rectal probes. While any of these may represent the temperature of a patient in equilibrium with the environment (i.e. one not subject to rapid temperature change), certain locations, such as bladder and rectal temperatures, described in more detail below, have been shown to lag the response of the core during intervals of rapid core temperature change. Additionally, esophageal, naso-esophageal, and tympanic probes may be acceptable for use in heavily sedated patients but are uncomfortable or otherwise impractical for use in lightly sedated or awake patients. In some instances, monitoring temperature in the distal esophagus is appropriate for monitoring core body temperature of a patient and for providing temperature feedback for controlling the induction and maintenance of hypothermia. However, for some patients, including stroke and AMI patients, esophageal temperature monitoring is not practical as these patients are often awake.

Other monitoring sites may be employed, including tympanic and bladder. However, even these monitoring sites are not ideal. For example, a tympanic temperature probe may cause patient discomfort and may be pulled out during the monitoring period. If this happens, the system will turn off as the patient temperature is already being measured as hypothermic at room temperature. The bladder temperature probe does not represent in real time the dynamic temperature changes that are occurring in the core. There is a significant lag of time, such as a 20 to 40 minute delay, and an effect of 1 to 2° C. that may make the same not represent the true core temperature.

Thus, to induce and control hypothermia in an awake patient requires a more reliable and accurate monitoring site that is not too invasive. A pulmonary artery (PA) temperature sensor located in a Swan-Ganz pulmonary artery catheter could be a reliable temperature site, but this requires another invasive catheter procedure, which is not indicated for stroke patients. Alternatively, a central venous catheter could measure the temperature of the blood entering the right atrium, but again this may be too invasive.

A sensor mounted on the interior of the catheter would address both of these problems by eliminating the need for a separate invasive temperature probe and ensuring accurate control temperature measurement due to the central placement of the catheter in the IVC. Since the temperature inside the catheter and its external environment may typically differ by 10-40° C. during operation, due to the presence of warm or cold heat transfer fluid within the catheter, acquisition of an accurate control temperature from a catheter mounted probe, such as a thermistor, may involve temporary cessation of therapy by halting the flux of heat transfer fluid. After the flux of heat transfer fluid is halted, a finite interval may elapse before thermal equilibration or relaxation of the catheter with its environment. Interrupting therapy for acquisition of the control temperature may tend to reduce the accuracy of the controller. A predictive algorithm allows computation of a useful control temperature which does not require waiting for complete equilibration and thus measurement of patient core temperature. One method for prediction of the equilibrium temperature, based on an assumed functional form for the relaxation history, is presented below.

In one embodiment, as an initial calculation, by measuring the temperature of the catheter working fluid returning to the console, one can determine or estimate the power delivered or consumed by the catheter's heat exchanger.

For example, $$P_{delivered\ to\ catheter} = (T_R - T_s) \cdot (\text{flow rate}) \cdot 4.17\ W-°C.-cc/sec$$

This power is directly affected by the patient's temperature. Less power is delivered with a warmer core temperature than a colder one. In general, the power delivered is proportional to the temperature gradient between the patient's blood temperature and the temperature of the heat exchanger:

$$P_{delivered}\ (\text{Watts}) \propto f(T_{patient})$$

Going from a patient temperature of 37° C. to 33° C. would lower the power approximately $$1 - \frac{33 - 4°\ C.}{37 - 4°\ C.} \cong 12.1\%$$

Thus, by monitoring the decrease or increase in power applied or absorbed by the catheter, one can estimate a useful control temperature, or at least the blood temperature, indirectly. By knowing the starting patient temperature (e.g., the clinician could enter a value corresponding to the patient temperature via an IR ear thermometer) and programming in a desired patient temperature, the device could controllably cool or heat the patient. By monitoring the return temperature change, the instrument could control to the desired hypothermic state.

Figure 31:
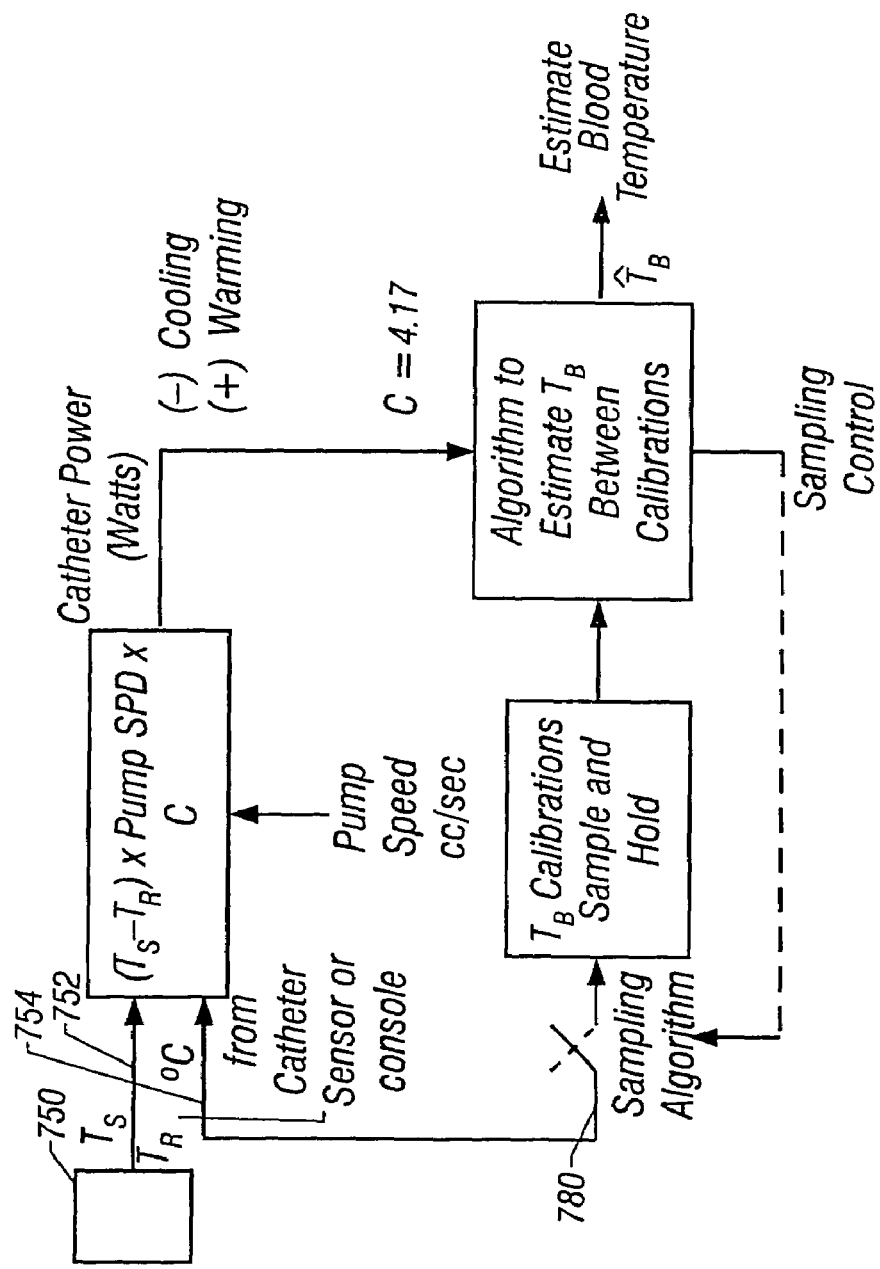
FIG. 31 shows a system that may be used to implement a predictive temperature algorithm.

Referring to FIG. 31, the console 750 may measure the temperature of the catheter "coolant" or working fluid in both directions: i.e., the temperature of the fluid 752 being supplied Ts to the catheter and the temperature of the fluid 754 returning from the catheter TR. This temperature may be measured at the console 750 via, e.g., thermistor pins that interface with a disposable circulation set.

Figure 32:
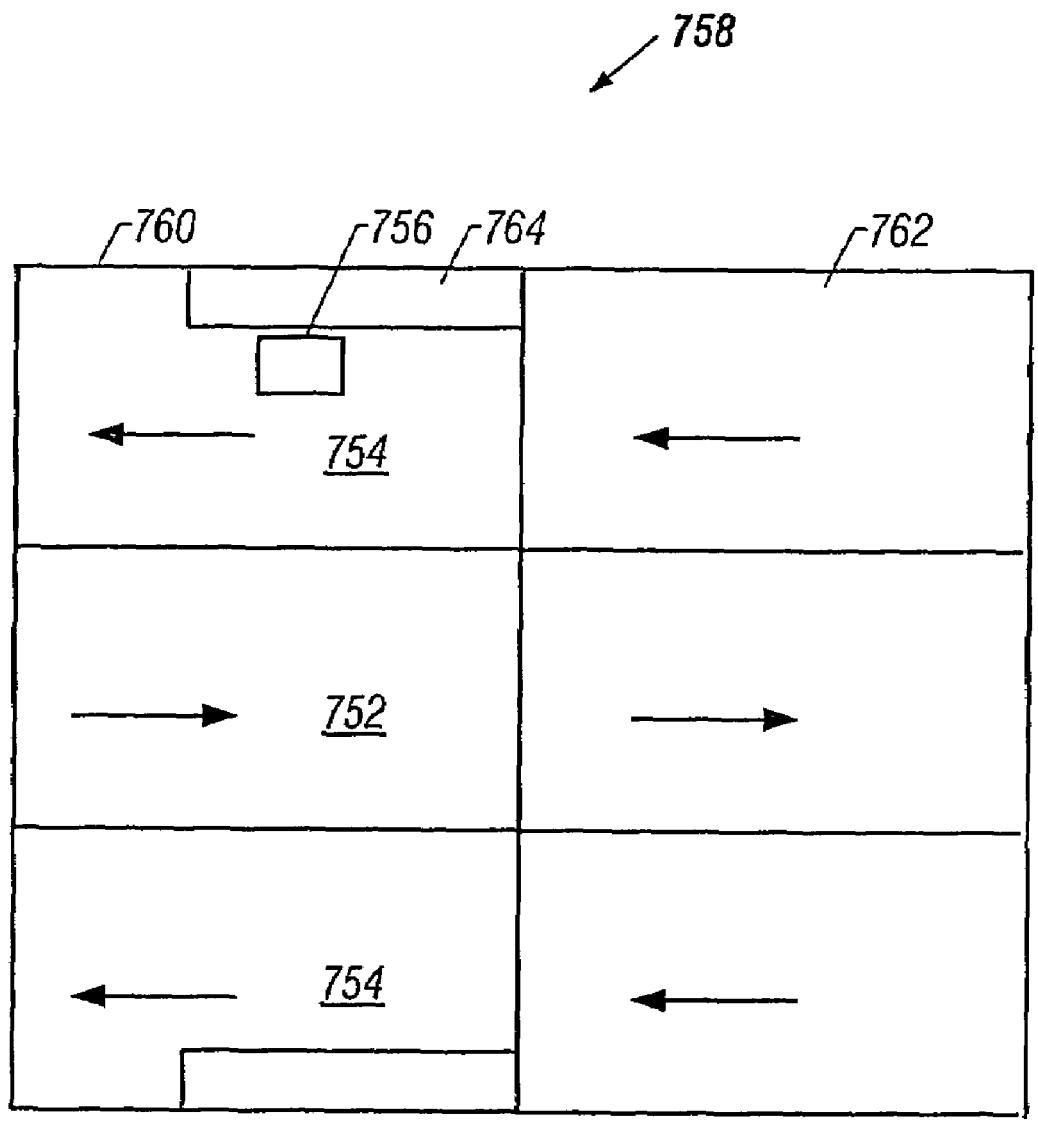
FIG. 32 shows a junction between a heat transfer element and a catheter showing position of a catheter-mounted heat transfer element.

Another way to measure the latter temperature, e.g., the catheter coolant return temperature, is to mount a temperature sensor 756 in the catheter heat transfer element 758 in the return lumen 760 of the catheter (see FIG. 32). This may yield a more precise measurement.

Figure 33:
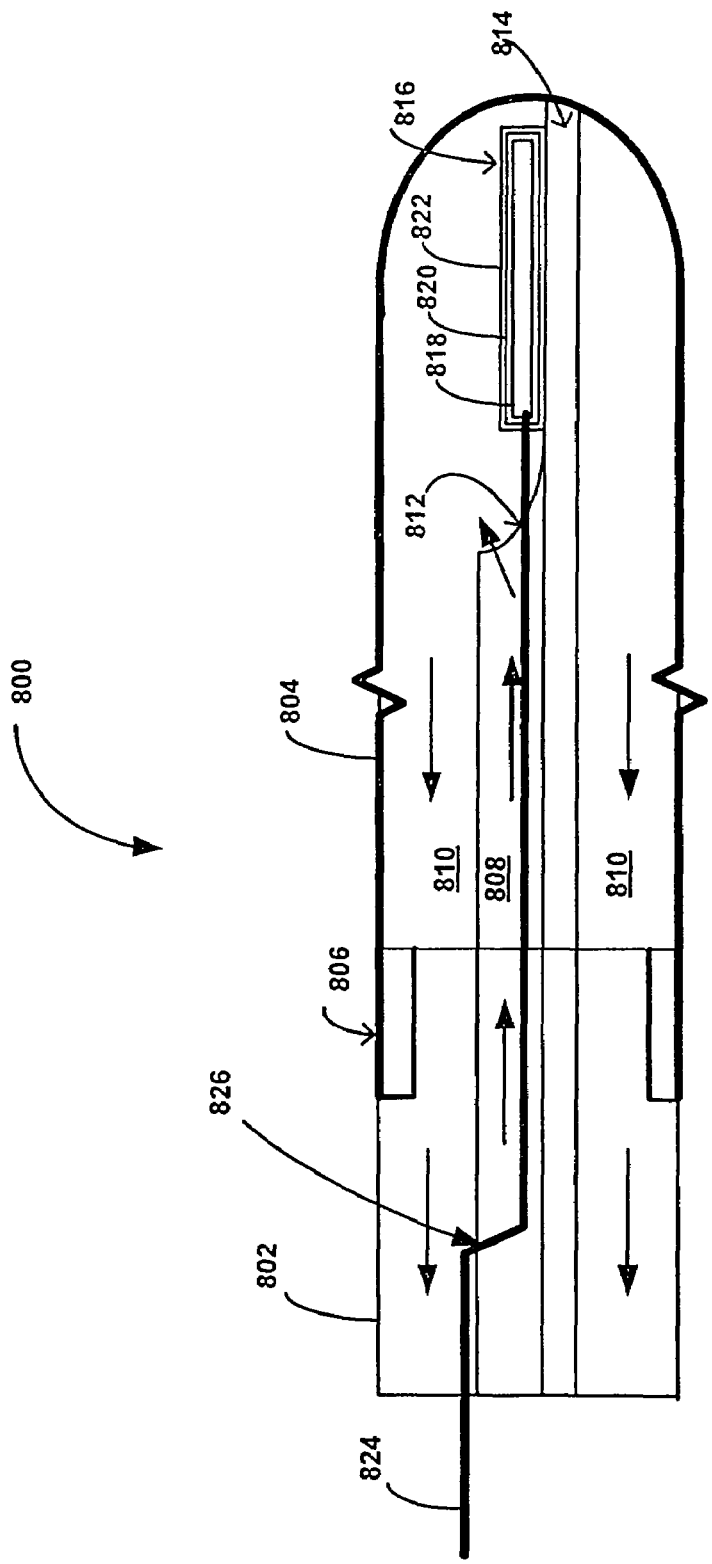
FIG. 33 shows a heat transfer element and catheter showing position of a distal tip catheter-mounted temperature sensor.

FIG. 33, described in more detail below, shows an alternate embodiment where a distal-tip-mounted temperature sensor is employed. By measuring the coolant return temperature $T_R$ in the catheter at the HTE, one can measure the instantaneous power absorbed or delivered to the blood stream. This power may be proportional to the actual blood temperature. In the cooling mode, as the blood temperature decreases, the power delivered to the catheter decreases since the temperature gradient is less. This is also true, in the converse sense, in the rewarming mode. As the patient warms, less power is delivered to the blood stream. This relationship can be approximated by $$\Delta power_{absorbed/delivered} \cong \frac{T_{patient_1} - T_{bath_1 return}}{T_{patient_2} - T_{bath_2 return}}$$

$$T_{patient_N} = \text{patient blood temperature near catheter heat exchanger at time } N$$

$$T_{bath_N} \text{ return} = \text{Temperature of coolant returning (console) at time } N \text{ or as measured at the to the heat exchanger catheter heat exchanger}$$

The console 750 can measure the instantaneous power that is being delivered or absorbed by the catheter 762, and by monitoring the change in power delivered as cooling or warming is being administered, one can predict or estimate a new control temperature value if the original temperature is known. Therefore, the following relationship exists:

New control temperature estimate α f(initial blood temperature, initial power, current power)

This relationship may have other sensitivities which alter "the change in catheter power" to "change in blood temperature" relationship. For example, if the blood flow changes dramatically during this period, the catheter heat exchanger efficiency may change. Higher cardiac outputs would allow for more power absorption or delivery.

To correct for this effect, the catheter coolant flow can be stopped and the HTE can come to equilibrium with the blood temperature. At this equilibrium, the temperature sensor on the HTE would be measuring the temperature of the blood. This measurement may be used to correct the estimate for future blood temperature predictions. A determination may then be performed as to how often it is necessary to stop the pump and recalibrate the algorithm that provides real time blood temperature estimates.

where:

$T_S$=Temperature of the coolant entering catheter $T_R$=Temperature of the coolant returning from the catheter $T_B$=Temperature of the blood indirectly estimated by turning off the flow of coolant in the catheter.

This method estimates the blood temperature between the "pump off" states and the run states.

Certain variables require a certain level of estimation. First, the pump needs to be "off" a set period of time to reach equilibrium with the blood flowing around the HTE.

For example, it may take 60 seconds to 120 seconds for the HTE outlet sensor to achieve a temperature equilibrium with the flowing blood.

Figure 34:
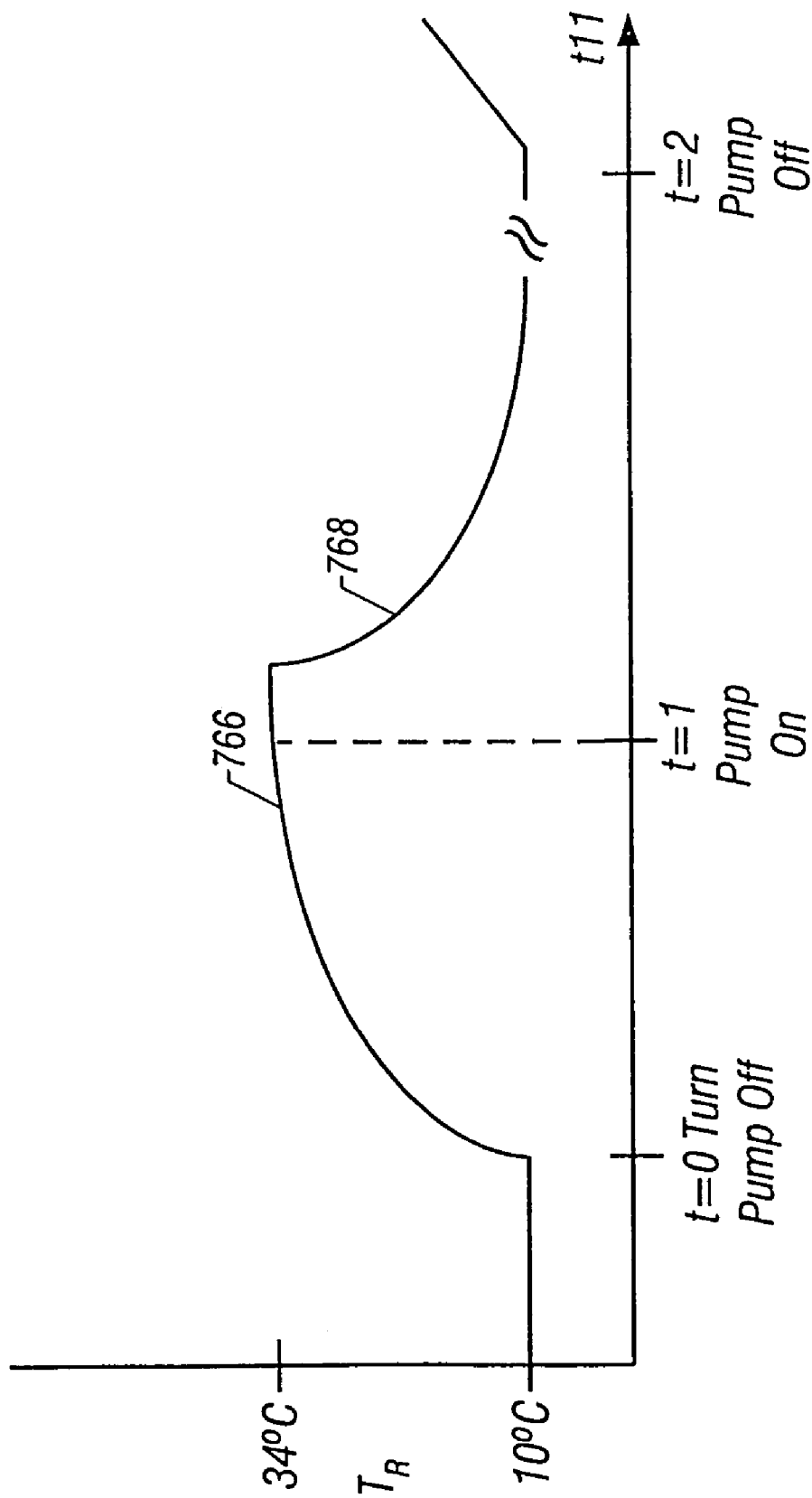
FIG. 34 shows a pump duty cycle.

In addition, an estimation algorithm can be employed to predict the steady state temperature. For example, referring to FIG. 34, the temperature measured by a catheter-mounted thermistor at a time of full pump activity may be, e.g., 10° C., at time t=0. If at this time the pump is turned off, the temperature as measured rises according to curve 766 up to an equilibrium temperature. If at time t=1 the pump is turned back on, then the temperature cools again according to curve 768. A duty cycle may be defined by:

$$duty\ cycle = \frac{pump\ 'on'\ time}{pump\ 'on'\ time + pump\ 'off'\ time}$$

A good duty cycle may be, e.g., >90%.

Figure 35:
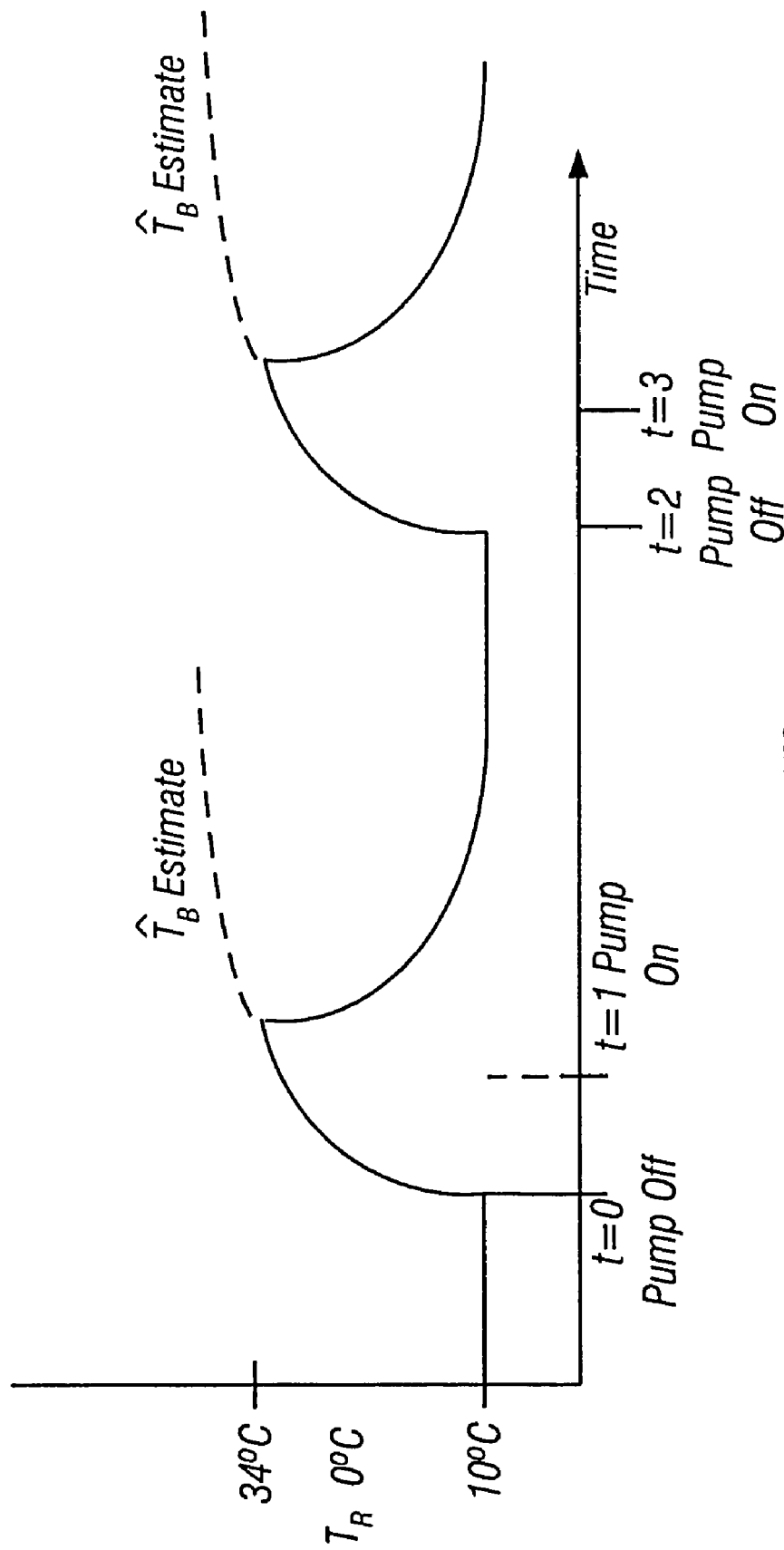
FIG. 35 shows two pump duty cycles and the achievement of a higher duty cycle, compared to that of FIG. 34, when a predictive temperature algorithm is employed.

The duty cycle can be enhanced, i.e., >90%, if a predictive algorithm is employed to shorten the time that the pump is off. Referring to FIG. 35, an algorithm that predicts the control temperature allows the measurement of temperature to occur in a shortened span of time, thus shortening the pump "off" time and raising the duty cycle. The following example demonstrates the principle that the patient temperature can be altered, at least for a predetermined time, without constantly monitoring the patient temperature.

The patient core temperature can move somewhat during periods of maximum drive by the system. For example, it has been seen that an average cooling rate may be 5° C./hr and an average warming rate may be 2° C./hr. Assuming these values, in 10 minutes, the body temperature can change Δ 0.8° C. cool down/10 minutes and Δ 0.3° C. warmup/10 minutes After this initial interval, e.g., 10 minutes, the algorithm may sample more rapidly as it nears to the desired target value. For instance, if the patient initial temperature is 37° C. and the goal is 33° C., a 4° C. change, the device can anticipate that a minimum of 30 minutes to 45 minutes will be required to induce a 4° C. core temperature change. Thus, the device can start cooling with maximum power for 30 minutes, then stop the pump and check the temperature.

As the temperature nears the set point, sampling may be more frequent. Table I shows a sample sampling algorithm that changes the frequency of stopping the pump and measuring temperature as the temperature difference between patient target temperature and projected control or projected or measured blood temperature is lowered. Tables III and IV show more detailed analysis of the rates.

Temperature Sensor Located Within the HTE

EXAMPLE 1

Adjacent-Proximal-Bond-Mounted

Referring back to FIG. 32, a thermocouple 756, such as a "T" type, was bonded into the proximal bond 764 of the catheter's HTE 762 (e.g., a 14 fr. HTE). With the system running in the maximum cooling phase, the HTE sensor 756 was measuring a temperature of approximately 18° C. Upon stopping the circulation pump, the sensor's temperature rose exponentially to 37.4° C., with a time constant of approximately 10 to 12 seconds. The actual temperature read as a function of time is as per Table II.

As may be seen, stopping the pump for 30 seconds, the temperature sensor approached to approximately 0.3° C. of the final temperature. Stopping the pump for 20 seconds, the sensor will be short about 0.7° C. of the final value.

EXAMPLE 2

Tip-Mounted

Referring to FIG. 33, a catheter heat transfer tip assembly 800 is shown having a catheter tube 802 and a heat transfer tip 804 that are bonded together at a proximal bond 806. The assembly 800 includes a supply lumen 808 and a return lumen 810. Fluid within supply lumen 808 is in pressure communication with fluid within return lumen 810 via a skive 812. The directions of fluid flow are indicated by the arrows within lumens 808 and 810, although of course these may be reversed if desired. A guidewire lumen 814 may be disposed adjacent the supply lumen 808.

A thermocouple or thermistor assembly 816 may be disposed at or adjacent the distal tip of the heat transfer tip, such as by being bonded to the exterior of the guidewire lumen 814. The assembly 816 may include a thermistor or thermocouple 818, which may be encapsulated with a polymer sleeve 820 such as polyimide or polyethylene. Instead of or additionally, an encapsulation with a UV curable loctite adhesive (not shown) may take place. Finally, for strength, the encapsulated sensor may be placed into a hypotube 822, which may be a small stainless steel tube.

Sensor wires 824 may communicate signals from the temperature sensor to the control circuitry. As the wires are typically too large to fit in the return lumen 810, principally due to the bellows of the heat transfer tip, the same may traverse from the return lumen 810 (where they are disposed proximal of the proximal bond 806) to the supply lumen 808 (where they are disposed distal of the proximal bond 806). This traversal may occur at an entry point 826, which is generally a hole. This arrangement has an additional benefit that the wires are out of the high pressure supply lumen for most of their length.

EXAMPLE 3

Sheath-Mounted

In yet another embodiment, the temperature sensor may be mounted on the introducer sheath used for catheter installation. In this case, the temperature sensor would be disposed on a part of the sheath that is within the vascular system.

EXAMPLE 4

Balloon-Mounted

In yet another embodiment, the temperature sensor may be mounted on a portion of the helical balloon embodiment disclosed above. For example, the same may be mounted on the exterior of the balloon at the distal tip, to achieve a temperature reading most indicative of core body temperature. However, for convenience, the temperature sensor may also be mounted at various other locations, either on or within the balloon. In any case, the sensor may have a polymer shield and/or metallic shield discussed above. As in the other embodiments, flow may be interrupted for a short period of time to allow the temperature measured by the sensor to begin to relax to an equilibrium temperature, and from the temperatures measured during this relaxation a projection to measure a control temperature may be made.

Predictive Algorithm

Determination of Time Constant

The time constant of the response is proportional to the trapped volume of saline in the HTE. A 24 cm 14 fr. HTE will contain approximately the following amount of saline:

$$\frac{14 \text{ fr.}}{\Pi r^2 \times l} \cong \text{saline volume}$$

$$\Pi (0.23^2 \text{ cm}^2) \times 24 \text{ cm} \cong 4 \text{ cm}^3$$

A 24 cm 9 fr. HTE will contain approximately the following amount of saline:

$$\frac{9 \text{ fr.}}{V} = \Pi \times r^2 \times l = \Pi (0.15^2 \text{cm}^2) \times 24 \text{ cm} = 1.7 \text{ cm}^3$$

Therefore, the time constant of a 9 fr. dual element HTE should be $$\frac{1.7}{4} = 42.5\% \text{ of the 14 fr.} \approx 4 \text{ to 5 seconds}$$

Thus, for a 9 fr. catheter, the "pump off" time can be reduced to approximately 10 seconds to 15 seconds.

EXAMPLE PROCEDURE

1. Input the desired "target temperature" and rate if desired.
2. Estimate patient temperature from HTE sensor=$\hat{T}_{P_{(O)}}$ pump "off" for e.g., 30 seconds.
3. Device calculates "servo error"

$$\hat{T}_{patient_{(O)}} - T_{Target_{(O)}} = E(O).$$

4. Device determines time interval to cool or warm, depending on size of E(O) (see Table V).
5. Stop pump at the end of the heating/cooling interval.
6. Capture temperature data from HTE sensor at, e.g., 0.1 second sampling rates
   9 fr capture 15 seconds of data
   14 fr. capture 30 seconds of data
7. Estimate control temperature and display value. Input this value to the temperature control servo loop.
8. Start pump up depending on servo error (see Table VI):

$$\text{where ServoError} = \hat{T}_{patient(N)} - T_{Target(O)}$$

Alternatively, the pump power can be made proportional to the servo error.

An alternative method for determining the interval to drive the system before stopping the pump is as follows:

Assuming $T_o(t)$=Starting patient temperature; and $T_T$=Target temperature,

The maximum rate of cooling or heating $$\left| \frac{[T_o(t) - (T_t + 0.5°)]}{R_{max}° C./\min} \right| = \text{Time minutes}$$

Figure 36:
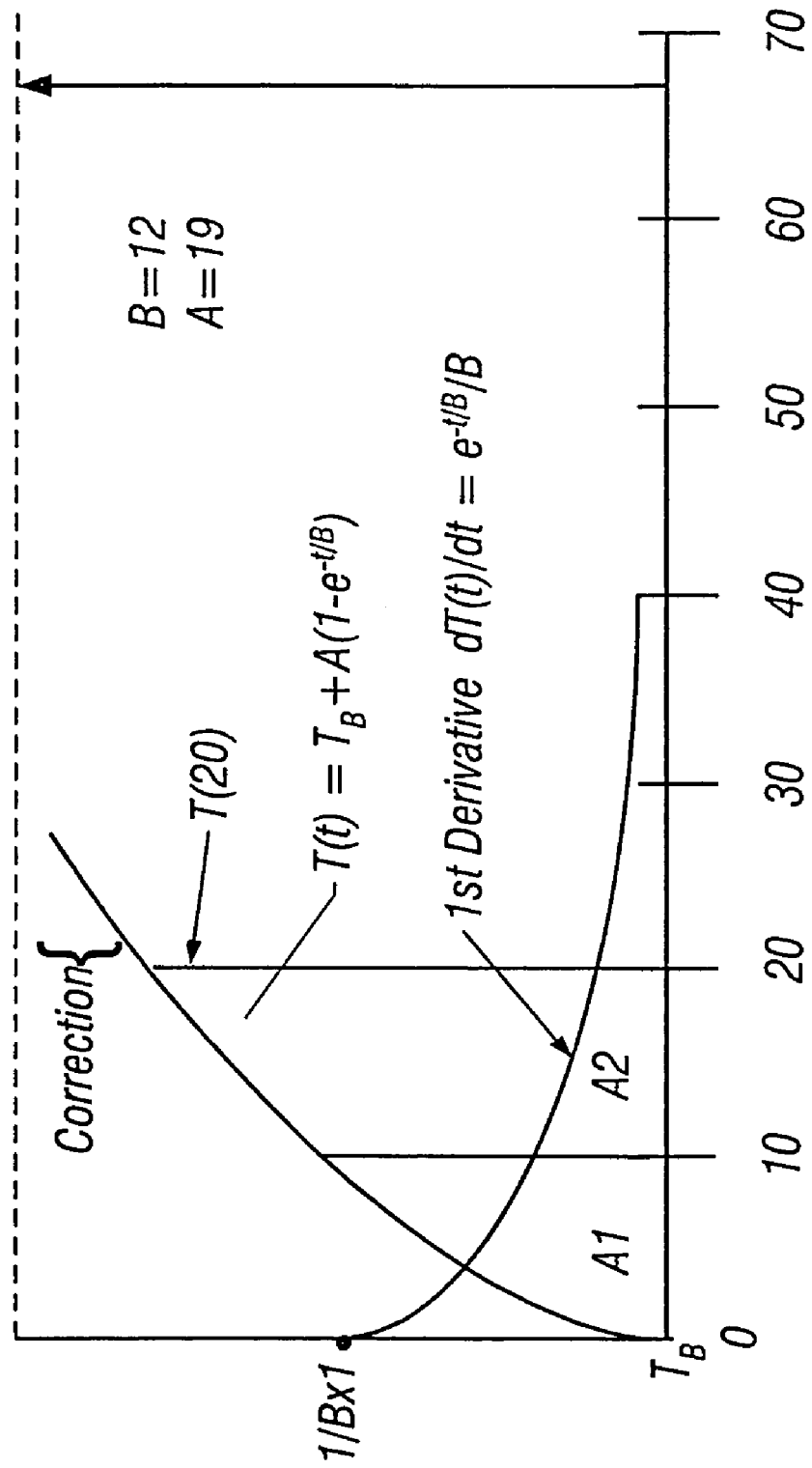
FIG. 36 shows one graphical method of predicting a control temperature.

One approach to determining a projected control temperature is as follows. Referring to FIG. 36, the exponential T(t) is shown. Area A1 is the area under T(t) during the first 10 seconds and Area A2 is the area under T(t) during the next 10 seconds.

If the assumption is made that $$\frac{A1}{A2} = \frac{\text{Area 1st 10 Seconds}}{\text{Area 2nd 10 Seconds}} \propto B,$$

a time constant; independent of A $$\frac{A1}{A2} = \frac{\int_0^{10} A\left(1 - e^{-\frac{t}{B}}\right)}{\int_{10}^{20} A\left(1 - e^{-\frac{t}{B}}\right)} \Rightarrow \frac{\int_0^{10} 1 - \int_0^{10} e^{-\frac{t}{B}}}{\int_0^{20} 1 - \int_0^{20} e^{-\frac{t}{B}}}$$

$$\frac{A1}{A2} = \frac{10 + Be^{-\frac{10}{B}} - Be^{-\frac{0}{B}}}{10 + Be^{-\frac{20}{B}} - Be^{-\frac{10}{B}}} =$$

Defining a unique relationship between $$\frac{A1}{A2} = f(B);$$

for every B, there is a well defined A1/A2 ratio $$\frac{A1}{A2} = \frac{10 + Be^{\frac{-10}{B}} - B}{10 + Be^{\frac{-20}{B}} - Be^{\frac{-10}{B}}}$$

Figure 37:
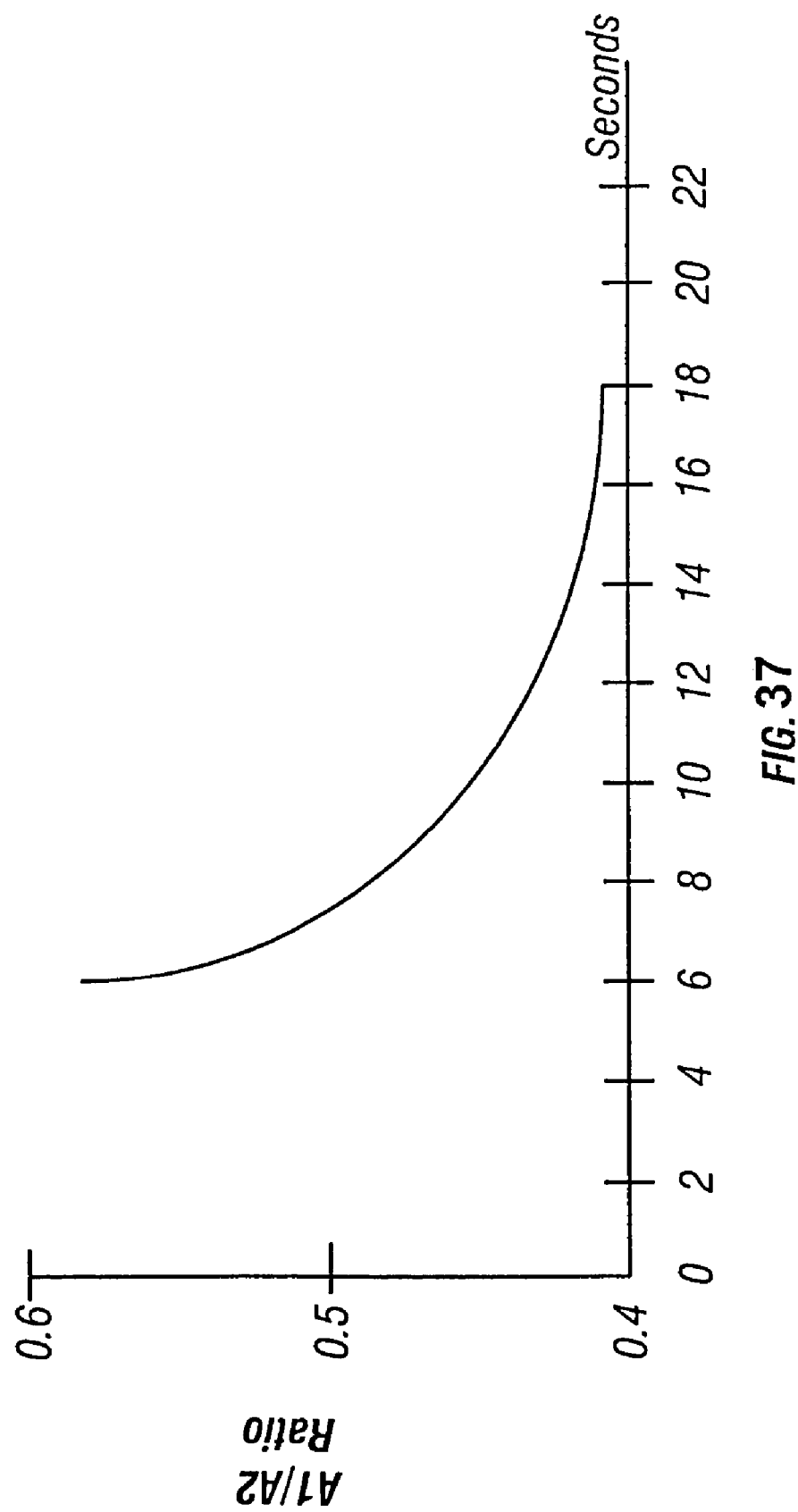
FIG. 37 shows the relationship of the ratio of areas, before measurement and after measurement, with respect to time.

A1 and A2 can be measured numerically. From this, B can be calculated. Of course, a look-up table can be instituted for ease of reference (see Table VII). Also see FIG. 37, in which each area A1 and A2 encompass 12 seconds sampling time.

Once B is determined from the look up table, A can be calculated as follows:

$$A1 + A2 = A\left[\int_0^{10}\left(1 - e^{-\frac{t}{B}}\right) + \int_0^{20}\left(1 - e^{-\frac{t}{B}}\right)\right]$$

$$A = \frac{A1 + A2}{20 + Be^{-\frac{20}{B}} - B}$$

The magnitude of correction can then be calculated.

$$T(t) = T_B + A(1 - e^{-t/B})$$

Temperature $T(t)$ at end of $A1 + A2$, $t = 20$ $$T(20) = T_B + \hat{A}\left(1 - e^{-20/\hat{B}}\right)$$

at $$T(\infty) = T_B + \hat{A}$$

or $$T(\infty) = T(20) + \Delta T \text{ correction}$$

$$\Delta T \text{ correction} = \hat{A} e^{-20/\hat{B}}$$

@ $t = 20$ $$\hat{T}\infty = T(20) + \hat{A} e^{-20/\hat{B}}$$

Estimated final value

Figure 38:
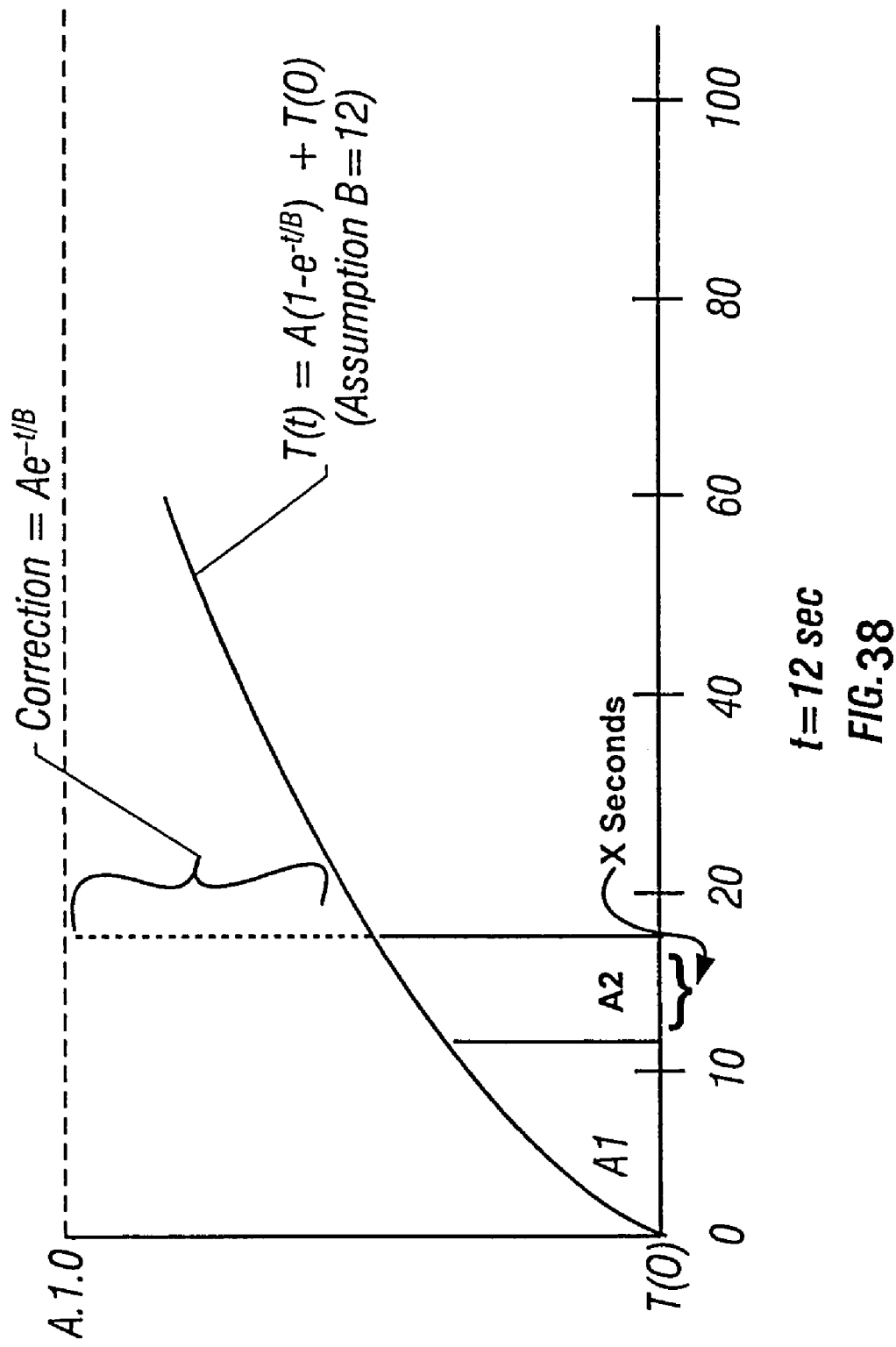
FIG. 38 shows another method of predicting a control temperature.

Referring to FIG. 38, which changes the above to the case where A1 and A2 encompassing non-equal time periods but equal areas:

$$A1 = \int_0^{12}(1 - e^{-t/B})dt = \int_0^{12} dt - \int_0^{12} e^{-t/B}dt = 12 + Be^{-12/B} - B$$

$$= 12 + 12e^{-1} - 12 = 12 - 0.367 = 4.4$$

$$A1 = 4.4^\circ \text{ C.} - \text{sec}$$

$$A2 = \int_{12}^{x}(1 - e^{-t/B})dt = \int_{12}^{x} dt - \int_{12}^{x} e^{-t/B}dt = (x - 12) + Be^{-x/B} - Be$$

$$A2 = x - 12 + B(e^{-x/B} - e^{-12/B})$$

Find x for which $A1_{12}$ sec=A2

$$\frac{A1}{12 \text{ sec}} = 12 + B_e^{-12/B} - B = \frac{A2}{12 - x} = x - 12 + Be^{-x/B} - Be^{-12/B}$$

$$\Rightarrow 24 + 2Be^{-12/B} - B = x + Be^{-x/B}$$

One can then solve x for certain B's, creating a look up table which defines the range of possible time constants for a given catheter.

Figure 39:
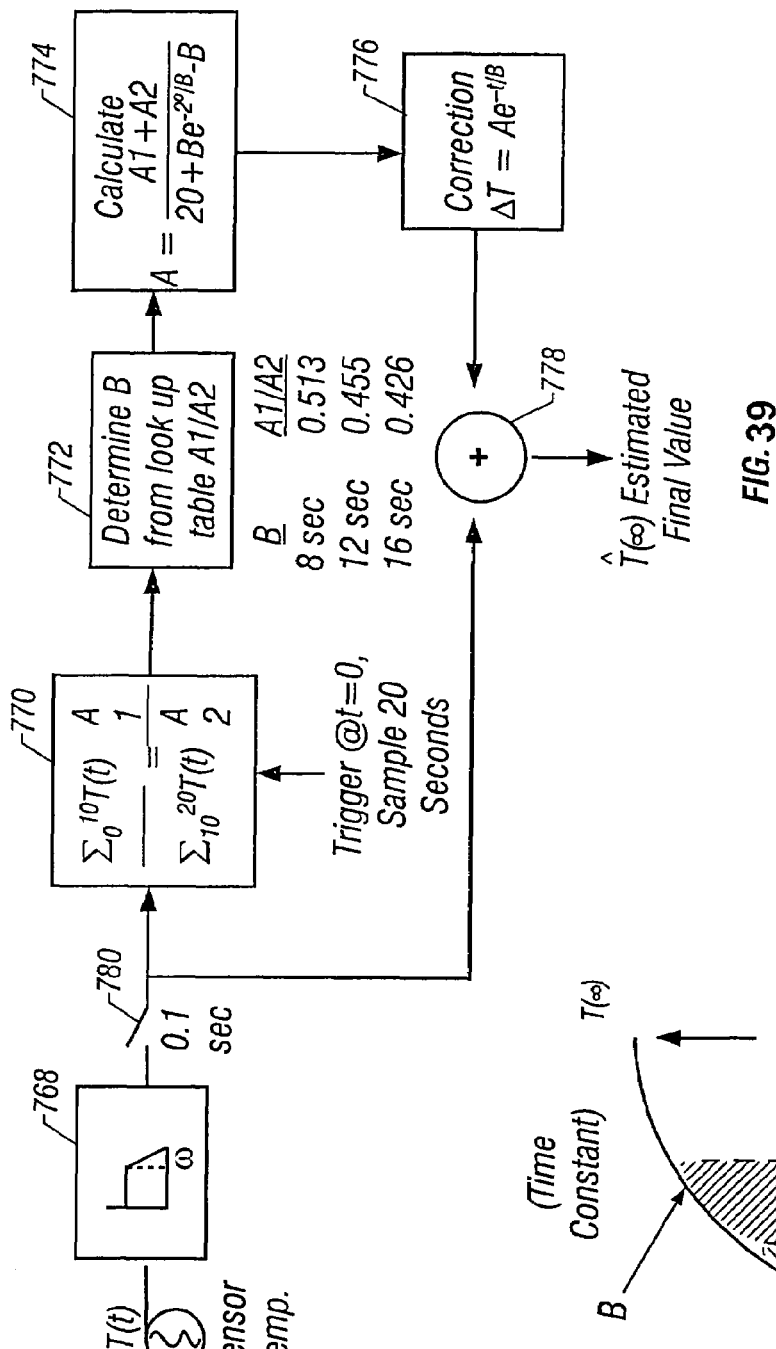
FIG. 39 shows a system that may implement a method of predicting control temperatures.

To implement the above, a device such as that schematically shown in FIG. 39 may be employed. In FIG. 39, sensor temperature T(t) is measured by switch 780 when the pump is shut off (stop 768). In FIG. 39, a sampling interval of 0.1 seconds is shown, but this can vary.

Figure 40:
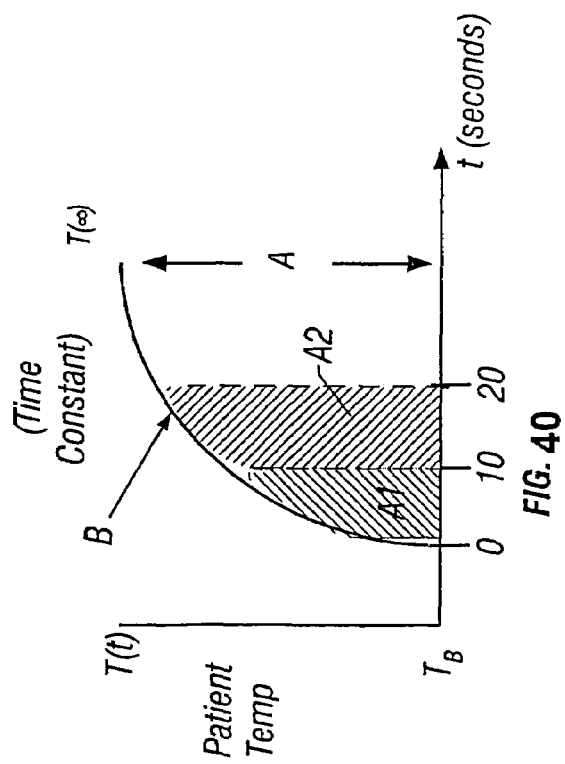
FIG. 40 shows a graph of the areas of, e.g., FIG. 37.

The calculation of A1/A2 proceeds next (step 770), followed by the determination of B from the look-up table (step 772). A is then calculated (step 774), and from this ΔT, i.e., the correction factor (step 776). The projected temperature T(∞) may then be determined (step 778). The various quantities discussed are shown in FIG. 40.

Figure 41:
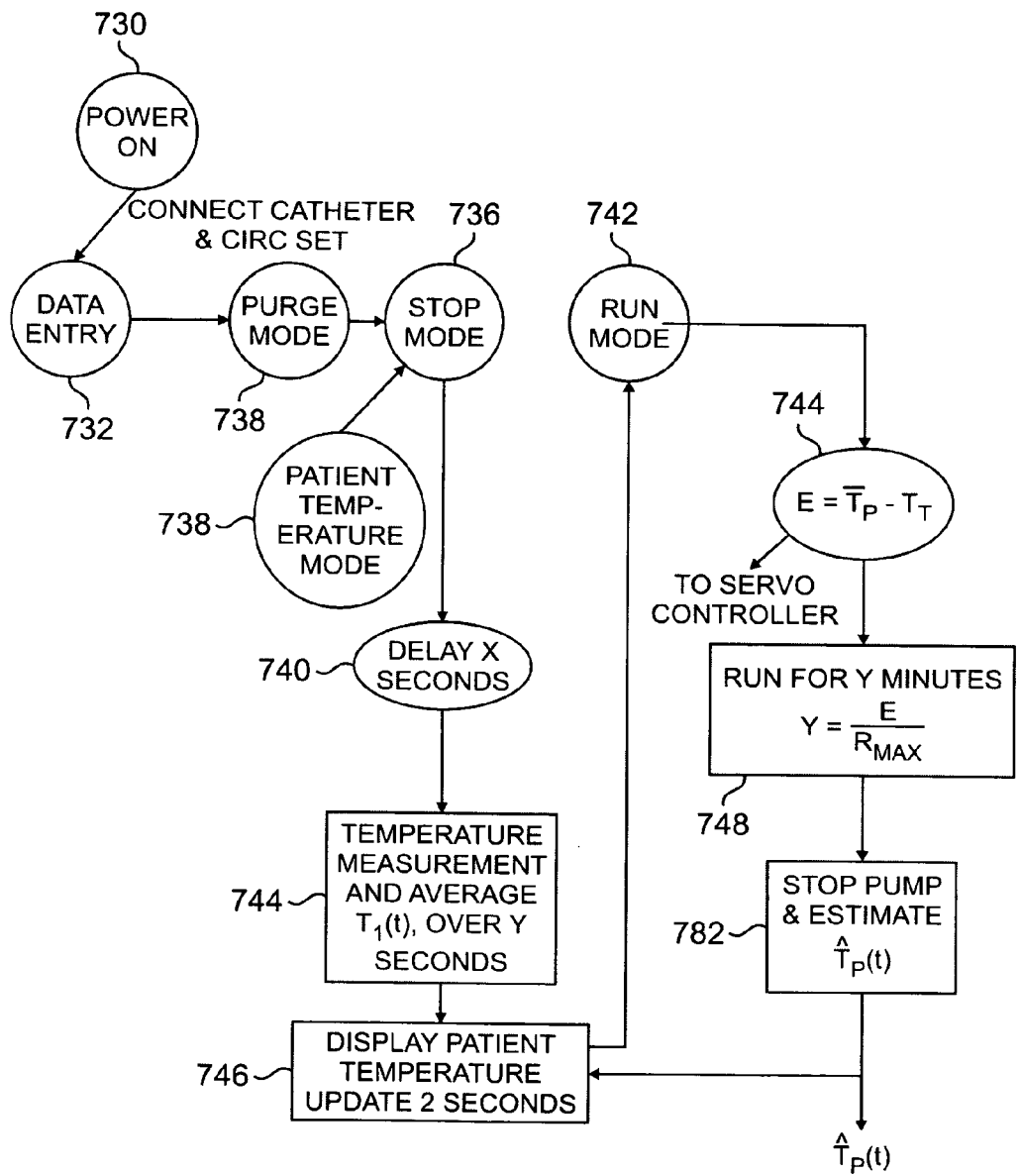
FIG. 41 shows another system for implementing a method of predicting control temperatures.

In more detail, and referring to FIG. 41, a state diagram is shown for an embodiment of the present invention. Steps according to the state diagram include: turning the system power on (step 730) and performing desired data entry. This data entry (step 732) may include entering such information as catheter size, target temperature, rate or period of cooling or warming, and so on. Then the catheter and its accompanying circulation set may be connected to each other and to the console. The system may then be purged (step 734). Following this, the system is in the 'stop' mode (step 736), and the catheter may be inspected, inserted, etc. If desired, the system may enter a patient temperature mode in which the catheter-mounted thermistor may be employed to determine a control temperature (step 738). In this case, a delay of some 'X' seconds is caused to occur (step 740), followed by temperature measurement and averaging) (step 744) over Y seconds. Depending on catheter size, X can range from zero seconds to, e.g., 24 seconds or more. Following X, during Y, various temperatures can be measured, or otherwise determined, including $T_{the}(t)$, $T(t)_{CONTROL}$, and $T(t)_{MONITOR}$. These may be acquired at, e.g., 10 Hz or such other frequency as may be desired. The average trend, with respect to time, of the temperature of the patient may be approximated by the average trend of the temperature of the HTE, i.e., $$T_p(t) \cong T_{HTE}(t)$$

The patient temperature may then be displayed, e.g., for 2 seconds (step 746). The run mode may then be entered (step 742), and the patient cooled or warmed. The servo error may then be determined (step 744). Once the size of the servo error is determined, the interval, over which it is safe to run in maximum cooling or heating mode, may then be determined (step 748). After this interval, the system pump is stopped and a projection mode of the control temperature (step 782) is entered. The time the system is stopped may be, e.g., 10 seconds to 45 seconds, such as 15 seconds or 30 seconds. The projected temperature may then be the basis for future calculations and, if desired, may be displayed.

As an example, during the induction phase of hypothermia, the pump is stopped approximately 3 to 5 times for about 15 to 30 seconds each, for each new patient temperature estimate. So the total cool down times are lengthened a few minutes over an average cool down time.

Figure 42:
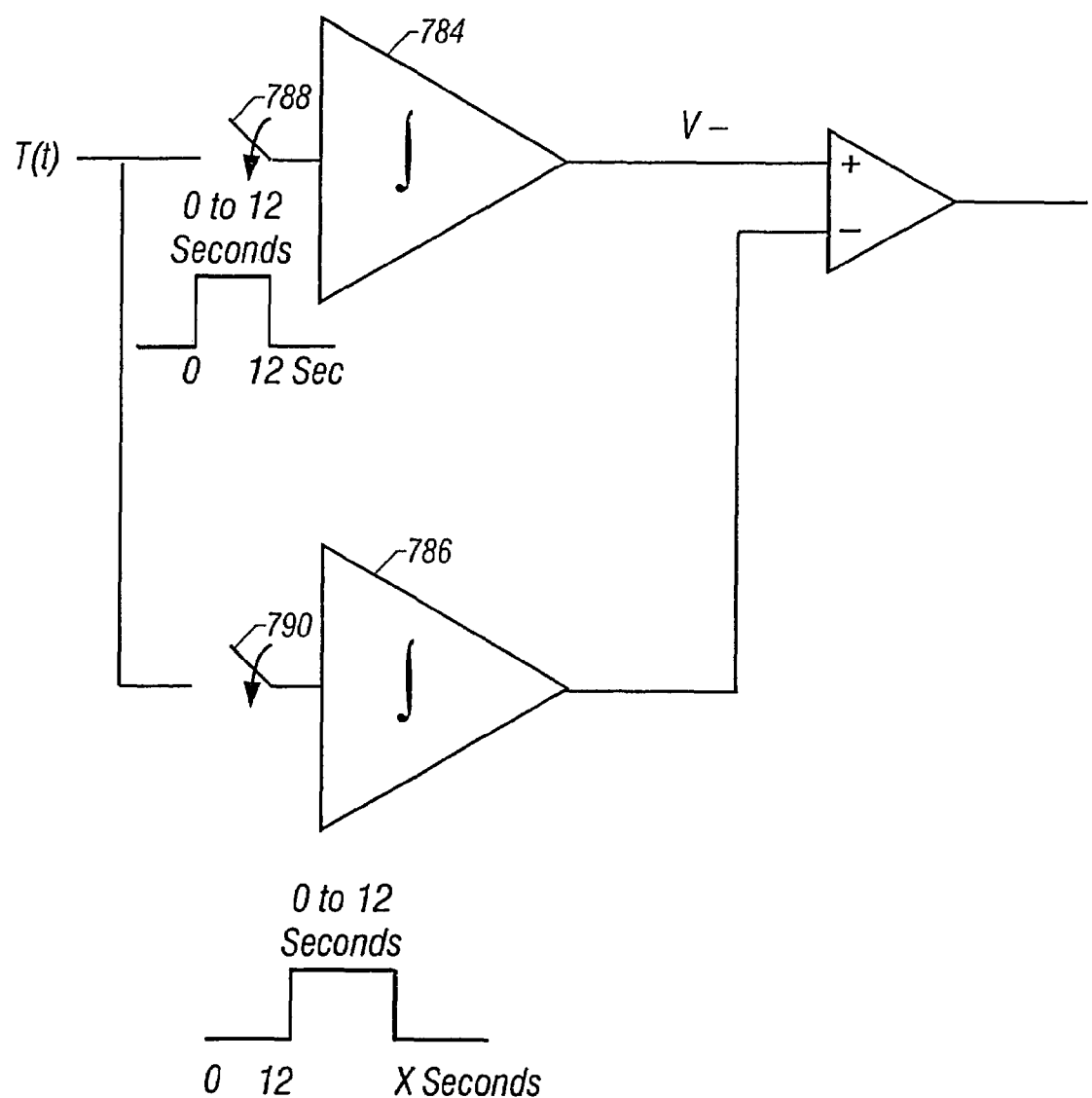
FIG. 42 shows a comparator switch which may be used in the embodiment of, e.g., FIG. 41.

FIG. 42 shows a comparator switch which may be employed in an embodiment of the invention. In FIG. 86, the closing of switch 788 initiates the integration of area A1 by integrator 784, and the closing of switch 790 initiates the integration of area A2 by integrator 786.

A different theoretical model is now employed to explain methods of the embodiment of the present invention. To model the transient behavior of the catheter immediately following the cessation of internal fluid flux, consider the simplified (axisymmetric) system of a circular cylinder with temperature $T_0$ immersed in a steady axial fluid flow with constant temperature $T_c$ far from the cylinder. If the temperature on the interior of the cylinder varies with time but is uniform at each longitudinal section, then, assuming that the longitudinal variation of temperature within the cylinder is small compared to the difference in temperature between the cylinder and its environment, the time rate of change of temperature at each section of the cylinder is given by $$\frac{\partial T}{\partial t} = \alpha(T_c - T) \qquad \text{eq. 1}$$

where $\alpha$ is a constant which depends on the material properties of both the cylinder and the exterior fluid in addition to the kinematics of the external flow field. This simplified analysis suggests that the transient signal from a catheter-mounted temperature sensor will correlate with a function of the form $$T(t) = T_\infty - C \exp(-\alpha t) \qquad \text{eq. 2}$$

where $T_\infty$ is the equilibrium temperature, C is the offset of $T_\infty$ from the starting temperature (which is necessarily unknown in the case of data with non-negligible noise), and $\alpha$ depends on the material properties of the catheter and heat transfer fluid in addition to the material properties and kinematics of the exterior environment. If the range of $\alpha$ can be empirically bounded, then a simple procedure consisting of a sequence of 2-dimensional least squares fits to a function with the form of eq.2 is sufficient to determine T. whenever an updated control signal is required.

To determine $T_\infty$ fluid flux in the catheter is first halted. After a short period to allow dissipation of transient fluid motion, such as 15 seconds, a sequence of n temperature values $T_i$ from an embedded thermistor are acquired at the rate $1/\Delta t$, where $\Delta t$ is the (constant) time interval between adjacent samples. For example, 30 samples may be taken at 2 second intervals. In order to avoid the non-linear system resulting from direct application of the method of least squares to the data $T_i$ and a function with the form of eq.2, $\alpha$ is instead specified and the resulting 2-D linear system is solved. Assuming that in-vitro evaluation of catheter performance allows the statement that:

$$\alpha_{min} < \alpha < \alpha_{max} \qquad \text{eq. 3}$$

for a specific catheter size, then the error between the temperature data and a function with the form of eq.2 is defined for a particular $\alpha$ as $$\varepsilon(\alpha_j) = \sum_{i=1}^{n} (T_i - (T_{\infty,j} - C_j \exp(-\alpha_j t_i)))^2 \qquad \text{eq. 4}$$

where $\alpha_{min} < \alpha_j < \alpha_{max}$. In practice, $\epsilon(\alpha)$ is minimized with respect to $T_\infty$ and C for a sequence of $\alpha_j$ over the domain specified in eq.3 with $$\alpha_j = (j-1)\frac{(\alpha_{max} - \alpha_{min})}{m-1} + \alpha_{min}; 1 \le j \le m \qquad \text{eq. 5}$$

If the resulting discrete representation of the function $\hat{\epsilon}(\alpha)$ (where $\hat{\epsilon}$ represents the minimum value of $\epsilon$ for a particular $\alpha$) has a unique minimum in the domain specified in eq.3, then the triplet $(T_\infty, C, \alpha)$ which produces the best fit of the data $T_i$ with the assumed functional form is defined by the value of $\alpha$ associated with the minimum in $\hat{\epsilon}(\alpha)$. The number of samples m is chosen to provide sufficient resolution of the resulting function $\hat{\epsilon}(\alpha)$.

For each $\alpha_j$, the corresponding $T_{\infty,j}$ and $C_j$ which result in the minimum error $\hat{\epsilon}(\alpha_j)$ are found by requiring that the two partial derivatives $$\frac{\partial \varepsilon}{\partial T_\infty} = -\sum_{i=1}^{n} 2(T_i - (T_\infty - C\exp(-\alpha t_i))) \qquad \text{eq. 6}$$

$$\frac{\partial \varepsilon}{\partial C} = \sum_{i=1}^{n} 2(T_i - (T_\infty - C\exp(-\alpha t_i)))\exp(-\alpha t_i)$$

must vanish. Expressing eq.6 in matrix form, $$\begin{bmatrix} a_{11} & a_{12} \\ a_{21} & a_{22} \end{bmatrix} \begin{bmatrix} T_\infty \\ C \end{bmatrix} = \begin{bmatrix} RHS_1 \\ RHS_2 \end{bmatrix} \qquad \text{eq. 7}$$

where $$a_{11} = \sum_{i=1}^{n} (1) \qquad a_{12} = -\sum_{i=1}^{n} \exp(-\alpha t_i) \qquad \text{eq. 8}$$

$$a_{12} = \sum_{i=1}^{n} \exp(-\alpha t_i) \qquad a_{22} = -\sum_{i=1}^{n} \exp(-2\alpha t_i)$$

and $$RHS_1 = \sum_{i=1}^{n} T_i \qquad \text{eq. 9}$$

$$RHS_2 = \sum_{i=1}^{n} T_i \exp(-\alpha t_i)$$

Solving for $T_\infty$ and C, we find $$T_\infty = \frac{RHS_1 a_{22} - RHS_2 a_{12}}{a_{11}a_{22} - a_{21}a_{12}} \qquad \text{eq. 10}$$

$$C = \frac{RHS_2 a_{11} - RHS_1 a_{21}}{a_{11}a_{22} - a_{21}a_{12}}$$

Once $T_\infty$ and C are known, $\hat{\epsilon}(\alpha_j)$ is computed with eq.4. Finally, $\alpha$ (and the corresponding $T_\infty$ and C) which produces the smallest least-squares error between the temperature data and a function with the form of eq.2 is defined by the minimum of the discrete representation of the function $\hat{\epsilon}(\alpha)$.

If the function $\hat{\epsilon}(\alpha)$ has no unique minimum, or if the minimum in $\hat{\epsilon}(\alpha)$ is greater than a specified limit, the results of the procedure outlined above are ignored and the equilibrium temperature $T_\infty$ may be found by allowing the temperature of the embedded temperature sensor to equilibrate with its external environment.

Failure of the system identification algorithm may indicate improper placement of the catheter (e.g., if the optimal $\alpha$ is smaller than $\alpha_{min}$, the catheter may not have adequate external blood flux, indicating placement in a branching vein instead of the IVC).

Alternately, if $\alpha$ cannot reasonably be assumed constant over the duration of each therapy, then each instance of control signal acquisition, including the first instance following submission of the "run" command, must be treated as a system identification in which $\alpha$ is determined in addition to T. and C. Then a is assumed to be bounded as in the above. Then, with a specified interval $\Delta\alpha$, $T_\infty$ and C are computed to minimize, in the least squares sense, $$\varepsilon_j(\alpha_j) = \sum_{i=1}^{n} (T_i - (T_{\infty j} - C_j \exp(-\alpha_j t_i)))^2 \qquad \text{eq. 11}$$

for each $\alpha_j$ in the domain. $\epsilon(\alpha)$ then defines a function which, if the limits were chosen correctly, obtains a minimum within the domain. This minimum in turn defines the time constant $\alpha$ and subsequently $T_\infty$ and C corresponding to the best fit, in the least squares sense, function of the form represented with the samples of temperature relaxation data. The minimum of $\epsilon(\alpha)$ may be obtained by a simple sorting algorithm if the function 6 is computed with a relatively small $\epsilon\alpha$. Alternatively, for a more sparse sampling of the function $\epsilon(\alpha)$, a quadratic form may be assumed and the minimum found analytically. This alternative approach may execute faster due to the relative cost of the quadratic curve fit as opposed to additional evaluations of equation 11.

Addition of 1$^{st}$ Order Linear Term:

The basic exponential model outlined above is based on the assumption that the temperature of the external environment (i.e. blood in the IVC) is constant over the interval during which the embedded thermistor is allowed to equilibrate with that environment. In general, the temperature of the external environment may be not constant over this interval.

While the catheter is in operation (e.g. in the cooling mode), the various compartments of the body, distinguished on the basis of blood flux per unit mass, or specific blood flux, are in a dynamic state in which the heat removed by the catheter comes preferentially from those tissues for which the specific blood flux is greatest. When coolant flux in the catheter is halted, these physiologic compartments will tend to equilibrate. Tissues with the highest specific blood flux will warm relative to those with lower specific flux as internal body heat is redistributed. As the redistribution of heat occurs primarily through convective transport by blood, the temperature of the environment of the catheter must change as the physiologic compartments approach equilibrium.

While the blood temperature in the vicinity of the catheter generally varies over the interval during which the catheter equilibrates with its environment, the functional form of that variation is not known. For simplicity, any time scale inherent in physiologic temperature variation may be assumed to be greater than the time scale associated with relaxation of temperature within the catheter and thus the physiologic temperature variation may be described with a Taylor series, $$T_{ext}(t) = T_{ext}(t=0) + \frac{\partial T_{ext}}{\partial t}\bigg|_{t=0} \cdot \Delta t + O(\Delta t^2) \qquad \text{eq. 12}$$

where $T_{ext}$ is the temperature of the environment and t=0 defines the instant when heat flux through the catheter is halted. With the above assumption, $\Delta t$, which is the time during which temperature data is acquired from the embedded thermistor, is 'small' relative to the time over which significant physiologic temperature changes will occur. In this situation, the variation of external temperature is accurately modeled by a simple linear function. With this understanding, it is not unreasonable to append the functional form of eq.2 with a linear component to model the changing temperature of the external environment $$T(t) = T_\infty - C\exp(-\alpha t) + \beta t \qquad \text{eq. 13}$$

where $\beta$ is the unknown rate of change of external temperature which occurs in the body after cessation of heat transfer through the catheter.

The process for computation of the best fit function with the form of eq.13 to the temperature data acquired from the embedded thermistor is analogous to that described for the simpler 3-dimensional model. A series of values are assumed for $\alpha$, and the resulting linear least squares problem for the error between the empirical data and the assumed functional form are solved for the triplet ($T_\infty$, C, $\beta$). The solution is defined as the value of $\alpha$ and the associated ($T_\infty$, C, $\beta$) for which the least squares error is minimum.

Alternatively, one may assume another form for $T_{ext}(t)$:

$$T_{ext}(t) = T_{ext}^\infty - (T_{ext}^\infty - T_{ext}^0)\exp(-\beta t) \qquad \text{eq. 14}$$

in which $T_{ext}$, $T_{ext}^\infty$, and $T_{ext}^0$, are, respectively, blood temperature in the environment of the catheter, the relaxed temperature of the blood in the environment of the catheter and the corresponding temperature at cessation of catheter flux. The constant $\beta$ is the characteristic relaxation rate of blood temperature. Substituting blood temperature given in equation 14 for $T_c$ in equation 1, $$\frac{dT}{dt} = \alpha\{T_{ext}^\infty - (T_{ext}^\infty - T_{ext}^0)\exp(-\beta t) - T\} \qquad \text{eq. 15}$$

The temperature measured by the sensor embedded in the catheter is then given by $$T(t) = T_{ext}^{\infty} - \frac{\alpha}{\alpha - \beta}(T_{ext}^{\infty} - T_{ext}^{0})\exp(-\beta t) + \left\{T_0 - T_{ext}^{\infty} + \frac{\alpha}{\alpha - \beta}(T_{ext}^{\infty} - T_{ext}^{0})\right\}\exp(-\alpha t) \quad \text{eq. 16}$$

for $\alpha \approx \beta$. $T_0$ is the starting temperature in the catheter. The requirement that $\alpha \approx \beta$ is not overly restrictive in practice since the characteristic relaxation rate of the catheter is generally much larger than the corresponding physiologic rate.

Correlation of equation 16 with a sequence of discrete temperature data samples requires the solution of a 5-dimensional non-linear least squares problem. The solution set ($T_0$, $T_{ext}^{\infty}, T_{ext}^{0}, \alpha, \beta$) is obtained by assuming $$\alpha_{min} < \alpha < \alpha_{max}$$

$$\beta_{min} < \beta < \beta_{max} \quad \text{eq. 17}$$

and solving for the remaining constants ($T_0, T_{ext}^{\infty}, T_{ext}^{0}$) via a sequence of (n×m) 3-dimensional linear least squares procedures similar to that described above, where n and m are, respectively, the number of discrete $\alpha$ and $\beta$ values in the domains described by equation 17. The best fit function with the form of equation 15 is chosen by searching the resulting set of (n×m) 3-dimensional linear least squares solutions for the combination of $\alpha$ and $\beta$ which result in the smallest fit error.

In practice, insufficient computational resources are often available for real-time correlation of the functional form given in equation 14 with patient temperature data. Instead, predictions are made using the simpler 3-dimensional technique described above, and the more involved 5-dimensional solution is employed for analysis of recorded data. Comparison of solutions obtained through the 3 and 5-dimensional curve fitting procedures suggests that $\alpha$ is roughly 25% greater than that computed with the 3-dimensional procedure. This is not unexpected since variation of external temperature during catheter relaxation may be included in the computation of $\alpha$ with the simpler 3-dimensional procedure.

4 Application to AMI Patient Temperature Data:

Although the preferred result of the correlations described in sections 2 and 3 is the computation of core body temperature, application of the algorithm also produces the characteristic relaxation rate $\alpha$ exhibited by the catheter temperature data during equilibration with the environment. This rate is useful for determining the degree to which catheter temperature has relaxed during a finite acquisition cycle. Expressing equation 2 in the form $$\ln\left(\frac{\Delta T(t)}{\Delta T_0}\right) = -\alpha t \quad \text{eq. 18}$$

where $$\Delta T(t) = T(t) - T_{\infty} \quad \text{eq. 19}$$

$$\Delta T_0 = T_0 - T_{\infty}$$

the ratio of temperature differences can be seen to be correlated with the degree of relaxation exhibited by the catheter temperature data in a certain time interval. In practice, temperature at the site of the embedded sensor during operation is roughly 10 C., so that relaxation to body temperatures of the order of 35 C. results in an initial offset from equilibrium of ~25 C. Requiring the catheter temperature to relax to within 0.5 C. of the equilibrium value in order for catheter temperature to accurately reflect body temperature, it is seen that $$\alpha t = 3.91 \quad \text{eq. 20}$$

The minimum value $\alpha$ must attain in order to satisfy the requirement that catheter temperature is relaxed to within 0.5 C. in a specified amount of time may now be determined. When t=90 sec., $\alpha_{min}$=0.043. In another example, for a less than 1% variation, then $\alpha t$=4.6 time constants. And for $\alpha$=0.06, then about half the data falls into the range, i.e., passes successfully through the projection "window". In any case, a larger number of samples assists the issue of averaging.

Higher Order Variations of Physiologic Temperature

It should be clear to practitioners skilled in the art, given the teaching above, that the method described above for the assumed functional forms may be extended to a variety of additional forms with both linear and non-linear improvements to the basic exponential model.

Flux Drift As Spatial Integrator

As before, the working fluid flux would be halted during the time that a control temperature is obtained. With the heat transfer fluid flux halted, the heat path to the temperature sensor in either configuration is only conductive, through the plastic catheter shaft and the static heat transfer fluid. The heat flux which causes the temperature sensor to relax to the temperature of its environment therefore necessarily originates preferentially in the immediate vicinity of the temperature sensor. If, in some configurations, heat flux into the catheter is reduced in this vicinity, the necessary relaxation time increases and prediction or measurement of the temperature will require longer sampling intervals. Such a configuration may obtain when an introducer covers the temperature sensor, and in this case an additional thermal resistance would be imposed between the temperature sensor and the environment.

To obviate this difficulty, instead of halting the heat transfer fluid (working fluid) flux during temperature acquisition, the flux may be reduced to a creeping flow so that heat conducted through the entire metallic shell of the heat transfer tip is convected past the temperature sensor. If the flux is sufficiently slow, fluid entering the heat transfer tip will equilibrate with blood temperature before passing the temperature sensor. In this way, the entire metallic shell of the heat transfer tip is employed as a spatial integrator to minimize the dependence of the temperature sensor relaxation rate or temperature on the properties of the immediate environment of the temperature sensor.

Other Considerations for Catheter-Mounted Temperature Sensors

Analysis of human clinical data has revealed the presence of (at least) two distinct time scales associated with the relaxation of catheter temperature in the above system. One of these intrinsic time scales is related to the geometry of the catheter and the properties of its environment (e.g., vessel diameter and blood flux) while the other time scale appears to reflect a physiologically imposed time related to equilibration of (body) thermal compartments after cessation of endovascular heat transfer. Both time scales appear to be related to simple exponential decay of the associated physical process (i.e., heat flux into the catheter, and heat transfer between body compartments), and the temperature history recorded by the embedded temperature sensor may be a convolution of the two processes. Ideally, the resulting temperature history appears as a rapid decay to within approximately 1° C. of the final value, governed by the catheter-intrinsic time scale, followed by a more gradual relaxation governed by the physiologic time scale. If the two time scales are distinct, a local asymptotic temperature related to the catheter-intrinsic time scale can be extrapolated through a simple non-linear least squares fit to a finite sample of catheter temperature data. This results in an approximation of the temperature which would have been obtained in the catheter environment in the absence of the 2nd process, i.e. equilibration of body compartments, which tends to occurs on a much longer time scale. If the two time scales are similar, as might result if the thermal mass of the catheter were much larger, or if the sensor were located in a region of restricted blood flux, then de-convolution of the two time scales becomes difficult and extrapolation of a useful asymptotic temperature somewhat more problematic.

Far distal placement of the temperature sensor, relative to and apart from the heat exchanger, may be associated with certain disadvantages. Cold fluid inside the heat transfer element will influence the temperature recorded by a distally located sensor by extracting heat from the external blood before it passes over the sensor. If the thermal mass of the heat transfer element is large as, for example, in the case of a large diameter balloon, then the catheter intrinsic time scale will increase and prediction of the asymptotic temperature becomes difficult. In addition, turbulence or mixing in the blood may result in fluctuations in the recorded temperature if the sensor is close to the heat transfer element. However, moving the sensor even further downstream may result in undesirable proximity of the sensor to tissue, such as cardiac tissue.

Placement of the temperature sensor within the catheter shaft (housing the heat transfer fluid supply and return lumens) may be desirable. However, this necessitates careful consideration of the dynamics of fluid motion in the supply and return lumens. If the supply/return lumens are symmetric, or the same size and/or shape, then introduction of the temperature sensor assembly into one of the lumens will increase the associated pressure drop along that path. If the sensor is placed in the return lumen, pressure in the balloon will increase, resulting in a mechanically stiffer balloon. If the sensor is placed in the supply lumen, the flux of heat transfer fluid will decrease unless pump pressure is increased. If instead the supply and return lumens are asymmetric, placement of the sensor assembly in the larger return lumen may result in a negligible effect on catheter pressure and flux.

Use of a YSI-400 thermistor as the temperature sensing device may be desirable. This may render the device compatible with most of the digital thermometers in the clinical environment. If fluid path restrictions, as described above, necessitate the use of a smaller thermocouple device, the associated electronics (i.e. accurate and expensive millivolt amplifiers with temperature compensated junctions) become more complicated and incompatible with the popular clinical equipment. Additionally, thermocouple accuracy is generally less than that available with a thermistor.

Temperature Estimation Errors & Accuracy:

The ability of the system to control to a desired set point or target temperature may be limited by the cooling power, degree of thermal disturbance (discussed below), accuracy of measuring the temperature within the catheter, patient temperature drift during the sampling period when the pump is turned off, and the accuracy of the estimation algorithm.

Clinical experience in neurosurgical settings has shown that the cooling power required to maintain hypothermia at 33° C. is less than about 20% of the maximum power capability of the system even when a convective warming blanket is used during the hypothermia maintenance period. With a servo gain of 0.2 C. for 100% power, a 20% load would yield a servo Type 1 offset of 20%×0.2 C.=0.04 C. error. For a 9 fr catheter which has about 65% of the 14 fr capability, this would yield a offset error during hypothermia maintenance of approximately 30%×0.2 C.=0.06 C. In the setting of stroke and acute myocardial infarction, the steady state load during maintenance is approximately the same; i.e., about 0.06 C offset due to the need to continue to extract heat out of the patient to balance the patient's retained metabolic heat due to surface warming.

The accuracy of the thermistor may have, e.g., a specification of +/−0.1 C. for 100% confidence (4 standard deviations) in the temperature range of 32 to 42 C. The electronics and signal processing may have, e.g., a specification of +/−0.1 C. (95% confidence =+/−2 S.D.) to cover the initial calibration, dynamic temperature range, drift, and aging considerations. The calibration of the hardware temperature channels may be checked and recalibrated if needed on, e.g., an annual basis. The accuracy of the thermistor and the hardware signal conditioning and processing is comparable to other commercially available temperature monitoring disposable sensors and equipment used routinely in the hospital operating room and intensive care settings for monitoring patient temperature.

During the sample period of acquiring temperature sensor data, approximately 30 seconds for the 9 fr and 60 seconds for 14 fr device, the patient can rewarm due to retained metabolic heat and cessation of heat extraction. In one clinical study, the maximum rate of rewarming observed was. less than about 1.5 C./hour or approximately 0.025 C. in 60 seconds.

A last error source is the ability of the temperature estimation algorithm to predict the final value of the sensor's temperature response to a step input. An error sensitivity analysis was conducted by varying the sampling time duration (acquisition period) and comparing the estimated temperature to the actual temperature. For 20 seconds of sample points (total of 24 seconds of the pump being in the "off" mode), the standard deviation of the error was 0.1 C. Decreasing the sample points to 15 (total 19 seconds of pump off) increases the standard deviation of error to 0.18 C. while increasing the sample points to 25 (total of 29 seconds) decreases the standard deviation to 0.7 C. A 20 sample point algorithm has been chosen for an optimal trade off of time versus estimation accuracy.

Thus the temperature measurement and estimation accuracy has various components, which can be considered statistically independent error sources (See Table VIII). Summing these error sources would yield the maximum expected error, 95% confidence, of, e.g., about 0.51 C. Taking the root mean square error, i.e., RMS error, would be about 0.26 C.

Potential Thermal Disturbances:

One design goal of a closed loop servo controller is to have sufficient capability to maintain control during various load conditions. This capability in embodiments of the present invention is expressed as the maximum thermal power available to null out a disturbance, at what amount of energy is it delivered for a particular servo error magnitude, defined as the servo gain, and the responsiveness of the controller that may have intentional lags or leads in the feedback controller for control stability. Since the patient's response to a thermal input is typically slow, over hours, no additional magnitude or phase compensation may be required in the controller to optimize stability. The key ingredient to loop stability is the servo gain level, which has been chosen to be in the range of 500 to 800 watts per degree C. of error depending on which catheter size is chosen. With this servo gain level, clinical studies have demonstrated few or no instability problems with minimal steady state servo error and good response.

A potential thermal disturbance would be an IV infusion of room temperature (cold) fluids. For a constant infusion rate of 1.4 ml/min (2 liters per 24 hours) of 20° C. fluid, this would represent a thermal input rate of about 2 watts. The system would have to develop a servo error of approximately (2 watts)/(600 watts/C.) or 0.003 C. to correct for this steady state thermal disturbance. Since 2 watts is well within the capability of embodiments of the present invention, this disturbance would be well controlled.

A more challenging thermal disturbance would be a rapid bolus infusion of fluids, such as 250 ml, in, e.g., 5 minutes. If the fluid were not heated to body temperature, this would represent an infusion rate of about 1 cc/sec at 20 C. for an equivalent energy input of about 70 watts for 5 minutes. It takes about 70 to 85 watts for one hour to lower the body temperature of an average patient, 70 kg weight, one degree C. Thus, a 5 minute bolus would have the effect of lowering the temperature 5/60th of one degree, 0.083 C., again well within the capabilities of the present system to control.

In actual clinical deployment of embodiments of the present invention, a convective or electrical heating blanket may be used for patient comfort and for depressing shivering. The blanket temperature setting and how much of the patient's body is exposed to the blanket will determine the net transfer of energy from the patient to the room. Sessler et. al. estimate that a typical blanket can prevent 20 to 50 watts of heat loss to the environment. A 50 watt heat preservation would require the embodied system to extract an additional 50 watts of cooling to maintain the thermal balance. The servo error would move to 50 Watts/600 watts/C.=0.083 C., again well within the capability of the system.

In summary, most if not all of the thermal disturbances as described above are within the capability of embodiments of the closed loop control system to maintain the target temperature within 0.5 C.

As previously mentioned, control algorithms are sometimes used to control the rate at which heat is extracted from the body by the catheter. These algorithms may be embodied in hardware, software, or a combination of both. The gain factor employed by such algorithms is dependent on the effective thermal mass of the body or organ being cooled. Thus, it is important to determine the effective thermal mass so that an appropriate gain factor can be calculated for the feedback control algorithm.

The mass of the body (organ or whole body) being cooled can be estimated by relating the power removed by the catheter to the power lost by the body.

The power removed by the catheter may be expressed as follows:

$$P_{catheter}=Mc_f \Delta T \quad (1)$$

Where M is the mass flow rate of the fluid circulating through the catheter (typically measured in terms of cc/s), $c_f$ is the heat capacity of the fluid, and $\Delta T$ is the temperature difference between the working fluid as it enters the catheter and as it exits the catheter. Accordingly, $P_{catheter}$ can be readily calculated by measuring the mass flow of the circulating fluid and the temperature difference between the working fluid as it enters and exits the catheter.

The power removed by the catheter as determined by equation (1) may be equated to the power that is lost by the patient's body:

$$P_{catheter}=mc_b \partial T/\partial t \quad (2)$$

Where $P_{catheter}$ is now the power lost by the patient's body and has the value calculated by equation (1), m is the effective thermal mass of the body being cooled, $c_b$ is the heat capacity of the body, and $\partial T/\partial t$ is the change in temperature per unit time of the mass being cooled.

Accordingly, the effective thermal mass of the body being cooled is:

$$m=P_{catheter}/(c_b \partial T/\partial t) \quad (3)$$

Since all the variables in equation (3) are either known or are measurable, the effective mass can be determined.

The mass calculated in this manner is an effective thermal mass that represents the portion of the body from which power is removed (i.e., the portion of the body that is cooled). The temperature change in equation (3) represents the temperature change of the portion of the body being cooled. For example, if whole body cooling is to be performed, the change of the core body temperature may be measured to calculate mass in accordance with equation (3). In the effective mass may represent about 50% of the total body mass. If the patient is vasodilated, the effective mass will be closer to the total body mass.

Alternatively, if only a selected organ such as the brain is to be cooled, then the temperature change that will be used in equation (3) would be the temperature change of the organ, assuming of course that the organ can be at least briefly considered to be largely thermally isolated from the remainder of the body. In this case the effective mass that is determined would be comparable to the mass of the organ. If the selected organ to be cooled is the brain, for example, the catheter is placed in the common carotid artery, the internal carotid artery, or both. The temperature changed used in equation (3) will be measured by inserting a temperature sensor into the brain or via a tympanic membrane sensor, both of which are commercially available.

EXAMPLE

In an animal study, whole body cooling was accomplished by inserting the catheter through the femoral vein and then through the inferior vena cava as far as the right atrium and the superior vena cava. Cooling was initiated by circulating a working fluid at a flow rate of 5 cc/sec. The temperature differential between the fluid entering the catheter and the fluid exiting the catheter was 17° C. Accordingly, the power extracted by the catheter was 354 watts.

The body core temperature was measured through the esophagus. Twenty minutes after cooling was initiated, the rate at which the core temperature changed was measured over a period of about ten minutes, resulting in an average temperature change of about 4° C./hr.

From equation (3) above, the effective thermal mass is:

$$m=354 \text{ watts}/(0.965 \text{ watts/kg C.°})(10° \text{ C./hr})=37 \text{ kg}$$

The total mass of the animal was 53 kg, and thus the effective mass was found to be 69% of the total mass. One practice of the present invention is illustrated in the following non-limiting example.

Exemplary Procedure

1. The patient is initially assessed, resuscitated, and stabilized.
2. The procedure may be carried out in an angiography suite or surgical suite equipped with fluoroscopy.
3. An ultrasound or angiogram of the external jugular/superior vena cava or femoral vein/inferior vena cava can be used to determine the vessel diameter and the blood flow; a catheter with an appropriately sized heat transfer element can be selected.
4. After assessment of the veins, the patient is sterilely prepped and infiltrated with lidocaine at a region where the femoral artery may be accessed.
5. The, e.g., femoral vein is cannulated and a guide wire may be inserted to the inferior vena cava. Placement of the guide wire is confirmed with fluoroscopy.
6. An angiographic catheter can be fed over the wire and contrast media injected into the vein to further to assess the anatomy if desired.
7. Alternatively, the femoral vein is cannulated and a 10-12.5 french (f) introducer sheath is placed.
8. A guide catheter may be placed into the inferior vena cava. If a guide catheter is placed, it can be used to deliver contrast media directly to further assess anatomy.
9. The cooling catheter is placed into the inferior vena cava via the guiding catheter or over the guidewire.
10. Placement is confirmed if desired with fluoroscopy.
11. Alternatively, the cooling catheter shaft has sufficient pushability and torqueability to be placed in the inferior vena cava without the aid of a guide wire or guide catheter.
12. The cooling catheter is connected to a pump circuit also filled with saline and free from air bubbles. The pump circuit has a heat exchange section that is immersed into a water bath and tubing that is connected to a peristaltic pump. The water bath is chilled to approximately 0° C.
13. Cooling is initiated by starting the pump mechanism. The saline within the cooling catheter is circulated at 5 cc/sec. The saline travels through the heat exchanger in the chilled water bath and is cooled to approximately 1° C.
14. The saline subsequently enters the cooling catheter where it is delivered to the heat transfer element. The saline is warmed to approximately 5-7° C. as it travels along the inner lumen of the catheter shaft to the end of the heat transfer element.
15. The saline then flows back through the heat transfer element in contact with the inner metallic surface. The saline is further warmed in the heat transfer element to 12-15° C., and in the process, heat is absorbed from the blood, cooling the blood to 3° C. to 35° C. During this time, the patient may be warmed with an external heat source such as a heating blanket. At any point in the procedure, thermoregulatory drugs, such as anti-shivering drugs, may be administered.
16. The chilled blood then goes on to chill the body. It is estimated that less than an hour will be required to cool the brain to 30° C. to 35° C.
17. The warmed saline travels back the outer lumen of the catheter shaft and is returned to the chilled water bath where the same is cooled to 1° C.
18. The pressure drops along the length of the circuit are estimated to be between 1 and 10 atmospheres.
19. The cooling can be adjusted by increasing or decreasing the flow rate of the saline. Monitoring of the temperature drop of the saline along the heat transfer element will allow the flow to be adjusted to maintain the desired cooling effect.
20. The catheter is left in place to provide cooling for, e.g., 6-48 hours.

It is envisioned that the following veins may be appropriate to percutaneously insert the heat transfer element: femoral, internal jugular, subclavian, and other veins of similar size and position. It is also envisioned that the following veins may be appropriate in which to dispose the heat transfer element during use: inferior vena cava, superior vena cava, femoral, internal jugular, and other veins of similar size and position.

Methods of Use Employing Thermoregulatory Drugs

The above description discloses mechanical methods of rewarming a patient, or portions of a patient, to minimize the deleterious consequences of total body hypothermia. Another procedure which may be performed, either contemporaneous with or in place of mechanical warming, is the administration of anti-vasoconstriction and anti-shivering drugs. Such drugs minimize the effect of vasoconstriction which may otherwise hinder heat transfer and thus cooling of the patient. In general, hypothermia tends to trigger aggressive thermoregulatory defenses in the human body. Such drugs also prohibit responses such as shivering which may cause damage to cardiac-compromised patients by increasing their metabolic rate to dangerous levels.

To limit the effectiveness of thermoregulatory defenses during therapeutic hypothermia, drugs that induce thermoregulatory tolerance may be employed. A variety of these drugs have been discovered. For example, clonidine, meperidine, a combination of clonidine and meperidine, propofol, magnesium, dexmedetomidine, and other such drugs may be employed.

It is known that certain drugs inhibit thermoregulation roughly in proportion to their anesthetic properties. Thus, volatile anesthetics (isoflurane, desflurane, etc.), propofol, etc. are more effective at inhibiting thermoregulation than opioids which are in turn more effective than midazolam and the central alpha agonists. It is-believed that the combination drug of clonidine and meperidine synergistically reduces vasoconstriction and shivering thresholds, synergistically reduces the gain and maximum intensity of vasoconstriction and shivering, and produces sufficient inhibition of thermoregulatory activity to permit central catheter-based cooling to 32° C. without excessive hypotension, autonomic nervous system activation, or sedation and respiratory compromise.

These drugs may be particularly important given the rapid onset of thermoregulatory defenses. For example, vasoconstriction may set in at temperatures of only ½ degree below normal body temperature. Shivering sets in only a fraction of a degree below vasoconstriction.

The temperature to which the blood is lowered may be such that thermoregulatory responses are not triggered. For example, thermoregulatory responses may be triggered at a temperature of 1-1½ degrees below normal temperature. Thus, if normal body temperature is 37° C., thermoregulatory responses may set in at 35° C. Thermoregulatory drugs may be used to lower the temperature of the thermoregulatory trigger threshold to 33° C. Use of the heating blankets described above may allow even further cooling of the patient. For example, to lower the patient's temperature from 33° C. to 31° C., a 2° C. temperature difference, a 2 times 5° C. or 10° C. rise is surface temperature may be employed on the skin of the patient to allow the patient to not "feel" the extra 2° C. cooling.

Figure 43:
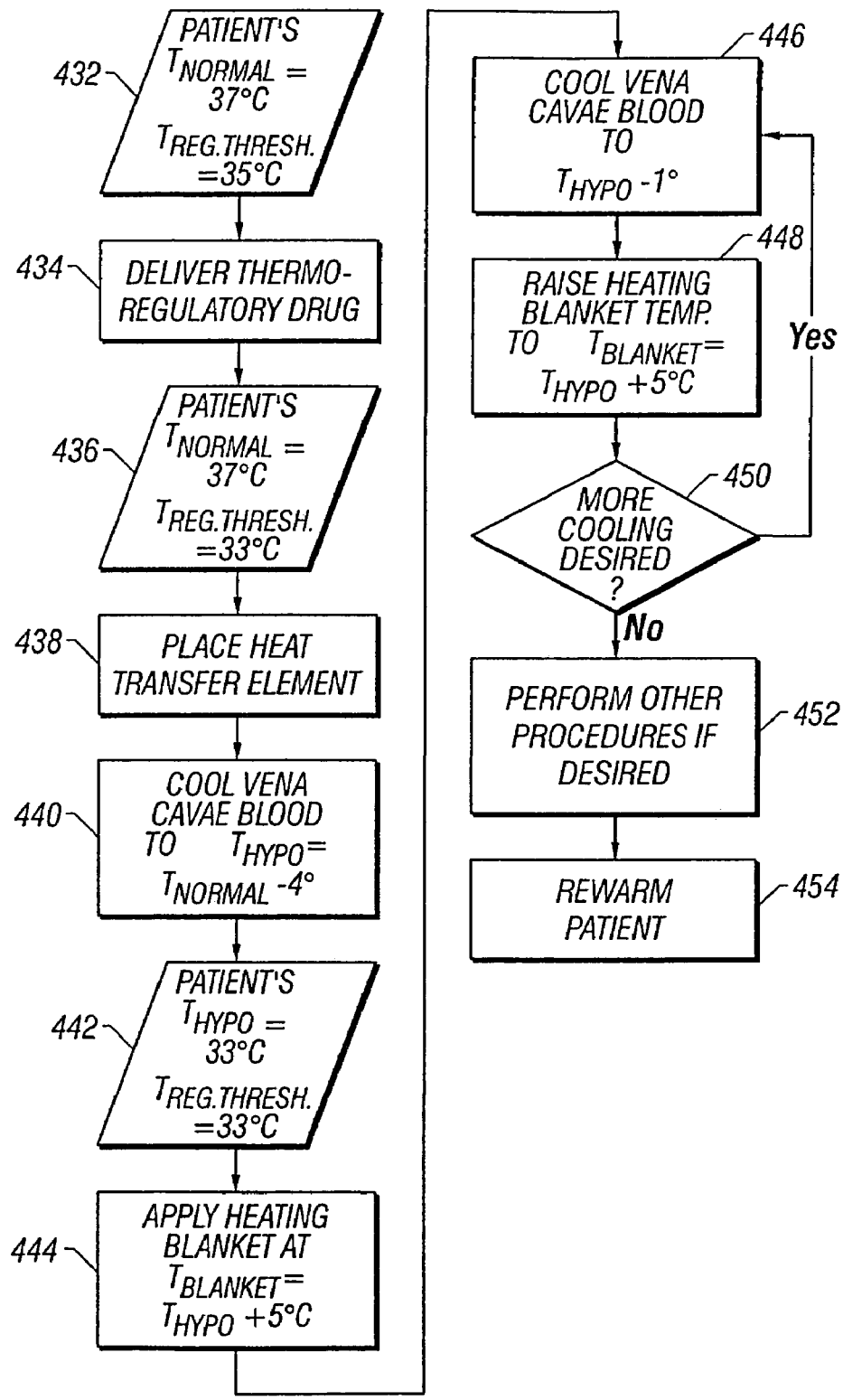
FIG. 43 is a flowchart showing an exemplary method of the invention employing heating blankets and thermoregulatory drugs.

A method which combines the thermoregulatory drug methodology and the heating blanket methodology is described with respect to FIG. 43. This figure is purely exemplary. Patients' normal body temperatures vary, as do their thermoregulatory thresholds.

As shown in FIG. 43, the patient may start with a normal body temperature of 37° C. and a typical thermoregulatory threshold of 35° C. (step 432). In other words, at 35° C., the patient would begin to shiver and vasoconstrict. A thermoregulatory drug may be delivered (step 434) to suppress the thermoregulatory response, changing the threshold temperature to, e.g., 35° C. This new value is shown in step 436. The heat transfer element may then be placed in a high flow vein, such as the superior or inferior vena cavae or both (step 438). Cooling may occur to lower the temperature of the blood (step 440). The cooling may be in a fashion described in more detail above. The cooling results in the patient undergoing hypothermia and achieving a hypothermic temperature of, e.g., 33° C. (step 442). More cooling may be performed at this stage, but as the thermoregulatory threshold has only been suppressed to 33° C. (step 442), shivering and vasoconstriction would deleteriously result. This may complete the procedure. Alternatively, an additional drug therapy may be delivered to further lower the thermoregulatory threshold.

An alternate way to lower the thermoregulatory threshold is to use a heating blanket. As noted above, a common rule-of-thumb is that a patient's comfort will stay constant, even if their body temperature is lowered 1° C., so long as a heating blanket, 5° C. warmer than their skin, is applied to a substantial portion of the surface area of the patient (step 444). For a 2° C.-body temperature reduction, a 10° C. (warmer than the skin temperature) blanket would be applied. Of course, it is also known that blankets warmer than about 42° C. can damage patient's skins, this then being an upper limit to the blanket temperature. The patient's body temperature may then continue to be lowered by use of a heating blanket. For each 1° C. reduction in body temperature (step 446), the heating blanket temperature may be raised 5° C. (step 448). After each reduction in body temperature, the physician may decide whether or not to continue the cooling process (step 450). After cooling, other procedures may be performed if-desired (step 452) and the patient may then be rewarmed (step 454).

It is important to note that the two alternate methods of thermoregulatory response reduction may be performed independently. In other words, either thermoregulatory drugs or heating blankets may be performed without the use of the other. The flowchart given in FIG. 43 may be used by omitting either step 434 or steps 444 and 448.

Vasoconstrictive Therapies

High blood flow organs have a more rapid response to hypothermia than that of the peripheral circulation. This response may be maintained or enhanced by applying, as an alternative method of performing hypothermia, a cooling blanket rather than a heating blanket. The cooling blanket may serve to vasoconstrict the vessels in the peripheral circulation, further directing blood flow towards the heart and brain.

An alternate method of performing the same function is to provide separate vasoconstrictive drugs which affect the posterior hypothalamus in such a way as to vasoconstrict the peripheral circulation while allowing heart and brain circulation to proceed unimpeded. Such drugs are known and include alpha receptor type drugs. These drugs, as well as the cooling blankets described above, may also enhance countercurrent exchange, again forcing cooling towards the heart and brain. Generally, any drug or cooling blanket that provides sufficient cooling to initiate a large scale cutaneous peripheral vasoconstrictive response would be capable of forcing the cooling blood flow towards the brain and heart (i.e., the "central" volumes). In this application, the term "peripheral circulation" or "peripheral vasculature" refers to that portion of the vasculature serving the legs, arms, muscles, and skin.

Antishiver Drugs and Regimens

Other thermoregulatory drugs are now described. Meperidine is an analgesic of the phenyl piperdine class that is known to bind to the opiate receptor. Meperidine is also used to treat shivering due to post-operative anesthesia and hypothermia. Meperidine can also treat rigors associated with the administration of amphotericin B.

Meperidine can also be used to control shivering when hypothermia is induced clinically. During periods of ischemia, such as occurs during a stroke or heart attack, hypothermia can protect the tissue from damage. It is important to be able to cool patients with out inducing a general anesthetic condition requiring intubation. To cool conscious patients requires very high doses of meperidine. Cooling of patients can be accomplished by the above noted methods such as cooling blankets (air or water) or alcohol bathing. Cooling can also be accomplished by body cavity lavage (bladder, stomach, colon, peritoneal). The most efficient way to cool patients, as noted above for therapeutic purposes, is using an intravascular catheter. An intravascular cooling catheter has a heat exchange region that is responsible for exchanging heat with the blood. Absorption of heat from the blood by the heat exchange region results in cooling of the body. Causing mixing, or turbulence, on, or near, the heat exchange region, enhances heat transfer by intravascular methods. The heat exchanger of the intravascular catheter can have features that induce turbulence or mixing.

Shivering is regulated by the hypothalamus of the brain. The hypothalamus regulates body temperature in general by controlling heat production and heat loss. Heat production above the base metabolic level is produced through shivering, while heat loss is prevented by vasoconstriction, which decreases blood flow to the skin/periphery. The normothermic set point of the hypothalamus is approximately 37° C. When the body is cooled a threshold is reached at which vasoconstriction and shivering occur. Vasoconstriction occurs approximately 0.5-1.0° C. below the set point, with shivering occurring 1.0-1.5° C. below the set point. The intensity of shivering increases proportionally with the difference from the threshold up to a maximum intensity. Meperidine lowers the threshold at which shivering occurs, but it does not have much effect on the gain and maximum intensity. The reduction of the shivering threshold is proportional to the serum concentration of meperidine, such that greater serum concentrations cause a greater reduction in the threshold. Meperidine is believed to possess special antishivering effects, in particular because it decreases the shivering threshold twice as much as the vasoconstriction threshold. In addition, it prevents or manages shivering better than equianalgesic doses of other opioids.

Meperidine's antishivering effects (lowering of the shivering, threshold) may not be related to binding of the opiate receptor. Meperidine is known to have numerous non-opioid effects such as anticholinergic action and local anesthetic properties. Further, the antishivering effects produced by meperidine are not antagonized by nalaxone, an opiate receptor antagonist. In addition, other opiates such as morphine, pentazocine, and nalbuphine have lesser or no antishivering activity.

Meperidine usage has a number of undesirable side effects, and many are related to the affinity for the opiate receptor. The most serious is respiratory sedation, which can result in death, and may be related to affinity for the delta opiate receptor. It has been shown that blocking the delta opiate receptor with an antagonist can reduce or eliminate opioid induced respiratory sedation. In addition, meperidine is metabolized in the liver by n-demethylation, which produces the metabolite nor-meperidine. Nor-meperidine is known to have central nervous system toxicity and can cause seizures. Meperidine cannot be used in patients with renal insufficiency or kidney failure due to a rapid build up of the normeperidine metabolite. In addition, meperidine cannot be used in patients taking monoamine oxidase inhibitors, due to complications such as convulsions and hyperpyrexia.

Prodines (alpha and beta) are structurally very similar to meperidine. They too bind to the opiate receptor, though with greater affinity. Unlike meperidine, prodines have chirality. Chiral molecules have at least one asymmetric atomic center that causes the mirror image of the base molecule to be non-superimposable on base molecule. Each species, the base molecule and the mirror image, is referred to as an enantiomer.

Chiral molecules are optically active meaning each enatiomer can rotate a plane of polarized light equal but opposite directions, clockwise and counter clockwise, plus and minus. Thus if one enantiomer rotates a plane of polarized light +10 degrees {(+) enantiomer}, the opposite enantiomer will rotate light −10 degrees {(−) enantiomer)}. For example, the two prodines, known as alpha and beta, differ in the position of the 3-methyl group. A chiral atomic center exists at the carbon to which the 3-methyl group is bound and results in the various enantiomeric species. The chemical reactions that produce chiral molecules often produce racemic mixtures, or mixtures that contain fractions of each enantiomer. A racemic mixture that contains equal proportions of each enatiomer is optically inactive.

Binding to the opiate receptor is known to be stereoselective. This means that one enantiomer has much greater affinity for the receptor than the other enantiomer. For example, the (−) isomer of morphine has much greater affinity for the opiate receptor than the (+) isomer. In the case of alpha and beta prodine, the (+) isomer has much greater affinity for the receptor than the (−) isomer.

It is reasonable to assume that the prodines have anti-shiver effects similar to meperidine due to their structural similarity. This is a reasonable assumption because fentanyl, an opioid analgesic that is also structurally related to meperidine, also has anti-shiver effects. Fentanyl, also has opiate related side effects such as respiratory sedation.

The ideal antishiver medication or regimen would have potent antishiver efficacy with little respiratory sedation or other side effects. One way to accomplish is to use meperidine, fentanyl, or other opioids with antishiver effects, in combination with a delta opiate receptor antagonist. Naltrindole or naltriben are competitive antagonists at the delta receptor and can block the respiratory sedation caused by fentanyl. Thus, inducing hypothermia in a conscious patient using an intravascular cooling catheter would be accomplished using a drug regimen that included an opiate such as fentanyl or meperidine in combination with a delta receptor antagonist, such as naltrindole.

A molecule structurally similar to meperidine, but unable to bind to the opiate receptor or having antagonism at the opiate receptor, would likely possess anti-shiver effects, but not opiate related respiratory sedation, since anti-shivering effects may be mediated through a different receptor. This ideal anti-shiver molecule exists in the form of the (−) isomer of alpha or beta prodine. The ratio of opiate efficacy (+/−) between the enantiomeric forms of alpha and beta prodine is at least ~10 to 30 fold. Because of the structural similarity to meperidine they would likely retain the antishiver efficacy. In an analogous example, dextromethorphan is a morphine-based chemical that is a cough suppressant (antitussive). Dextromethorphan, which is the (+) methoxy enantiomer of (−) levorphanol, has retained the antitussive effects of morphine derivatives (i.e. (−) levorphanol), but lost other opiate effects such as analgesia, respiratory sedation, and addiction. In addition, the opiate receptor affinity of the (+) isomer of alpha and beta prodine could also be interrupted. This can be accomplished by adding a hydroxyl (particularly in the m position) to phenyl ring. This is particularly true of the potent opiate analgesic alpha-allylprodine, in which the 3-methyl is replaced with an allyl group. Further, the opiate activity of (+) betaprodine isomer can be significantly diminished by the substitution of the 3-methyl group with an n-propyl or allyl group. These modifications to the (+) isomers of the prodine molecules that inhibit opiate activity will not likely effect antishiver activity due to the structural similarity to meperidine.

Cis-Picenadol, 1,3 dimethyl-4-propyl-4-hydroxyphenyl piperdine (cis 3-methyl, 4-propyl) is phenyl piperdine compound in which the (−) enantiomer has antagonist properties at the opiate receptor. Due to the structural similarity to meperidine, this (−) enantiomer may have anti-shiver activity with little respiratory sedation. It is known that the racemic mixture of this opioid has a ceiling effect with respect to respiratory sedation when used in animals. This ceiling effect may make racemic picenadol a better anti-shiver drug than meperidine. Finally, tramadol may have an enantiomer that has reduced opiate activity that could lower the shiver threshold.

Alpha prodine has been used as an analgesic in clinical medicine, marketed under the trade name Nisentil. The drug is supplied as a racemic mixture. It is possible to separate the racemic mixture into two pure isomers and use the (−) isomer as an antishiver medication. Such a separation can be accomplished using high-performance liquid chromatography (HPLC) using a chiral stationary phase. One such chiral stationary phase is cellulose-based and is supplied as Chiralcel OD and Chiralcel OJ.

A representative example of the use of the novel antishiver, or threshold lowering, drugs or regimen, is a clinical procedure to induce hypothermia in a patient. The patient would first be diagnosed with an ischemic injury, such as a stroke or heart attack. An intravascular cooling catheter or a cooling blanket would be applied to the patient. The patient would be given an intravenous injection of the novel anti shiver drug, such as (−) alpha prodine. Alternatively the patient could be given meperidine or fentanyl in combination with a delta opiate receptor antagonist. Buspirone could be given in combination with either of the above regimens because it is know to enhance the antishiver effects of meperidine. The patient would be cooled to 32-35° C. or lower. During the maintenance of cooling which could last 12-48 hours or longer, doses of the antishiver drug or regimen would begin to maintain a certain plasma concentration. An infusion of the novel antishiver drug could be used to maintain the plasma concentration. When the cooling was complete the patient would be rewarmed and the drugs discontinued.

Another ideal antishiver drug may be nefopam. Nefopam is widely used as an analgesic, particularly outside the U.S. While it is not an analog of meperidine, it has similar structural and conformational properties. For example it has a phenyl group attached to a N-methyl ring, and the phenyl group prefers the equatorial position. Similar to meperidine, nefopam is known to prevent post-operative shivering and to prevent shivering related to Amphotericin B administration. However, nefopam has less respiratory depression side effects, and is not metabolized into a neurotoxic compound. Injectable nefopam is a racemic mixture. Analgesic activity resides in the (+) enantiomer. The (−) enantiomer may be a selective anti-shiver drug and superior to the racemic form. Combining nefopam with intravascular catheter based cooling induction may allow for successful implementation of therapeutic hypothermia.

It may also be desirable to use combinations of the compounds listed above or combine them with other drugs that can reduce shivering and lower the threshold. This may lower the doses needed for either drug and reduce side effects. For example, one could combine nefopam with (−) alpha-prodine, meperidine, thorazine, buspirone, clonidine, tramadol, or other medications to achieve the desired effect. The same combinations could be used with (−) alpha-prodine. There are many other combinations that could be tried including combining three agents together. These combinations can be used with endovascular or surface hypothermia induction for therapeutic purposes.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

TABLE I

| Δ Patient Target-$T_{Blood}$ Sampled | 14 fr Sampling Interval | Duty Cycle |
| --- | --- | --- |
| 4° C. | 30 minutes | 95% |
| 3° C. | 20 minutes | 93% |
| 2° C. | 15 minutes | 90% |
| 1° C. | 7 minutes | 82% |
| 0.5° C. | 3 minutes | 66% |
| 0.25° C. | 1.5 minutes | 50% |

*Assuming 1.5 minute sampling time (pump off).

TABLE II

| Time (seconds) | Temp. ° C. | Δ from Steady State |
| --- | --- | --- |
| 0 | ~18.2° C. | 19.2° C. |
| 10 | 35.5 | 1.9° C. |
| 20 | 36.7 | 0.7° C. |
| 24 | 36.9 | 0.5° C. |
| 26 | 37.0 | 0.4° C. |
| 29 | 37.1 | 0.3° C. |
| 35 | 37.2 | 0.2° C. |
| 50 | 37.3 | 0.1° C. |
| 90 | 37.4 | 0.0 |

TABLE III

| Catheter Size | Max Cooling Rate Observed | Max. Rewarm Rate Observed |
| --- | --- | --- |
| 14 fr | <8° C./Hr | <4.0° C./Hr |
| 9 fr | <4° C./Hr Estimated | <4.0° C./Hr with an accelerated rewarm (50° C. Bath) |

TABLE IV

| Current Temp. − Target Temp. | 9 fr. | 14 fr. |
| --- | --- | --- |
| 37° − 33° C. = 4° C. "cooling" | 60 minutes | 30 minutes |
| 36° − 33° C. = 3° C. | 45 minutes | 22.5 minutes |
| 35° − 33° C. = 2° C. | 30 minutes | 15 minutes |
| 34° − 33° C. = 1° C. | 15 minutes | 7.5 minutes |
| 34.5° − 33° C. = 0.5° C. | 7.5 minutes | 3.7 minutes |
| 33° − 37° C. = 4° C. "warming" | 60 minutes | 60 minutes |
| 34° − 37° C. = 3° C. | 45 minutes | 45 minutes |
| 35° − 37° C. = 2° C. | 30 minutes | 30 minutes |
| 36° − 37° C. = 1° C. | 15 minutes | 15 minutes |
| 36.5° − 37° C. = 0.5° C. | 7.5 minutes | 7.5 minutes |

TABLE V

| | | Interval Time Run | |
| --- | --- | --- | --- |
| | E (O | 9 fr. | 14 fr. |
| warming mode | −4° C. to −3° C. | 30 | 30 |
| | −3° C. to −2° C. | 20 | 20 |
| | −2° C. to −1° C. | 10 | 10 |
| | −1° C. to −0.5° C. | 5 | 5 |
| | <0.5° C. | 2 minutes | 1 minutes |
| cooling mode | 1 to 0.5° C. | 5 minutes | 3 minutes |
| | 1 to 2° C. | 10 minutes | 5 minutes |
| | 2 to 3° C. | 20 minutes | 10 minutes |
| | 3 to 4° C. | 30 minutes | 20 minutes |
| | >4° C. | 45 minutes | 30 minutes |
| warming mode | <−0.5 | 2 minutes | |

TABLE VI

| Example Servo Error | Example Pump/Power % |
| --- | --- |
| >0.18° C. | 100% |
| 0.18° C. to 0.135° C. | 75% |
| 0.09° C. to 0.045° C. | 50% |
| 0.045° C. to 0.000° C. | 25% |
| 0.000° C. | 0% |

TABLE VII

| A1/A2 Ratio | B |
| --- | --- |
| 0.565 | 6 seconds |
| 0.513 | 8 seconds |
| 0.478 | 10 seconds |
| 0.455 | 12 seconds |
| 0.439 | 14 seconds |
| 0.426 | 16 seconds |
| 0.415 | 18 seconds |

TABLE VIII

| Error Source | Error Magnitude 2 S.D. |
|---|---|
| Steady state error in maintenance (due to system power & gain capability) | 0.06 C. |
| Temperature sensor accuracy | <0.10 C. |
| Hardware/signal processing | 0.10 C. |
| Estimation algorithm | 0.20 C. |
| Patient rewarming during sampling period | 0.05 C. |

The invention claimed is:

1. In a system in which a working fluid is circulated through a catheter and a heal transfer element, the working fluid having a temperature different from a patient temperature, a method of controlling the administration of a thermal therapy, comprising:

entering a target patient temperature into the system;
   inserting a catheter having a heat transfer element positioned at a distal tip of the catheter into a blood vessel of a patient, the catheter having a supply lumen fin supplying a working fluid to the heat transfer element and a return lumen for returning a working fluid from the heat transfer element;
   circulating a working fluid through the catheter and the heat transfer element, the working fluid having a temperature different from the patient temperature;
   circulating a working fluid and not determining a control temperature, for a predetermined period of time based on the difference between a temperature determined from a signal from a temperature sensor mounted at or adjacent the distal tip of the heat transfer element and the target patient temperature;
   after the predetermined period of time, receiving a signal from the temperature sensor and determining a control temperature based on the signal;
   using the control temperature to control the temperature of the working fluid.

2. The method of claim 1, further comprising causing the working fluid to stop circulating, and wherein the receiving includes:
   allowing a first interval of time to pass; and
   collecting data from the temperature sensor during a second interval of time. such that the allowing and collecting each follow the causing.

3. The method of claim 2, wherein no data is collected during the first interval.

4. The method of claim 3, wherein data is collected during the second interval at a predetermined frequency.

5. The method of claim 2, wherein the first interval is between about 5 and 15 seconds.

6. The method of claim 5, wherein the first interval is between about 10 and 12 seconds.

7. The method of claim 2, wherein the second interval is between about 10 and 30 seconds.

8. The method claim 7, wherein the second interval is between about 15 and 25 seconds.

9. The method of claim 2, wherein the first interval is about the same length of time as second interval.

10. The method of claim 2, wherein the first and second intervals are different lengths of time.

11. The method of claim 2, further comprising integrating a value of the signal over the first interval with respect to time to derive a first area.

12. The method of claim 11, further comprising integrating a value of the signal over the second interval with respect to time to derive a second area.

13. The method of claim 12, further comprising dividing the first area by the second area to calculate a value that is a function of a time constant of an exponential function.

14. The method of claim 13, further comprising constructing a look-up table for the function of the time constant and the results of the division of the first area by the second area.

15. The method of claim 14, further comprising determining a magnitude of the exponential function using the first area, the second area, and the time constant.

16. The method of claim 15, wherein the determining further comprises calculating the projected control temperature based on the signal from the temperature sensor as measured at the end of the second interval, the magnitude of the exponential function, and the time constant of the exponential function.

17. The method of claim 2, wherein the second interval of time is at least one minute.

18. The method of claim 2, wherein the time during which the working fluid is caused to stop circulating, divided by the sum of the time during which the working fluid is caused to stop circulating plus the time during which the working fluid is circulating, is greater than about 90%.

19. The method of claim 2, wherein the determining includes:
   assuming a range of time constants for an exponential;
   performing a least squares fit between the collected data and the exponential for each of the range of time constants to calculate an error value that is a function of the time constant; and
   minimizing the error value to determine a unique value of the time constant.

20. The method of claim 19, further comprising using the unique value of the time constant to determine the projected control temperature.

21. The method of claim 19, further comprising determining the magnitude of the exponential.

22. The method of claim 19, further comprising determining a first-order linear component and adding the first-order linear component to the exponential to determine the projected control temperature.

23. The method claim 22, further comprising determining a higher-order components and adding the higher-order components to the exponential to determine the projected control temperature.

24. The method of claim 22, further comprising administering an anti-shivering agent to the patient.

25. The method of claim 1, wherein the temperature sensor is selected from the group consisting of thermistors, thermocouples, and combinations thereof.

26. The method of claim 25, wherein the temperature sensor is two thermistors, and further comprising receiving a safety monitor signal from one of the two thermistors.

27. The method of claim 26, further comprising causing the working fluid to stop circulating if a value of control temperature measured by the safety monitor signal falls outside a predetermined range.

28. The method of claim 27, wherein the predetermined range is 31° C. to 37° C.

29. The method of claim 1, wherein tile temperature sensor is disposed in a polymer tube.

30. The method of claim 29, wherein the polymer is polyamide.

31. The method of claim 1, wherein the temperature sensor is a thermistor.

32. The method of claim 1, wherein the working fluid has a temperature below the current patient temperature, and wherein the predetermined period of time is greater than about 30 minutes.

33. The method of claim 1, wherein the working fluid has a temperature above the current patient temperature, and wherein the predetermined period of time is greater than about 15 minutes.

34. The method of claim 1, wherein the predetermined period of time is directly proportional to the difference between the current patient temperature and the target patient temperature.

35. The method of claim 1, wherein the circulating includes circulating the working fluid at a maximum pump speed.

36. The method of claim 1, wherein the circulating includes circulating the working fluid at a power of pump speed which is proportional to the difference between the current patient temperature and the target patient temperature.

37. The method of claim 1, wherein the predetermined period of rime is determined by the initial patient temperature minus the sum of the target patient temperature and a constant, divided by the maximum rate of change of temperature, pertaining to a desired thermal therapy.

38. The method of claim 37, wherein the desired thermal therapy is inducing hypothermia.

39. The method of claim 37, wherein the desired thermal therapy is rewarming.

40. The method of claim 1, wherein the temperature sensor is encapsulated in a metal tube.

41. A heat transfer catheter for inducing a therapeutic state of hypothermia in a patient, for maintaining the temperature of a patient, or for rewarming a patient, comprising:
a catheter having a proximal end capable of being coupled to an input of a source of working fluid and a distal end coupled to a heat transfer element;
a supply lumen disposed within the catheter, the proximal end of the supply lumen capable of being coupled to an output of a source of working fluid and a distal end terminating at or within the heat transfer element; and
a temperature sensor disposed on or within the heat transfer element,
wherein the heat transfer element includes at least two heat transfer segments separated by a flexible joint, and
wherein the heat transfer segments have helical ridges and grooves.

42. The catheter of claim 41, wherein the flexible joint includes bellows.

43. A heat transfer catheter for inducing a therapeutic stale of hypothermia in a patient, for maintaining the temperature of a patient, or for rewarming a patient, comprising:
a catheter having a proximal end capable of being coupled to an input of a source of working fluid and a distal end coupled to a heat transfer element;
a supply lumen disposed within the catheter, the proximal end of the supply lumen capable of being coupled to an output of a source of working fluid and a distal end terminating at or within the heat transfer element; and
a temperature sensor disposed on or within the heat transfer element,
wherein the heat transfer element includes a straight supply lumen and a helical return lumen, the helical return lumen encircling the straight supply lumen.

44. The catheter of claim 43, wherein the heat transfer element includes a straight supply lumen and multiple helical return lumens, the multiple helical return lumens encircling the straight supply lumen.

* * * * *